United States Patent
Franzoso et al.

(10) Patent No.: US 10,697,019 B2
(45) Date of Patent: *Jun. 30, 2020

(54) METHOD OF DIAGNOSIS AND PROGNOSIS

(75) Inventors: Guido Franzoso, London (GB); Laura Tornatore, London (GB); Menotti Ruvo, San Nicola la Strada (IT); Alberto Rocci, Turin (IT); Antonio Palumbo, Turin (IT)

(73) Assignee: IMPERIAL COLLEGE INNOVATIONS LIMITED, London (GB)

( * ) Notice: Subject to any disclaimer, the term of this patent is extended or adjusted under 35 U.S.C. 154(b) by 350 days.

This patent is subject to a terminal disclaimer.

(21) Appl. No.: 14/113,518

(22) PCT Filed: Apr. 27, 2012

(86) PCT No.: PCT/GB2012/050947
§ 371 (c)(1),
(2), (4) Date: Jan. 13, 2014

(87) PCT Pub. No.: WO2012/146940
PCT Pub. Date: Nov. 1, 2012

(65) Prior Publication Data
US 2014/0128330 A1    May 8, 2014

(30) Foreign Application Priority Data
Apr. 27, 2011  (GB) .................................. 1107118.0

(51) Int. Cl.
*C12Q 1/68*     (2018.01)
*C12Q 1/6886*   (2018.01)

(52) U.S. Cl.
CPC ...... *C12Q 1/6886* (2013.01); *C12Q 2600/118* (2013.01); *C12Q 2600/158* (2013.01)

(58) Field of Classification Search
None
See application file for complete search history.

(56) References Cited

U.S. PATENT DOCUMENTS

| 2003/0077262 | A1  | 4/2003  | Franzoso et al. |
| 2004/0101916 | A1  | 5/2004  | Yen et al. |
| 2005/0112630 | A1* | 5/2005  | Shaughnessy ....... C12Q 1/6886 435/6.14 |
| 2009/0264306 | A1  | 10/2009 | Caldwell et al. |
| 2009/0312396 | A1  | 12/2009 | Byth et al. |
| 2010/0144673 | A1  | 6/2010  | Shaughnessy, Jr. et al. |
| 2014/0274788 | A1  | 9/2014  | Ishikawa et al. |

FOREIGN PATENT DOCUMENTS

| JP | 2007217358 | * | 8/2007 |
| JP | 2009544583 | A | 12/2009 |
| WO | WO 2003/068935 | | 8/2003 |
| WO | WO 2004/016744 | | 2/2004 |
| WO | WO 2010/040124 | | 4/2011 |
| WO | WO 2011/048390 | | 4/2011 |
| WO | WO-2011048390 | A2 | 4/2011 |
| WO | WO 2011/147987 | | 12/2011 |

OTHER PUBLICATIONS

Lam et al; Clinical Cancer Research, vol. 11, pp. 28-40, 2005.*
(Lee et al; Pharmacotherapy, Abstract, 2006, vol. 26.*
D'Angelo V., et al. (2009), "High erk-I activation and gadd45a expression as prognostic markers in high risk pediatric haemolymphoproliferative diseases", *Journal of Experimental & Clinical Cancer Research*, 28(39): 1-8.
De Smaele, Enrico, et al. (2001), "Induction of gabb45beta by NF-kappaB downregulates pro-apoptotic JNK signaling", *Nature: International Weekly Journal of Science*, 44(6861):308-313.
Haematol Br J., (2003) "Criteria for the classification of monoclonal gammopathies, multiple myeloma and related disorders: a report of the International Myeloma Working Group," *International Myeloma Working Group*, 121(5)749-57.
Liebermann, D., et al. (2011), "Gadd45 stress sensors in malignancy and leukemia", *Crit Rev Oncog.*, 161(1-2): 129-140.
Papa, S., et al. (2004), "Gadd45β mediates the NK-κB suppression if JNK signaling by targeting MKK7/JNKK2", Nature Cell Biology, 6(2): 146-153.
Qui, W., et al. (2003), "Down Refulation of Growth Arrest DNA Damage-Inducible Gene 45β Expression is Assoviated with Human Hepatocellular Carcinoma", *American Journal of Pathology*, 162(6) 1961-1974.
Zenmyo, M., et al. (2010), "Gadd45β expression in chondrosarcoma: a pilot study for diagnostic and biological implications in histological grading", *Diagnostic Pathology*, 5(69): 1-5.
International Search Report and Written Opinion dated Nov. 9, 2013 issued in PCT/GB2012/050947.

* cited by examiner

*Primary Examiner* — Jehanne S Sitton
(74) *Attorney, Agent, or Firm* — Harness Dickey & Pierce P.L.C.

(57) ABSTRACT

A method of measuring Gadd45β expression comprising the step of measuring Gadd45β expression levels in a sample of cells, for example CD 138 expressing cells, obtained from a subject known to have or suspected of having a haematological malignancy. Expression levels may be used in diagnosis, for example of multiple myeloma, in providing a prognosis, for example in a patient having multiple myeloma or in guiding selection of an appropriate treatment agent, especially a treatment agent comprising Gadd45β and or MKK7 inhibitors. Also datasets comprising measured expression levels from multiple subjects.

6 Claims, 7 Drawing Sheets

Specification includes a Sequence Listing.

B

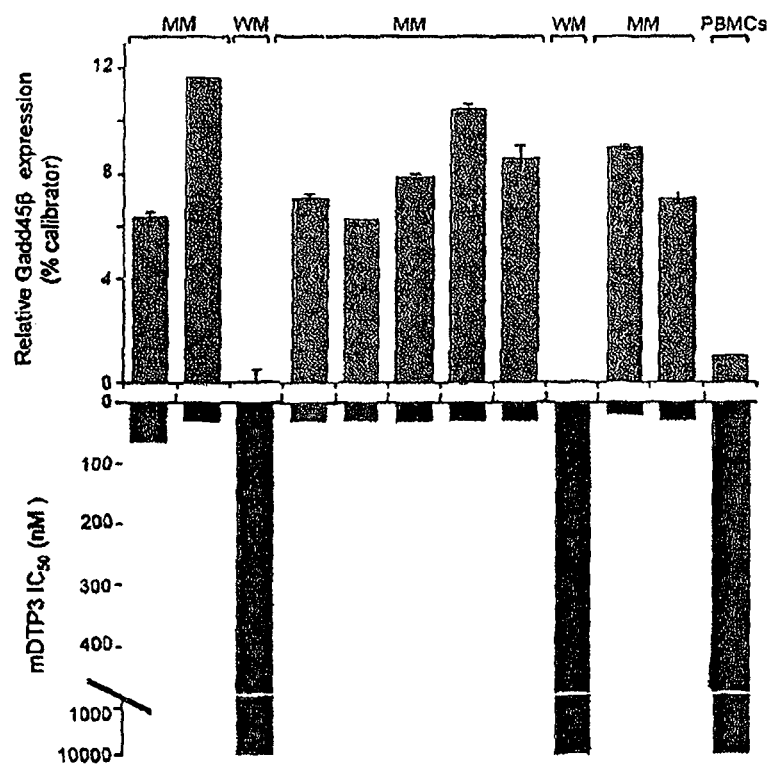

B

SEQUENCE LISTING

```
<160> NUMBER OF SEQ ID NOS: 228

<210> SEQ ID NO 1
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MISC_FEATURE
<222> LOCATION: (1)..(4)
<223> OTHER INFORMATION: residues 1 - 4 are D-amino acids
<220> FEATURE:
<221> NAME/KEY: MOD_RES
<222> LOCATION: (1)..(1)
<223> OTHER INFORMATION: benzyloxycarbonyl N-terminal group
<220> FEATURE:
```

```
<221> NAME/KEY: MOD_RES
<222> LOCATION: (4)..(4)
<223> OTHER INFORMATION: AMINATION

<400> SEQUENCE: 1

Tyr Glu Arg Phe
1

<210> SEQ ID NO 2
<211> LENGTH: 4
<212> TYPE: PRT
<213> ORGANISM: Artificial Sequence
<220> FEATURE:
<223> OTHER INFORMATION: Therapeutic agent

<400> SEQUENCE: 2

Tyr Asp His Phe
1

<210> SEQ ID NO 3
<211> LENGTH: 4
<212> TYPE: PRT
<213> ORGANISM: Artificial Sequence
<220> FEATURE:
<223> OTHER INFORMATION: Therapeutic agent

<400> SEQUENCE: 3

Tyr Glu Arg Phe
1

<210> SEQ ID NO 4
<211> LENGTH: 4
<212> TYPE: PRT
<213> ORGANISM: Artificial Sequence
<220> FEATURE:
<223> OTHER INFORMATION: Therapeutic agent

<400> SEQUENCE: 4

Tyr Glu His Phe
1

<210> SEQ ID NO 5
<211> LENGTH: 4
<212> TYPE: PRT
<213> ORGANISM: Artificial Sequence
<220> FEATURE:
<223> OTHER INFORMATION: Therapeutic agent

<400> SEQUENCE: 5

Trp Asp His Phe
1

<210> SEQ ID NO 6
<211> LENGTH: 4
<212> TYPE: PRT
<213> ORGANISM: Artificial Sequence
<220> FEATURE:
<223> OTHER INFORMATION: Therapeutic agent

<400> SEQUENCE: 6

Trp Glu His Phe
1

<210> SEQ ID NO 7
<211> LENGTH: 4
<212> TYPE: PRT
<213> ORGANISM: Artificial Sequence
```

```
<220> FEATURE:
<223> OTHER INFORMATION: Therapeutic agent

<400> SEQUENCE: 7

Tyr Asp Arg Phe
1

<210> SEQ ID NO 8
<211> LENGTH: 4
<212> TYPE: PRT
<213> ORGANISM: Artificial Sequence
<220> FEATURE:
<223> OTHER INFORMATION: Therapeutic agent

<400> SEQUENCE: 8

Tyr Asp Lys Phe
1

<210> SEQ ID NO 9
<211> LENGTH: 4
<212> TYPE: PRT
<213> ORGANISM: Artificial Sequence
<220> FEATURE:
<223> OTHER INFORMATION: Therapeutic agent

<400> SEQUENCE: 9

Tyr Glu Lys Phe
1

<210> SEQ ID NO 10
<211> LENGTH: 4
<212> TYPE: PRT
<213> ORGANISM: Artificial Sequence
<220> FEATURE:
<223> OTHER INFORMATION: Therapeutic agent

<400> SEQUENCE: 10

Trp Glu Lys Phe
1

<210> SEQ ID NO 11
<211> LENGTH: 4
<212> TYPE: PRT
<213> ORGANISM: Artificial Sequence
<220> FEATURE:
<223> OTHER INFORMATION: Therapeutic agent

<400> SEQUENCE: 11

Trp Glu Arg Phe
1

<210> SEQ ID NO 12
<211> LENGTH: 4
<212> TYPE: PRT
<213> ORGANISM: Artificial Sequence
<220> FEATURE:
<223> OTHER INFORMATION: Therapeutic agent

<400> SEQUENCE: 12

Trp Asp Lys Phe
1

<210> SEQ ID NO 13
<211> LENGTH: 4
<212> TYPE: PRT
<213> ORGANISM: Artificial Sequence
<220> FEATURE:
```

```
<223> OTHER INFORMATION: Therapeutic agent

<400> SEQUENCE: 13

Trp Asp Arg Phe
1

<210> SEQ ID NO 14
<211> LENGTH: 4
<212> TYPE: PRT
<213> ORGANISM: Artificial Sequence
<220> FEATURE:
<223> OTHER INFORMATION: Therapeutic agent

<400> SEQUENCE: 14

Tyr Asp His Trp
1

<210> SEQ ID NO 15
<211> LENGTH: 4
<212> TYPE: PRT
<213> ORGANISM: Artificial Sequence
<220> FEATURE:
<223> OTHER INFORMATION: Therapeutic agent

<400> SEQUENCE: 15

Tyr Glu His Trp
1

<210> SEQ ID NO 16
<211> LENGTH: 4
<212> TYPE: PRT
<213> ORGANISM: Artificial Sequence
<220> FEATURE:
<223> OTHER INFORMATION: Therapeutic agent

<400> SEQUENCE: 16

Trp Asp His Trp
1

<210> SEQ ID NO 17
<211> LENGTH: 4
<212> TYPE: PRT
<213> ORGANISM: Artificial Sequence
<220> FEATURE:
<223> OTHER INFORMATION: Therapeutic agent

<400> SEQUENCE: 17

Trp Glu His Trp
1

<210> SEQ ID NO 18
<211> LENGTH: 4
<212> TYPE: PRT
<213> ORGANISM: Artificial Sequence
<220> FEATURE:
<223> OTHER INFORMATION: Therapeutic agent

<400> SEQUENCE: 18

Tyr Asp Arg Trp
1

<210> SEQ ID NO 19
<211> LENGTH: 4
<212> TYPE: PRT
<213> ORGANISM: Artificial Sequence
<220> FEATURE:
<223> OTHER INFORMATION: Therapeutic agent
```

```
<400> SEQUENCE: 19

Tyr Asp Lys Trp
1

<210> SEQ ID NO 20
<211> LENGTH: 4
<212> TYPE: PRT
<213> ORGANISM: Artificial Sequence
<220> FEATURE:
<223> OTHER INFORMATION: Therapeutic agent

<400> SEQUENCE: 20

Tyr Glu Lys Trp
1

<210> SEQ ID NO 21
<211> LENGTH: 4
<212> TYPE: PRT
<213> ORGANISM: Artificial Sequence
<220> FEATURE:
<223> OTHER INFORMATION: Therapeutic agent

<400> SEQUENCE: 21

Tyr Glu Arg Trp
1

<210> SEQ ID NO 22
<211> LENGTH: 4
<212> TYPE: PRT
<213> ORGANISM: Artificial Sequence
<220> FEATURE:
<223> OTHER INFORMATION: Therapeutic agent

<400> SEQUENCE: 22

Trp Glu Lys Trp
1

<210> SEQ ID NO 23
<211> LENGTH: 4
<212> TYPE: PRT
<213> ORGANISM: Artificial Sequence
<220> FEATURE:
<223> OTHER INFORMATION: Therapeutic agent

<400> SEQUENCE: 23

Trp Glu Arg Trp
1

<210> SEQ ID NO 24
<211> LENGTH: 4
<212> TYPE: PRT
<213> ORGANISM: Artificial Sequence
<220> FEATURE:
<223> OTHER INFORMATION: Therapeutic agent

<400> SEQUENCE: 24

Trp Asp Lys Trp
1

<210> SEQ ID NO 25
<211> LENGTH: 4
<212> TYPE: PRT
<213> ORGANISM: Artificial Sequence
<220> FEATURE:
<223> OTHER INFORMATION: Therapeutic agent
```

```
<400> SEQUENCE: 25

Trp Asp Lys Trp
1

<210> SEQ ID NO 26
<211> LENGTH: 4
<212> TYPE: PRT
<213> ORGANISM: Artificial Sequence
<220> FEATURE:
<223> OTHER INFORMATION: Therapeutic agent

<400> SEQUENCE: 26

Tyr Asp His Tyr
1

<210> SEQ ID NO 27
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MISC_FEATURE
<222> LOCATION: (1)..(4)
<223> OTHER INFORMATION: residues 1 - 4 are D-amino acids

<400> SEQUENCE: 27

Tyr Glu Arg Phe
1

<210> SEQ ID NO 28
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MISC_FEATURE
<222> LOCATION: (1)..(4)
<223> OTHER INFORMATION: residues 1 - 4 are D-amino acids

<400> SEQUENCE: 28

Tyr Asp His Phe
1

<210> SEQ ID NO 29
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MISC_FEATURE
<222> LOCATION: (1)..(4)
<223> OTHER INFORMATION: residues 1 - 4 are D-amino acids

<400> SEQUENCE: 29

Trp Glu Arg Phe
1

<210> SEQ ID NO 30
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: misc_feature
<222> LOCATION: (1)..(4)
```

-continued

<223> OTHER INFORMATION: residues 1 - 4 are D-amino acids

<400> SEQUENCE: 30

Trp Glu His Phe
1

<210> SEQ ID NO 31
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: misc_feature
<222> LOCATION: (1)..(4)
<223> OTHER INFORMATION: residues 1 - 4 are D-amino acids

<400> SEQUENCE: 31

Tyr Asp Arg Phe
1

<210> SEQ ID NO 32
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MISC_FEATURE
<222> LOCATION: (1)..(4)
<223> OTHER INFORMATION: residues 1 - 4 are D-amino acids

<400> SEQUENCE: 32

Tyr Asp His Tyr
1

<210> SEQ ID NO 33
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MISC_FEATURE
<222> LOCATION: (1)..(4)
<223> OTHER INFORMATION: residues 1 - 4 are D-amino acids

<400> SEQUENCE: 33

Tyr Glu Arg Tyr
1

<210> SEQ ID NO 34
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MISC_FEATURE
<222> LOCATION: (1)..(4)
<223> OTHER INFORMATION: residues 1 - 4 are D-amino acids

<400> SEQUENCE: 34

Trp Asp His Phe
1

<210> SEQ ID NO 35
<211> LENGTH: 4
<212> TYPE: PRT

```
<213> ORGANISM: Artificial Sequence
<220> FEATURE:
<223> OTHER INFORMATION: Therapeutic sequence
<220> FEATURE:
<221> NAME/KEY: MISC_FEATURE
<222> LOCATION: (1)..(4)
<223> OTHER INFORMATION: residues 1 - 4 are D-amino acids

<400> SEQUENCE: 35

Trp Glu Arg Phe
1

<210> SEQ ID NO 36
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MISC_FEATURE
<222> LOCATION: (1)..(4)
<223> OTHER INFORMATION: residues 1 - 4 are D-amino acids

<400> SEQUENCE: 36

Tyr Asp Lys Phe
1

<210> SEQ ID NO 37
<211> LENGTH: 5
<212> TYPE: PRT
<213> ORGANISM: Artificial Sequence
<220> FEATURE:
<223> OTHER INFORMATION: Therapeutic agent
<220> FEATURE:
<221> NAME/KEY: MISC_FEATURE
<222> LOCATION: (1)..(4)
<223> OTHER INFORMATION: D or L amino acid configuration not specified.
      Both configurations encompassed.
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: AMIDATION

<400> SEQUENCE: 37

Phe Tyr Glu Arg Phe
1               5

<210> SEQ ID NO 38
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MISC_FEATURE
<222> LOCATION: (1)..(4)
<223> OTHER INFORMATION: D or L amino acid configuration not specified.
      Both configurations encompassed.
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: AMIDATION

<400> SEQUENCE: 38
```

Tyr Asp His Phe
1

<210> SEQ ID NO 39
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MISC_FEATURE
<222> LOCATION: (1)..(4)
<223> OTHER INFORMATION: D or L amino acid configuration not specified.
      Both configurations encompassed.
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: AMIDATION

<400> SEQUENCE: 39

Tyr Asp Lys Phe
1

<210> SEQ ID NO 40
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MISC_FEATURE
<222> LOCATION: (1)..(4)
<223> OTHER INFORMATION: D or L amino acid configuration not specified.
      Both configurations encompassed.
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: AMIDATION

<400> SEQUENCE: 40

Tyr Glu Lys Phe
1

<210> SEQ ID NO 41
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MISC_FEATURE
<222> LOCATION: (1)..(4)
<223> OTHER INFORMATION: D or L amino acid configuration not specified.
      Both configurations encompassed.
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: AMIDATION

<400> SEQUENCE: 41

Tyr Glu His Phe

```
<210> SEQ ID NO 42
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MISC_FEATURE
<222> LOCATION: (1)..(4)
<223> OTHER INFORMATION: D or L amino acid configuration not specified.
      Both configurations encompassed.
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: AMIDATION

<400> SEQUENCE: 42

Tyr Asp Arg Phe
1

<210> SEQ ID NO 43
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MISC_FEATURE
<222> LOCATION: (1)..(4)
<223> OTHER INFORMATION: D or L amino acid configuration not specified.
      Both configurations encompassed.
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: AMIDATION

<400> SEQUENCE: 43

Trp Glu His Phe
1

<210> SEQ ID NO 44
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MISC_FEATURE
<222> LOCATION: (1)..(4)
<223> OTHER INFORMATION: D or L amino acid configuration not specified.
      Both configurations encompassed.
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: AMIDATION

<400> SEQUENCE: 44

Trp Glu Lys Phe
1
```

```
<210> SEQ ID NO 45
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MISC_FEATURE
<222> LOCATION: (1)..(4)
<223> OTHER INFORMATION: D or L amino acid configuration not specified.
      Both configurations encompassed.
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: AMIDATION

<400> SEQUENCE: 45

Trp Glu His Phe
1

<210> SEQ ID NO 46
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MISC_FEATURE
<222> LOCATION: (1)..(4)
<223> OTHER INFORMATION: D or L amino acid configuration not specified.
      Both configurations encompassed.
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: AMIDATION

<400> SEQUENCE: 46

Trp Asp Lys Phe
1

<210> SEQ ID NO 47
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MISC_FEATURE
<222> LOCATION: (1)..(4)
<223> OTHER INFORMATION: D or L amino acid configuration not specified.
      Both configurations encompassed.
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: AMIDATION

<400> SEQUENCE: 47

Tyr Glu Arg Tyr
1
```

```
<210> SEQ ID NO 48
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MISC_FEATURE
<222> LOCATION: (1)..(4)
<223> OTHER INFORMATION: D or L amino acid configuration not specified.
      Both configurations encompassed.
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: AMIDATION

<400> SEQUENCE: 48

Thr Asp Lys Tyr
1

<210> SEQ ID NO 49
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MISC_FEATURE
<222> LOCATION: (1)..(4)
<223> OTHER INFORMATION: D or L amino acid configuration not specified.
      Both configurations encompassed.
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: AMIDATION

<400> SEQUENCE: 49

Tyr Glu Lys Tyr
1

<210> SEQ ID NO 50
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MISC_FEATURE
<222> LOCATION: (1)..(4)
<223> OTHER INFORMATION: D or L amino acid configuration not specified.
      Both configurations encompassed.
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: AMIDATION

<400> SEQUENCE: 50

Tyr Glu His Tyr
1
```

```
<210> SEQ ID NO 51
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MISC_FEATURE
<222> LOCATION: (1)..(4)
<223> OTHER INFORMATION: D or L amino acid configuration not specified.
      Both configurations encompassed.
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: AMIDATION

<400> SEQUENCE: 51

Tyr Asp Arg Tyr
1

<210> SEQ ID NO 52
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MISC_FEATURE
<222> LOCATION: (1)..(4)
<223> OTHER INFORMATION: D or L amino acid configuration not specified.
      Both configurations encompassed.
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: AMIDATION

<400> SEQUENCE: 52

Trp Glu His Tyr
1

<210> SEQ ID NO 53
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MISC_FEATURE
<222> LOCATION: (1)..(4)
<223> OTHER INFORMATION: D/L configuration no specified. both
      configurations encompassed
<220> FEATURE:
<221> NAME/KEY: MISC_FEATURE
<222> LOCATION: (1)..(4)
<223> OTHER INFORMATION: D or L amino acid configuration not specified.
      Both configurations encompassed.
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: AMIDATION

<400> SEQUENCE: 53
```

Trp Glu Lys Tyr
1

<210> SEQ ID NO 54
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MISC_FEATURE
<222> LOCATION: (1)..(4)
<223> OTHER INFORMATION: D or L amino acid configuration not specified.
      Both configurations encompassed.
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: AMIDATION

<400> SEQUENCE: 54

Trp Asp His Tyr
1

<210> SEQ ID NO 55
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MISC_FEATURE
<222> LOCATION: (1)..(4)
<223> OTHER INFORMATION: D or L amino acid configuration not specified.
      Both configurations encompassed.
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: AMIDATION

<400> SEQUENCE: 55

Trp Glu Lys Tyr
1

<210> SEQ ID NO 56
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MISC_FEATURE
<222> LOCATION: (1)..(4)
<223> OTHER INFORMATION: D or L amino acid configuration not specified.
      Both configurations encompassed.
<220> FEATURE:
<221> NAME/KEY: MISC_FEATURE
<222> LOCATION: (1)..(4)
<223> OTHER INFORMATION: INTERNAL LACTAM
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: AMIDATION

<400> SEQUENCE: 56

Tyr Glu Lys Phe
1

<210> SEQ ID NO 57
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MISC_FEATURE
<222> LOCATION: (1)..(4)
<223> OTHER INFORMATION: D or L amino acid configuration not specified.
      Both configurations encompassed.
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: AMIDATION

<400> SEQUENCE: 57

Tyr Gln Arg Phe
1

<210> SEQ ID NO 58
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MISC_FEATURE
<222> LOCATION: (1)..(4)
<223> OTHER INFORMATION: D or L amino acid configuration not specified.
      Both configurations encompassed.
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: AMIDATION

<400> SEQUENCE: 58

Tyr Met Arg Phe
1

<210> SEQ ID NO 59
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MISC_FEATURE
<222> LOCATION: (1)..(4)
<223> OTHER INFORMATION: D or L amino acid configuration not specified.
      Both configurations encompassed.
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: AMIDATION

```
<400> SEQUENCE: 59

Tyr Leu Arg Phe
1

<210> SEQ ID NO 60
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MISC_FEATURE
<222> LOCATION: (1)..(4)
<223> OTHER INFORMATION: D or L amino acid configuration not specified.
      Both configurations encompassed.
<220> FEATURE:
<221> NAME/KEY: MOD_RES
<222> LOCATION: (1)..(1)
<223> OTHER INFORMATION: Benzyloxycarbonyl-Tyr
<220> FEATURE:
<221> NAME/KEY: MOD_RES
<222> LOCATION: (4)..(4)
<223> OTHER INFORMATION: AMIDATION

<400> SEQUENCE: 60

Tyr Glu Arg Phe
1

<210> SEQ ID NO 61
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MISC_FEATURE
<222> LOCATION: (1)..(4)
<223> OTHER INFORMATION: D or L amino acid configuration not specified.
      Both configurations encompassed.
<220> FEATURE:
<221> NAME/KEY: MOD_RES
<222> LOCATION: (1)..(1)
<223> OTHER INFORMATION: Benzyloxycarbonyl-Tyr
<220> FEATURE:
<221> NAME/KEY: MOD_RES
<222> LOCATION: (4)..(4)
<223> OTHER INFORMATION: AMIDATION

<400> SEQUENCE: 61

Tyr Asp His Phe
1

<210> SEQ ID NO 62
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MISC_FEATURE
<222> LOCATION: (1)..(4)
<223> OTHER INFORMATION: D or L amino acid configuration not specified.
      Both configurations encompassed.
<220> FEATURE:
<221> NAME/KEY: MOD_RES
<222> LOCATION: (1)..(1)
<223> OTHER INFORMATION: Benzyloxycarbonyl-Tyr
<220> FEATURE:
<221> NAME/KEY: MOD_RES
<222> LOCATION: (2)..(2)
<223> OTHER INFORMATION: 4-methyl ester aspartic acid (Asp(OMe))
<220> FEATURE:
<221> NAME/KEY: MOD_RES
```

<222> LOCATION: (4)..(4)
<223> OTHER INFORMATION: AMIDATION

<400> SEQUENCE: 62

Tyr Asp His Phe
1

<210> SEQ ID NO 63
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MISC_FEATURE
<222> LOCATION: (1)..(4)
<223> OTHER INFORMATION: D or L amino acid configuration not specified.
      Both configurations encompassed.
<220> FEATURE:
<221> NAME/KEY: MOD_RES
<222> LOCATION: (1)..(1)
<223> OTHER INFORMATION: (3-Methoxy,4-hydroxy-benzoyl)-Tyr
<220> FEATURE:
<221> NAME/KEY: MOD_RES
<222> LOCATION: (4)..(4)
<223> OTHER INFORMATION: AMIDATION

<400> SEQUENCE: 63

Tyr Glu Arg Phe
1

<210> SEQ ID NO 64
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MISC_FEATURE
<222> LOCATION: (1)..(4)
<223> OTHER INFORMATION: D or L amino acid configuration not specified.
      Both configurations encompassed.
<220> FEATURE:
<221> NAME/KEY: MOD_RES
<222> LOCATION: (1)..(1)
<223> OTHER INFORMATION: (3-Methoxy,4-hydroxy-benzoyl)-Tyr
<220> FEATURE:
<221> NAME/KEY: MOD_RES
<222> LOCATION: (4)..(4)
<223> OTHER INFORMATION: AMIDATION

<400> SEQUENCE: 64

Tyr Asp His Phe
1

<210> SEQ ID NO 65
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MISC_FEATURE
<222> LOCATION: (1)..(4)
<223> OTHER INFORMATION: D or L amino acid configuration not specified.
      Both configurations encompassed.
<220> FEATURE:
<221> NAME/KEY: MOD_RES
<222> LOCATION: (1)..(1)
<223> OTHER INFORMATION: N-(3-Methoxy,4-hydroxy-benzoyl)ation
<220> FEATURE:
<221> NAME/KEY: MOD_RES
<222> LOCATION: (2)..(2)

```
<223> OTHER INFORMATION: 4-methyl ester aspartic acid (Asp(OMe))
<220> FEATURE:
<221> NAME/KEY: MOD_RES
<222> LOCATION: (4)..(4)
<223> OTHER INFORMATION: AMIDATION

<400> SEQUENCE: 65

Tyr Asp His Phe
1

<210> SEQ ID NO 66
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MISC_FEATURE
<222> LOCATION: (1)..(4)
<223> OTHER INFORMATION: D or L amino acid configuration not specified.
      Both configurations encompassed.
<220> FEATURE:
<221> NAME/KEY: MOD_RES
<222> LOCATION: (1)..(1)
<223> OTHER INFORMATION: Fluorenylmethyloxycarbonyl-Tyr
<220> FEATURE:
<221> NAME/KEY: MOD_RES
<222> LOCATION: (4)..(4)
<223> OTHER INFORMATION: AMIDATION

<400> SEQUENCE: 66

Tyr Glu Arg Phe
1

<210> SEQ ID NO 67
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MISC_FEATURE
<222> LOCATION: (1)..(4)
<223> OTHER INFORMATION: D or L amino acid configuration not specified.
      Both configurations encompassed.
<220> FEATURE:
<221> NAME/KEY: MOD_RES
<222> LOCATION: (1)..(1)
<223> OTHER INFORMATION: Fluorenylmethyloxycarbonyl-Tyr
<220> FEATURE:
<221> NAME/KEY: MOD_RES
<222> LOCATION: (4)..(4)
<223> OTHER INFORMATION: AMIDATION

<400> SEQUENCE: 67

Tyr Asp His Phe
1

<210> SEQ ID NO 68
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MISC_FEATURE
<222> LOCATION: (1)..(4)
<223> OTHER INFORMATION: D or L amino acid configuration not specified.
      Both configurations encompassed.
<220> FEATURE:
<221> NAME/KEY: MOD_RES
<222> LOCATION: (1)..(1)
<223> OTHER INFORMATION: Fluorenylmethyloxycarbonyl-Tyr
```

```
<220> FEATURE:
<221> NAME/KEY: MOD_RES
<222> LOCATION: (2)..(2)
<223> OTHER INFORMATION: 4-methyl ester aspartic acid (Asp(OMe))
<220> FEATURE:
<221> NAME/KEY: MOD_RES
<222> LOCATION: (4)..(4)
<223> OTHER INFORMATION: AMIDATION

<400> SEQUENCE: 68

Tyr Asp His Phe
1

<210> SEQ ID NO 69
<211> LENGTH: 4
<212> TYPE: PRT
<213> ORGANISM: Artificial Sequence
<220> FEATURE:
<223> OTHER INFORMATION: therapeutic agent
<220> FEATURE:
<221> NAME/KEY: MISC_FEATURE
<222> LOCATION: (1)..(4)
<223> OTHER INFORMATION: D or L amino acid configuration not specified.
      Both configurations encompassed.
<220> FEATURE:
<221> NAME/KEY: MOD_RES
<222> LOCATION: (1)..(1)
<223> OTHER INFORMATION: Fluorenylmethyloxycarbonyl-Tyr
<220> FEATURE:
<221> NAME/KEY: MOD_RES
<222> LOCATION: (2)..(2)
<223> OTHER INFORMATION: 4-methyl ester aspartic acid (Asp(OMe))
<220> FEATURE:
<221> NAME/KEY: MOD_RES
<222> LOCATION: (4)..(4)
<223> OTHER INFORMATION: AMIDATION

<400> SEQUENCE: 69

Tyr Asp His Phe
1

<210> SEQ ID NO 70
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MISC_FEATURE
<222> LOCATION: (1)..(4)
<223> OTHER INFORMATION: D or L amino acid configuration not specified.
      Both configurations encompassed.
<220> FEATURE:
<221> NAME/KEY: MOD_RES
<222> LOCATION: (1)..(1)
<223> OTHER INFORMATION: Myristyl-Tyr
<220> FEATURE:
<221> NAME/KEY: MOD_RES
<222> LOCATION: (4)..(4)
<223> OTHER INFORMATION: AMIDATION

<400> SEQUENCE: 70

Tyr Glu Arg Phe
1

<210> SEQ ID NO 71
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MISC_FEATURE
```

```
<222> LOCATION: (1)..(4)
<223> OTHER INFORMATION: D or L amino acid configuration not specified.
      Both configurations encompassed.
<220> FEATURE:
<221> NAME/KEY: MOD_RES
<222> LOCATION: (1)..(1)
<223> OTHER INFORMATION: Myristyl-Tyr
<220> FEATURE:
<221> NAME/KEY: MOD_RES
<222> LOCATION: (4)..(4)
<223> OTHER INFORMATION: AMIDATION

<400> SEQUENCE: 71

Tyr Asp His Phe
1

<210> SEQ ID NO 72
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MISC_FEATURE
<222> LOCATION: (1)..(4)
<223> OTHER INFORMATION: D or L amino acid configuration not specified.
      Both configurations encompassed.
<220> FEATURE:
<221> NAME/KEY: MOD_RES
<222> LOCATION: (1)..(1)
<223> OTHER INFORMATION: Myristyl-Tyr
<220> FEATURE:
<221> NAME/KEY: MOD_RES
<222> LOCATION: (2)..(2)
<223> OTHER INFORMATION: 4-methyl ester aspartic acid
<220> FEATURE:
<221> NAME/KEY: MOD_RES
<222> LOCATION: (4)..(4)
<223> OTHER INFORMATION: AMIDATION

<400> SEQUENCE: 72

Tyr Asp His Phe
1

<210> SEQ ID NO 73
<211> LENGTH: 9
<212> TYPE: PRT
<213> ORGANISM: Artificial Sequence
<220> FEATURE:
<223> OTHER INFORMATION: Therapeutic agent
<220> FEATURE:
<221> NAME/KEY: MISC_FEATURE
<222> LOCATION: (1)..(9)
<223> OTHER INFORMATION: D or L amino acid configuration not specified.
      Both configurations encompassed.
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (9)..(9)
<223> OTHER INFORMATION: AMIDATION

<400> SEQUENCE: 73

Tyr Glu Arg Phe Gly Tyr Asp Arg Phe
1               5

<210> SEQ ID NO 74
<211> LENGTH: 9
<212> TYPE: PRT
<213> ORGANISM: Artificial Sequence
<220> FEATURE:
```

```
<223> OTHER INFORMATION: Therapeutic agent
<220> FEATURE:
<221> NAME/KEY: MISC_FEATURE
<222> LOCATION: (1)..(9)
<223> OTHER INFORMATION: D or L amino acid configuration not specified.
      Both configurations encompassed.
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (9)..(9)
<223> OTHER INFORMATION: AMIDATION

<400> SEQUENCE: 74

Tyr Asp His Phe Gly Tyr Asp His Phe
1               5

<210> SEQ ID NO 75
<211> LENGTH: 7
<212> TYPE: PRT
<213> ORGANISM: Artificial Sequence
<220> FEATURE:
<223> OTHER INFORMATION: Therapeutic agent
<220> FEATURE:
<221> NAME/KEY: MISC_FEATURE
<222> LOCATION: (1)..(7)
<223> OTHER INFORMATION: D or L amino acid configuration not specified.
      Both configurations encompassed.
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (7)..(7)
<223> OTHER INFORMATION: AMIDATION

<400> SEQUENCE: 75

Tyr Arg Phe Gly Tyr Arg Phe
1               5

<210> SEQ ID NO 76
<211> LENGTH: 9
<212> TYPE: PRT
<213> ORGANISM: Artificial Sequence
<220> FEATURE:
<223> OTHER INFORMATION: Therapeutic agent
<220> FEATURE:
<221> NAME/KEY: MISC_FEATURE
<222> LOCATION: (1)..(9)
<223> OTHER INFORMATION: D or L amino acid configuration not specified.
      Both configurations encompassed.
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (2)..(2)
<223> OTHER INFORMATION: 4-methyl ester aspartic acid
<220> FEATURE:
<221> NAME/KEY: MOD_RES
<222> LOCATION: (7)..(7)
<223> OTHER INFORMATION: 4-methyl ester aspartic acid
<220> FEATURE:
<221> NAME/KEY: MOD_RES
<222> LOCATION: (9)..(9)
<223> OTHER INFORMATION: AMIDATION

<400> SEQUENCE: 76

Tyr Asp His Phe Gly Tyr Asp His Phe
1               5
```

```
<210> SEQ ID NO 77
<211> LENGTH: 9
<212> TYPE: PRT
<213> ORGANISM: Artificial Sequence
<220> FEATURE:
<223> OTHER INFORMATION: Therapeutic agent
<220> FEATURE:
<221> NAME/KEY: MISC_FEATURE
<222> LOCATION: (1)..(9)
<223> OTHER INFORMATION: D or L amino acid configuration not specified.
      Both configurations encompassed.
<220> FEATURE:
<221> NAME/KEY: MOD_RES
<222> LOCATION: (1)..(1)
<223> OTHER INFORMATION: benzyloxycarbonyl-Tyr
<220> FEATURE:
<221> NAME/KEY: MOD_RES
<222> LOCATION: (9)..(9)
<223> OTHER INFORMATION: AMIDATION

<400> SEQUENCE: 77

Tyr Glu Arg Phe Gly Tyr Glu Arg Phe
1               5

<210> SEQ ID NO 78
<211> LENGTH: 9
<212> TYPE: PRT
<213> ORGANISM: Artificial Sequence
<220> FEATURE:
<223> OTHER INFORMATION: Therapeutic agent
<220> FEATURE:
<221> NAME/KEY: MISC_FEATURE
<222> LOCATION: (1)..(9)
<223> OTHER INFORMATION: D or L amino acid configuration not specified.
      Both configurations encompassed.
<220> FEATURE:
<221> NAME/KEY: MOD_RES
<222> LOCATION: (1)..(9)
<223> OTHER INFORMATION: benzyloxycarbonyl-Tyr
<220> FEATURE:
<221> NAME/KEY: MOD_RES
<222> LOCATION: (9)..(9)
<223> OTHER INFORMATION: AMIDATION

<400> SEQUENCE: 78

Tyr Asp His Phe Gly Tyr Asp His Phe
1               5

<210> SEQ ID NO 79
<211> LENGTH: 7
<212> TYPE: PRT
<213> ORGANISM: Artificial Sequence
<220> FEATURE:
<223> OTHER INFORMATION: Therapeutic agent
<220> FEATURE:
<221> NAME/KEY: MISC_FEATURE
<222> LOCATION: (1)..(7)
<223> OTHER INFORMATION: D or L amino acid configuration not specified.
      Both configurations encompassed.
<220> FEATURE:
<221> NAME/KEY: MOD_RES
<222> LOCATION: (1)..(1)
<223> OTHER INFORMATION: benzyloxycarbonyl-Tyr
<220> FEATURE:
<221> NAME/KEY: MOD_RES
<222> LOCATION: (7)..(7)
<223> OTHER INFORMATION: AMIDATION

<400> SEQUENCE: 79

Tyr Asp Phe Gly Tyr Asp Phe
1               5
```

```
<210> SEQ ID NO 80
<211> LENGTH: 9
<212> TYPE: PRT
<213> ORGANISM: Artificial Sequence
<220> FEATURE:
<223> OTHER INFORMATION: therapeutic ageny
<220> FEATURE:
<221> NAME/KEY: MISC_FEATURE
<222> LOCATION: (1)..(9)
<223> OTHER INFORMATION: D or L amino acid configuration not specified.
      Both configurations encompassed.
<220> FEATURE:
<221> NAME/KEY: MOD_RES
<222> LOCATION: (1)..(1)
<223> OTHER INFORMATION: benzyloxycarbonyl-Tyr
<220> FEATURE:
<221> NAME/KEY: MOD_RES
<222> LOCATION: (2)..(2)
<223> OTHER INFORMATION: 4-methyl ester aspartic acid
<220> FEATURE:
<221> NAME/KEY: MOD_RES
<222> LOCATION: (7)..(7)
<223> OTHER INFORMATION: 4-methyl ester aspartic acid
<220> FEATURE:
<221> NAME/KEY: MOD_RES
<222> LOCATION: (9)..(9)
<223> OTHER INFORMATION: AMIDATION

<400> SEQUENCE: 80

Tyr Asp His Phe Gly Tyr Asp His Phe
1               5

<210> SEQ ID NO 81
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MISC_FEATURE
<222> LOCATION: (1)..(4)
<223> OTHER INFORMATION: residues 1 to 4 are D-amino acids
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: AMIDATION

<400> SEQUENCE: 81

Tyr Asp His Gln
1

<210> SEQ ID NO 82
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MISC_FEATURE
<222> LOCATION: (1)..(4)
<223> OTHER INFORMATION: residues 1 to 4 are D-amino acids
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: AMIDATION
```

```
<400> SEQUENCE: 82

Tyr Asp His Ala
1

<210> SEQ ID NO 83
<211> LENGTH: 4
<212> TYPE: PRT
<213> ORGANISM: Artificial sequence
<220> FEATURE:
<223> OTHER INFORMATION: Therapeutic agent
<220> FEATURE:
<221> NAME/KEY: MISC_FEATURE
<222> LOCATION: (1)..(4)
<223> OTHER INFORMATION: residues 1 to 4 are D-amino acids
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: AMIDATION

<400> SEQUENCE: 83

Tyr Glu Lys Trp
1

<210> SEQ ID NO 84
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MISC_FEATURE
<222> LOCATION: (1)..(4)
<223> OTHER INFORMATION: residues 1 to 4 are D-amino acids
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: AMIDATION

<400> SEQUENCE: 84

Tyr Asp Lys Trp
1

<210> SEQ ID NO 85
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: AMIDATION

<400> SEQUENCE: 85

Trp Asp His Phe
1

<210> SEQ ID NO 86
<211> LENGTH: 4
```

```
<212> TYPE: PRT
<213> ORGANISM: Artificial sequence
<220> FEATURE:
<223> OTHER INFORMATION: Therapeutic agent
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: AMIDATION

<400> SEQUENCE: 86

Trp Glu Arg Phe
1

<210> SEQ ID NO 87
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: AMIDATION

<400> SEQUENCE: 87

Trp Asp Arg Phe
1

<210> SEQ ID NO 88
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: AMIDATION

<400> SEQUENCE: 88

Tyr Asp His Trp
1

<210> SEQ ID NO 89
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: AMIDATION

<400> SEQUENCE: 89

Tyr Asp His Trp
```

```
<210> SEQ ID NO 90
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: AMIDATION

<400> SEQUENCE: 90

Tyr Glu His Trp
1

<210> SEQ ID NO 91
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: AMIDATION

<400> SEQUENCE: 91

Trp Asp His Trp
1

<210> SEQ ID NO 92
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: AMIDATION

<400> SEQUENCE: 92

Trp Glu His Trp
1

<210> SEQ ID NO 93
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
```

```
<223> OTHER INFORMATION: AMIDATION

<400> SEQUENCE: 93

Tyr Asp Arg Trp
1

<210> SEQ ID NO 94
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: AMIDATION

<400> SEQUENCE: 94

Tyr Asp Lys Trp
1

<210> SEQ ID NO 95
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: AMIDATION

<400> SEQUENCE: 95

Tyr Glu Lys Trp
1

<210> SEQ ID NO 96
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: AMIDATION

<400> SEQUENCE: 96

Tyr Glu Arg Trp
1

<210> SEQ ID NO 97
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MOD_RES
```

```
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: AMIDATION

<400> SEQUENCE: 97

Trp Glu Lys Trp
1

<210> SEQ ID NO 98
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: AMIDATION

<400> SEQUENCE: 98

Trp Glu Arg Trp
1

<210> SEQ ID NO 99
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: AMIDATION

<400> SEQUENCE: 99

Trp Asp Lys Trp
1

<210> SEQ ID NO 100
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: AMIDATION

<400> SEQUENCE: 100

Trp Asp Arg Trp
1

<210> SEQ ID NO 101
<211> LENGTH: 4
<212> TYPE: PRT
```

```
<213> ORGANISM: Artificial Sequence
<220> FEATURE:
<223> OTHER INFORMATION: Therapeutic agent
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: AMIDATION

<400> SEQUENCE: 101

Tyr Asp His Gln
 1

<210> SEQ ID NO 102
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: AMIDATION

<400> SEQUENCE: 102

Ala Glu Arg Phe
 1

<210> SEQ ID NO 103
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: AMIDATION

<400> SEQUENCE: 103

Tyr Ala Arg Phe
 1

<210> SEQ ID NO 104
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: AMIDATION

<400> SEQUENCE: 104

Tyr Glu Ala Phe
 1
```

```
<210> SEQ ID NO 105
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: AMIDATION

<400> SEQUENCE: 105

Tyr Glu Arg Ala
1

<210> SEQ ID NO 106
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: AMIDATION

<400> SEQUENCE: 106

Pro Glu Arg Phe
1

<210> SEQ ID NO 107
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: AMIDATION

<400> SEQUENCE: 107

Tyr Glu Pro Phe
1

<210> SEQ ID NO 108
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: AMIDATION
```

```
<400> SEQUENCE: 108

Tyr Pro Arg Phe
1

<210> SEQ ID NO 109
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: AMIDATION

<400> SEQUENCE: 109

Tyr Glu Arg Pro
1

<210> SEQ ID NO 110
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MOD_RES
<222> LOCATION: (1)..(1)
<223> OTHER INFORMATION: benzoic acid-Tyr
<220> FEATURE:
<221> NAME/KEY: MOD_RES
<222> LOCATION: (4)..(4)
<223> OTHER INFORMATION: AMIDATION

<400> SEQUENCE: 110

Tyr Asp His Gln
1

<210> SEQ ID NO 111
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MOD_RES
<222> LOCATION: (1)..(1)
<223> OTHER INFORMATION: benzyloxycarbonyl-Tyr
<220> FEATURE:
<221> NAME/KEY: MOD_RES
<222> LOCATION: (2)..(2)
<223> OTHER INFORMATION: 4-methyl ester aspartic acid (Asp(OMe))
<220> FEATURE:
<221> NAME/KEY: MOD_RES
<222> LOCATION: (4)..(4)
<223> OTHER INFORMATION: AMIDATION

<400> SEQUENCE: 111

Tyr Asp His Gln
1

<210> SEQ ID NO 112
<211> LENGTH: 4
<212> TYPE: PRT
<213> ORGANISM: Artificial Sequence
<220> FEATURE:
```

```
<223> OTHER INFORMATION: Therapeutic agent
<220> FEATURE:
<221> NAME/KEY: MOD_RES
<222> LOCATION: (1)..(1)
<223> OTHER INFORMATION: 2-Chlorobenzyloxycarbonyl-Tyr
<220> FEATURE:
<221> NAME/KEY: MOD_RES
<222> LOCATION: (4)..(4)
<223> OTHER INFORMATION: AMIDATION

<400> SEQUENCE: 112

Tyr Glu Arg Phe
1

<210> SEQ ID NO 113
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MOD_RES
<222> LOCATION: (1)..(1)
<223> OTHER INFORMATION: 2-Chlorobenzyloxycarbonyl-Tyr
<220> FEATURE:
<221> NAME/KEY: MOD_RES
<222> LOCATION: (4)..(4)
<223> OTHER INFORMATION: AMIDATION

<400> SEQUENCE: 113

Tyr Asp His Phe
1

<210> SEQ ID NO 114
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MOD_RES
<222> LOCATION: (1)..(1)
<223> OTHER INFORMATION: 2-Chlorobenzyloxycarbonyl-Tyr
<220> FEATURE:
<221> NAME/KEY: MOD_RES
<222> LOCATION: (4)..(4)
<223> OTHER INFORMATION: AMIDATION

<400> SEQUENCE: 114

Tyr Asp His Gln
1

<210> SEQ ID NO 115
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MOD_RES
<222> LOCATION: (4)..(4)
<223> OTHER INFORMATION: AMIDATION
<220> FEATURE:
<221> NAME/KEY: MOD_RES
<222> LOCATION: (4)..(4)
<223> OTHER INFORMATION: (3-Methoxy,4-hydroxy-benzoyl)-Tyr

<400> SEQUENCE: 115

Tyr Asp His Gln
1
```

```
<210> SEQ ID NO 116
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MOD_RES
<222> LOCATION: (1)..(1)
<223> OTHER INFORMATION: (3-Methoxy,4-hydroxy-benzoyl)-Tyr
<220> FEATURE:
<221> NAME/KEY: MOD_RES
<222> LOCATION: (4)..(4)
<223> OTHER INFORMATION: AMIDATION

<400> SEQUENCE: 116

Tyr Asp Phe Gln
1

<210> SEQ ID NO 117
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: AMIDATION

<400> SEQUENCE: 117

Tyr Tyr Arg Phe
1

<210> SEQ ID NO 118
<211> LENGTH: 5
<212> TYPE: PRT
<213> ORGANISM: Artificial Sequence
<220> FEATURE:
<223> OTHER INFORMATION: Therapeutic agent
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (5)..(5)
<223> OTHER INFORMATION: AMIDATION

<400> SEQUENCE: 118

Tyr Tyr Glu Arg Phe
1               5

<210> SEQ ID NO 119
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: AMIDATION

<400> SEQUENCE: 119
```

Tyr Asn Arg Phe
1

<210> SEQ ID NO 120
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MOD_RES
<222> LOCATION: (4)..(4)
<223> OTHER INFORMATION: AMIDATION
<220> FEATURE:
<221> NAME/KEY: MOD_RES
<222> LOCATION: (4)..(4)
<223> OTHER INFORMATION: benzyloxycarbonyl-Tyr

<400> SEQUENCE: 120

Tyr Asn Arg Phe
1

<210> SEQ ID NO 121
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: AMIDATION

<400> SEQUENCE: 121

Tyr Met Arg Phe
1

<210> SEQ ID NO 122
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MOD_RES
<222> LOCATION: (1)..(1)
<223> OTHER INFORMATION: benzyloxycarbonyl-Tyr
<220> FEATURE:
<221> NAME/KEY: MOD_RES
<222> LOCATION: (4)..(4)
<223> OTHER INFORMATION: AMIDATION

<400> SEQUENCE: 122

Tyr Met Arg Phe
1

<210> SEQ ID NO 123
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MOD_RES
<222> LOCATION: (1)..(1)
<223> OTHER INFORMATION: ACETYLATION
<220> FEATURE:

```
<221> NAME/KEY: MOD_RES
<222> LOCATION: (4)..(4)
<223> OTHER INFORMATION: AMIDATION

<400> SEQUENCE: 123

Tyr Asn Arg Phe
1

<210> SEQ ID NO 124
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MOD_RES
<222> LOCATION: (1)..(1)
<223> OTHER INFORMATION: benzyloxycarbonyl-Tyr
<220> FEATURE:
<221> NAME/KEY: MOD_RES
<222> LOCATION: (4)..(4)
<223> OTHER INFORMATION: AMIDATION

<400> SEQUENCE: 124

Tyr Asn Arg Phe
1

<210> SEQ ID NO 125
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: AMIDATION

<400> SEQUENCE: 125

Tyr Leu Arg Phe
1

<210> SEQ ID NO 126
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MOD_RES
<222> LOCATION: (1)..(1)
<223> OTHER INFORMATION: benzyloxycarbonyl-Tyr
<220> FEATURE:
<221> NAME/KEY: MOD_RES
<222> LOCATION: (4)..(4)
<223> OTHER INFORMATION: AMIDATION

<400> SEQUENCE: 126

Tyr Leu Arg Phe
1

<210> SEQ ID NO 127
<211> LENGTH: 4
<212> TYPE: PRT
<213> ORGANISM: Artificial Sequence
<220> FEATURE:
<223> OTHER INFORMATION: Therapeutic agent
```

```
<220> FEATURE:
<221> NAME/KEY: MOD_RES
<222> LOCATION: (1)..(1)
<223> OTHER INFORMATION: benzyloxycarbonyl-Tyr
<220> FEATURE:
<221> NAME/KEY: MOD_RES
<222> LOCATION: (4)..(4)
<223> OTHER INFORMATION: AMIDATION

<400> SEQUENCE: 127

Tyr Asp His Gln
1

<210> SEQ ID NO 128
<211> LENGTH: 5
<212> TYPE: PRT
<213> ORGANISM: Artificial Sequence
<220> FEATURE:
<223> OTHER INFORMATION: Therapeutic agent
<220> FEATURE:
<221> NAME/KEY: MOD_RES
<222> LOCATION: (1)..(1)
<223> OTHER INFORMATION: benzyloxycarbonyl-Tyr
<220> FEATURE:
<221> NAME/KEY: MOD_RES
<222> LOCATION: (5)..(5)
<223> OTHER INFORMATION: AMIDATION

<400> SEQUENCE: 128

Tyr Tyr Asp His Gln
1               5

<210> SEQ ID NO 129

<400> SEQUENCE: 129

000

<210> SEQ ID NO 130

<400> SEQUENCE: 130

000

<210> SEQ ID NO 131

<400> SEQUENCE: 131

000

<210> SEQ ID NO 132

<400> SEQUENCE: 132

000

<210> SEQ ID NO 133

<400> SEQUENCE: 133

000

<210> SEQ ID NO 134

<400> SEQUENCE: 134

000

<210> SEQ ID NO 135
```

<400> SEQUENCE: 135

000

<210> SEQ ID NO 136

<400> SEQUENCE: 136

000

<210> SEQ ID NO 137

<400> SEQUENCE: 137

000

<210> SEQ ID NO 138

<400> SEQUENCE: 138

000

<210> SEQ ID NO 139

<400> SEQUENCE: 139

000

<210> SEQ ID NO 140

<400> SEQUENCE: 140

000

<210> SEQ ID NO 141

<400> SEQUENCE: 141

000

<210> SEQ ID NO 142

<400> SEQUENCE: 142

000

<210> SEQ ID NO 143

<400> SEQUENCE: 143

000

<210> SEQ ID NO 144

<400> SEQUENCE: 144

000

<210> SEQ ID NO 145

<400> SEQUENCE: 145

000

<210> SEQ ID NO 146

<400> SEQUENCE: 146

000

<210> SEQ ID NO 147

<400> SEQUENCE: 147

000

<210> SEQ ID NO 148

<400> SEQUENCE: 148

000

<210> SEQ ID NO 149

<400> SEQUENCE: 149

000

<210> SEQ ID NO 150

<400> SEQUENCE: 150

000

<210> SEQ ID NO 151

<400> SEQUENCE: 151

000

<210> SEQ ID NO 152

<400> SEQUENCE: 152

000

<210> SEQ ID NO 153

<400> SEQUENCE: 153

000

<210> SEQ ID NO 154
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MOD_RES
<222> LOCATION: (4)..(4)
<223> OTHER INFORMATION: AMIDATION
<220> FEATURE:
<221> NAME/KEY: MOD_RES
<222> LOCATION: (4)..(4)
<223> OTHER INFORMATION: benzoic acid-Tyr

<400> SEQUENCE: 154

Tyr Glu Arg Phe
1

<210> SEQ ID NO 155
<211> LENGTH: 4
<212> TYPE: PRT
<213> ORGANISM: Artificial Sequence
<220> FEATURE:

```
<223> OTHER INFORMATION: Therapeutic agent
<220> FEATURE:
<221> NAME/KEY: MOD_RES
<222> LOCATION: (1)..(1)
<223> OTHER INFORMATION: bezoic acid-Tyr
<220> FEATURE:
<221> NAME/KEY: MOD_RES
<222> LOCATION: (4)..(4)
<223> OTHER INFORMATION: AMIDATION

<400> SEQUENCE: 155

Tyr Asp His Phe
1

<210> SEQ ID NO 156
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MOD_RES
<222> LOCATION: (1)..(1)
<223> OTHER INFORMATION: Fmoc(betaAla)2-Gln
<220> FEATURE:
<221> NAME/KEY: MISC_FEATURE
<222> LOCATION: (2)..(4)
<223> OTHER INFORMATION: residues 2, 3 and 4 may be substituted by any
      amino acid
<220> FEATURE:
<221> NAME/KEY: MOD_RES
<222> LOCATION: (4)..(4)
<223> OTHER INFORMATION: AMIDATION

<400> SEQUENCE: 156

Gln Ala Ala Ala
1

<210> SEQ ID NO 157
<211> LENGTH: 4
<212> TYPE: PRT
<213> ORGANISM: Artificial Sequence
<220> FEATURE:
<223> OTHER INFORMATION: therapeutic agent
<220> FEATURE:
<221> NAME/KEY: MOD_RES
<222> LOCATION: (1)..(1)
<223> OTHER INFORMATION: Fmoc(betaAla)2-Ser
<220> FEATURE:
<221> NAME/KEY: MISC_FEATURE
<222> LOCATION: (2)..(4)
<223> OTHER INFORMATION: residues 2, 3 and 4 may be substituted by any
      amino acid
<220> FEATURE:
<221> NAME/KEY: MOD_RES
<222> LOCATION: (4)..(4)
<223> OTHER INFORMATION: AMIDATION

<400> SEQUENCE: 157

Ser Ala Ala Ala
1

<210> SEQ ID NO 158
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MOD_RES
<222> LOCATION: (1)..(1)
<223> OTHER INFORMATION: Fmoc(betaAla)2-Arg
<220> FEATURE:
```

```
<221> NAME/KEY: MISC_FEATURE
<222> LOCATION: (2)..(4)
<223> OTHER INFORMATION: residues 2, 3 and 4 may be substituted by any
      amino acid
<220> FEATURE:
<221> NAME/KEY: MOD_RES
<222> LOCATION: (4)..(4)
<223> OTHER INFORMATION: AMIDATION

<400> SEQUENCE: 158

Arg Ala Ala Ala
1

<210> SEQ ID NO 159
<211> LENGTH: 4
<212> TYPE: PRT
<213> ORGANISM: Artificial Sequence
<220> FEATURE:
<223> OTHER INFORMATION: therapeutic agent
<220> FEATURE:
<221> NAME/KEY: MOD_RES
<222> LOCATION: (1)..(1)
<223> OTHER INFORMATION: Fmoc(betaAla)2-Ala
<220> FEATURE:
<221> NAME/KEY: misc_feature
<222> LOCATION: (2)..(4)
<223> OTHER INFORMATION: residues 2, 3 and 4 may be substituted by any
      naturally occurring amino acid
<220> FEATURE:
<221> NAME/KEY: MOD_RES
<222> LOCATION: (4)..(4)
<223> OTHER INFORMATION: AMIDATION

<400> SEQUENCE: 159

Ala Ala Ala Ala
1

<210> SEQ ID NO 160
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MOD_RES
<222> LOCATION: (1)..(1)
<223> OTHER INFORMATION: Fmoc(betaAla)2-Tyr
<220> FEATURE:
<221> NAME/KEY: MISC_FEATURE
<222> LOCATION: (2)..(4)
<223> OTHER INFORMATION: residues 2, 3 and 4 may be substituated by any
      amino acid
<220> FEATURE:
<221> NAME/KEY: MOD_RES
<222> LOCATION: (4)..(4)
<223> OTHER INFORMATION: AMIDATION

<400> SEQUENCE: 160

Tyr Ala Ala Ala
1

<210> SEQ ID NO 161
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MOD_RES
<222> LOCATION: (1)..(1)
<223> OTHER INFORMATION: Fmoc(betaAla)2-Pro
<220> FEATURE:
<221> NAME/KEY: MISC_FEATURE
```

```
<222> LOCATION: (2)..(4)
<223> OTHER INFORMATION: residues 2, 3 and 4 may be substituted by any
      amino acid
<220> FEATURE:
<221> NAME/KEY: MOD_RES
<222> LOCATION: (4)..(4)
<223> OTHER INFORMATION: AMIDATION

<400> SEQUENCE: 161

Pro Ala Ala Ala
1

<210> SEQ ID NO 162
<211> LENGTH: 4
<212> TYPE: PRT
<213> ORGANISM: Artificial Sequence
<220> FEATURE:
<223> OTHER INFORMATION: therapeutic agent
<220> FEATURE:
<221> NAME/KEY: MOD_RES
<222> LOCATION: (1)..(1)
<223> OTHER INFORMATION: Fmoc(betaAla)2-Met
<220> FEATURE:
<221> NAME/KEY: MISC_FEATURE
<222> LOCATION: (2)..(4)
<223> OTHER INFORMATION: residues 2, 3 and 4 may be substituted by any
      amino acid
<220> FEATURE:
<221> NAME/KEY: MOD_RES
<222> LOCATION: (4)..(4)
<223> OTHER INFORMATION: AMIDATION

<400> SEQUENCE: 162

Met Ala Ala Ala
1

<210> SEQ ID NO 163
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MOD_RES
<222> LOCATION: (1)..(1)
<223> OTHER INFORMATION: Fmoc(betaAla)2-
<220> FEATURE:
<221> NAME/KEY: MISC_FEATURE
<222> LOCATION: (2)..(4)
<223> OTHER INFORMATION: residues 2, 3 and 4 may be substituted by any
      amino acid
<220> FEATURE:
<221> NAME/KEY: MOD_RES
<222> LOCATION: (4)..(4)
<223> OTHER INFORMATION: AMIDATION

<400> SEQUENCE: 163

Cys Ala Ala Ala
1

<210> SEQ ID NO 164
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MOD_RES
<222> LOCATION: (1)..(1)
<223> OTHER INFORMATION: Fmoc(betaAla)2-
<220> FEATURE:
<221> NAME/KEY: MOD_RES
<222> LOCATION: (1)..(1)
```

<223> OTHER INFORMATION: Fmoc(betaAla)2-Pha
<220> FEATURE:
<221> NAME/KEY: MISC_FEATURE
<222> LOCATION: (2)..(4)
<223> OTHER INFORMATION: residues 2, 3 and 4 may be substituted by any
      amino acid
<220> FEATURE:
<221> NAME/KEY: MOD_RES
<222> LOCATION: (4)..(4)
<223> OTHER INFORMATION: AMIDATION

<400> SEQUENCE: 164

Phe Ala Ala Ala
1

<210> SEQ ID NO 165
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MOD_RES
<222> LOCATION: (1)..(1)
<223> OTHER INFORMATION: Fmoc(betaAla)2-Tyr
<220> FEATURE:
<221> NAME/KEY: MOD_RES
<222> LOCATION: (4)..(4)
<223> OTHER INFORMATION: AMIDATION

<400> SEQUENCE: 165

Tyr Asp His Gln
1

<210> SEQ ID NO 166
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MOD_RES
<222> LOCATION: (1)..(1)
<223> OTHER INFORMATION: Fmoc(betaAla)2-Leu
<220> FEATURE:
<221> NAME/KEY: MISC_FEATURE
<222> LOCATION: (2)..(4)
<223> OTHER INFORMATION: residues 2, 3 and 4 may be substituted by any
      amino acid
<220> FEATURE:
<221> NAME/KEY: MOD_RES
<222> LOCATION: (4)..(4)
<223> OTHER INFORMATION: AMIDATION

<400> SEQUENCE: 166

Leu Ala Ala Ala
1

<210> SEQ ID NO 167
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MOD_RES
<222> LOCATION: (1)..(1)
<223> OTHER INFORMATION: Fmoc(betaAla)2-His
<220> FEATURE:
<221> NAME/KEY: MISC_FEATURE
<222> LOCATION: (2)..(4)
<223> OTHER INFORMATION: residues 2, 3 and 4 may be substituted by any
      amino acid

```
<220> FEATURE:
<221> NAME/KEY: MOD_RES
<222> LOCATION: (4)..(4)
<223> OTHER INFORMATION: AMIDATION

<400> SEQUENCE: 167

His Ala Ala Ala
1

<210> SEQ ID NO 168
<211> LENGTH: 4
<212> TYPE: PRT
<213> ORGANISM: Artificial Sequence
<220> FEATURE:
<223> OTHER INFORMATION: therapeutic agent
<220> FEATURE:
<221> NAME/KEY: MOD_RES
<222> LOCATION: (1)..(1)
<223> OTHER INFORMATION: Fmoc(betaAla)2-Asp
<220> FEATURE:
<221> NAME/KEY: misc_feature
<222> LOCATION: (2)..(4)
<223> OTHER INFORMATION: residues 2, 3 and 4 may be substituted by any
      naturally ocuring amino acid
<220> FEATURE:
<221> NAME/KEY: MOD_RES
<222> LOCATION: (4)..(4)
<223> OTHER INFORMATION: AMIDATION

<400> SEQUENCE: 168

Asp Ala Ala Ala
1

<210> SEQ ID NO 169
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MOD_RES
<222> LOCATION: (1)..(1)
<223> OTHER INFORMATION: Fmoc(betaAla)2-Tyr
<220> FEATURE:
<221> NAME/KEY: MISC_FEATURE
<222> LOCATION: (3)..(4)
<223> OTHER INFORMATION: residues 3 and 4 may be substituted by any
      amino acid
<220> FEATURE:
<221> NAME/KEY: MOD_RES
<222> LOCATION: (4)..(4)
<223> OTHER INFORMATION: AMIDATION

<400> SEQUENCE: 169

Tyr Ser Ala Ala
1

<210> SEQ ID NO 170
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MOD_RES
<222> LOCATION: (1)..(1)
<223> OTHER INFORMATION: Fmoc(betaAla)2-Tyr
<220> FEATURE:
<221> NAME/KEY: MISC_FEATURE
<222> LOCATION: (3)..(4)
<223> OTHER INFORMATION: residues 3 and 4 may be substituted by any
      amino acid
<220> FEATURE:
```

<221> NAME/KEY: MOD_RES
<222> LOCATION: (4)..(4)
<223> OTHER INFORMATION: AMIDATION

<400> SEQUENCE: 170

Tyr Arg Ala Ala
1

<210> SEQ ID NO 171
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MOD_RES
<222> LOCATION: (1)..(1)
<223> OTHER INFORMATION: Fmoc(betaAla)2-Tyr
<220> FEATURE:
<221> NAME/KEY: MISC_FEATURE
<222> LOCATION: (3)..(4)
<223> OTHER INFORMATION: residues 3 and 4 may be substituted by any
      amino acid
<220> FEATURE:
<221> NAME/KEY: MOD_RES
<222> LOCATION: (4)..(4)
<223> OTHER INFORMATION: AMIDATION

<400> SEQUENCE: 171

Tyr Ala Ala Ala
1

<210> SEQ ID NO 172
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MOD_RES
<222> LOCATION: (1)..(1)
<223> OTHER INFORMATION: Fmoc(betaAla)2-Tyr
<220> FEATURE:
<221> NAME/KEY: MISC_FEATURE
<222> LOCATION: (3)..(4)
<223> OTHER INFORMATION: residues 3 and 4 may be substituted by any
      amino acid
<220> FEATURE:
<221> NAME/KEY: MOD_RES
<222> LOCATION: (4)..(4)
<223> OTHER INFORMATION: AMIDATION

<400> SEQUENCE: 172

Tyr Tyr Ala Ala
1

<210> SEQ ID NO 173
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MOD_RES
<222> LOCATION: (1)..(1)
<223> OTHER INFORMATION: Fmoc(betaAla)2-Tyr
<220> FEATURE:
<221> NAME/KEY: MISC_FEATURE
<222> LOCATION: (3)..(4)
<223> OTHER INFORMATION: residues 3 and 4 may be substituted by any
      amino acid
<220> FEATURE:
<221> NAME/KEY: MOD_RES

<222> LOCATION: (4)..(4)
<223> OTHER INFORMATION: AMIDATION

<400> SEQUENCE: 173

Tyr Pro Ala Ala
1

<210> SEQ ID NO 174
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MOD_RES
<222> LOCATION: (1)..(1)
<223> OTHER INFORMATION: Fmoc(betaAla)2-Tyr
<220> FEATURE:
<221> NAME/KEY: MISC_FEATURE
<222> LOCATION: (3)..(4)
<223> OTHER INFORMATION: residues 3 and 4 may be substituted by any
      amino acid
<220> FEATURE:
<221> NAME/KEY: MOD_RES
<222> LOCATION: (4)..(4)
<223> OTHER INFORMATION: AMIDATION

<400> SEQUENCE: 174

Tyr Met Ala Ala
1

<210> SEQ ID NO 175
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MOD_RES
<222> LOCATION: (1)..(1)
<223> OTHER INFORMATION: Fmoc(betaAla)2-Tyr
<220> FEATURE:
<221> NAME/KEY: MISC_FEATURE
<222> LOCATION: (3)..(4)
<223> OTHER INFORMATION: residues 3 and 4 may be substituted by any
      amino acid
<220> FEATURE:
<221> NAME/KEY: MOD_RES
<222> LOCATION: (4)..(4)
<223> OTHER INFORMATION: AMIDATION

<400> SEQUENCE: 175

Tyr Cys Ala Ala
1

<210> SEQ ID NO 176
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MOD_RES
<222> LOCATION: (1)..(1)
<223> OTHER INFORMATION: Fmoc(betaAla)2-Tyr
<220> FEATURE:
<221> NAME/KEY: MISC_FEATURE
<222> LOCATION: (3)..(4)
<223> OTHER INFORMATION: residues 3 and 4 may be substituted by any
      amino acid
<220> FEATURE:
<221> NAME/KEY: MOD_RES
<222> LOCATION: (4)..(4)

<223> OTHER INFORMATION: AMIDATION

<400> SEQUENCE: 176

Tyr Phe Ala Ala
1

<210> SEQ ID NO 177
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MOD_RES
<222> LOCATION: (1)..(1)
<223> OTHER INFORMATION: Fmoc(betaAla)2-Tyr
<220> FEATURE:
<221> NAME/KEY: MISC_FEATURE
<222> LOCATION: (3)..(4)
<223> OTHER INFORMATION: residues 3 and 4 may be substituted by any
    amino acid
<220> FEATURE:
<221> NAME/KEY: MOD_RES
<222> LOCATION: (4)..(4)
<223> OTHER INFORMATION: AMIDATION

<400> SEQUENCE: 177

Tyr Leu Ala Ala
1

<210> SEQ ID NO 178
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MOD_RES
<222> LOCATION: (1)..(1)
<223> OTHER INFORMATION: Fmoc(betaAla)2-Tyr
<220> FEATURE:
<221> NAME/KEY: MISC_FEATURE
<222> LOCATION: (3)..(4)
<223> OTHER INFORMATION: residues 3 and 4 may be substituted by any
    amino acid
<220> FEATURE:
<221> NAME/KEY: MOD_RES
<222> LOCATION: (4)..(4)
<223> OTHER INFORMATION: AMIDATION

<400> SEQUENCE: 178

Tyr His Ala Ala
1

<210> SEQ ID NO 179
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MOD_RES
<222> LOCATION: (1)..(1)
<223> OTHER INFORMATION: Fmoc(betaAla)2-Tyr
<220> FEATURE:
<221> NAME/KEY: MISC_FEATURE
<222> LOCATION: (3)..(4)
<223> OTHER INFORMATION: residues 3 and 4 may be substituted by any
    amino acid
<220> FEATURE:
<221> NAME/KEY: MOD_RES
<222> LOCATION: (4)..(4)
<223> OTHER INFORMATION: AMIDATION

```
<400> SEQUENCE: 179

Tyr Asp Ala Ala
1

<210> SEQ ID NO 180
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MOD_RES
<222> LOCATION: (1)..(1)
<223> OTHER INFORMATION: Fmoc(betaAla)2-Tyr
<220> FEATURE:
<221> NAME/KEY: MOD_RES
<222> LOCATION: (4)..(4)
<223> OTHER INFORMATION: AMIDATION
<220> FEATURE:
<221> NAME/KEY: MISC_FEATURE
<222> LOCATION: (4)..(4)
<223> OTHER INFORMATION: residue 4 may be substituted by any amino acid

<400> SEQUENCE: 180

Tyr Asp Gln Ala
1

<210> SEQ ID NO 181
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MOD_RES
<222> LOCATION: (1)..(1)
<223> OTHER INFORMATION: Fmoc(betaAla)2-Tyr
<220> FEATURE:
<221> NAME/KEY: MOD_RES
<222> LOCATION: (4)..(4)
<223> OTHER INFORMATION: AMIDATION
<220> FEATURE:
<221> NAME/KEY: MISC_FEATURE
<222> LOCATION: (4)..(4)
<223> OTHER INFORMATION: residue 4 may be substituted by any amino acid

<400> SEQUENCE: 181

Tyr Asp Ser Ala
1

<210> SEQ ID NO 182
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MOD_RES
<222> LOCATION: (1)..(1)
<223> OTHER INFORMATION: Fmoc(betaAla)2-Tyr
<220> FEATURE:
<221> NAME/KEY: MOD_RES
<222> LOCATION: (4)..(4)
<223> OTHER INFORMATION: AMIDATION
<220> FEATURE:
<221> NAME/KEY: MISC_FEATURE
<222> LOCATION: (4)..(4)
<223> OTHER INFORMATION: residue 4 may be substituted by any amino acid

<400> SEQUENCE: 182

Thr Asp Arg Ala
```

```
<210> SEQ ID NO 183
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MOD_RES
<222> LOCATION: (1)..(1)
<223> OTHER INFORMATION: Fmoc(betaAla)2-Tyr
<220> FEATURE:
<221> NAME/KEY: MOD_RES
<222> LOCATION: (4)..(4)
<223> OTHER INFORMATION: AMIDATION
<220> FEATURE:
<221> NAME/KEY: MISC_FEATURE
<222> LOCATION: (4)..(4)
<223> OTHER INFORMATION: residue 4 may be substituted by any amino acid

<400> SEQUENCE: 183

Tyr Asp Ala Ala
1

<210> SEQ ID NO 184
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MOD_RES
<222> LOCATION: (1)..(1)
<223> OTHER INFORMATION: Fmoc(betaAla)2-Tyr
<220> FEATURE:
<221> NAME/KEY: MOD_RES
<222> LOCATION: (4)..(4)
<223> OTHER INFORMATION: AMIDATION
<220> FEATURE:
<221> NAME/KEY: MISC_FEATURE
<222> LOCATION: (4)..(4)
<223> OTHER INFORMATION: residue 4 may be substituted by any amino acid

<400> SEQUENCE: 184

Tyr Asp Tyr Ala
1

<210> SEQ ID NO 185
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MOD_RES
<222> LOCATION: (1)..(1)
<223> OTHER INFORMATION: Fmoc(betaAla)2-Tyr
<220> FEATURE:
<221> NAME/KEY: MOD_RES
<222> LOCATION: (4)..(4)
<223> OTHER INFORMATION: AMIDATION
<220> FEATURE:
<221> NAME/KEY: MISC_FEATURE
<222> LOCATION: (4)..(4)
<223> OTHER INFORMATION: residue 4 may be substituted by any amino acid

<400> SEQUENCE: 185

Tyr Asp Pro Ala
1

<210> SEQ ID NO 186
```

```
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MOD_RES
<222> LOCATION: (1)..(1)
<223> OTHER INFORMATION: Fmoc(betaAla)2-Tyr
<220> FEATURE:
<221> NAME/KEY: MOD_RES
<222> LOCATION: (4)..(4)
<223> OTHER INFORMATION: AMIDATION
<220> FEATURE:
<221> NAME/KEY: MISC_FEATURE
<222> LOCATION: (4)..(4)
<223> OTHER INFORMATION: residue 4 may be substituted by any amino acid

<400> SEQUENCE: 186

Tyr Asp Met Ala
1

<210> SEQ ID NO 187
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MOD_RES
<222> LOCATION: (1)..(1)
<223> OTHER INFORMATION: Fmoc(betaAla)2-Tyr
<220> FEATURE:
<221> NAME/KEY: MOD_RES
<222> LOCATION: (4)..(4)
<223> OTHER INFORMATION: AMIDATION
<220> FEATURE:
<221> NAME/KEY: MISC_FEATURE
<222> LOCATION: (4)..(4)
<223> OTHER INFORMATION: Xaa is any amino acid

<400> SEQUENCE: 187

Tyr Asp Cys Xaa
1

<210> SEQ ID NO 188
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MOD_RES
<222> LOCATION: (1)..(1)
<223> OTHER INFORMATION: Fmoc(betaAla)2-Tyr
<220> FEATURE:
<221> NAME/KEY: MOD_RES
<222> LOCATION: (4)..(4)
<223> OTHER INFORMATION: AMIDATION
<220> FEATURE:
<221> NAME/KEY: MISC_FEATURE
<222> LOCATION: (4)..(4)
<223> OTHER INFORMATION: residue 4 may be substituted by any amino acid

<400> SEQUENCE: 188

Tyr Asp Phe Ala
1

<210> SEQ ID NO 189
<211> LENGTH: 4
<212> TYPE: PRT
<213> ORGANISM: Artificial Sequence
<220> FEATURE:
```

```
<223> OTHER INFORMATION: Therapeutic agent
<220> FEATURE:
<221> NAME/KEY: MOD_RES
<222> LOCATION: (1)..(1)
<223> OTHER INFORMATION: Fmoc(betaAla)2-Tyr
<220> FEATURE:
<221> NAME/KEY: MOD_RES
<222> LOCATION: (4)..(4)
<223> OTHER INFORMATION: AMIDATION
<220> FEATURE:
<221> NAME/KEY: MISC_FEATURE
<222> LOCATION: (4)..(4)
<223> OTHER INFORMATION: residue 4 may be substituted by any amino acid

<400> SEQUENCE: 189

Tyr Asp Leu Ala
1

<210> SEQ ID NO 190
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MOD_RES
<222> LOCATION: (1)..(1)
<223> OTHER INFORMATION: Fmoc(betaAla)2-Tyr
<220> FEATURE:
<221> NAME/KEY: MOD_RES
<222> LOCATION: (4)..(4)
<223> OTHER INFORMATION: AMIDATION
<220> FEATURE:
<221> NAME/KEY: MISC_FEATURE
<222> LOCATION: (4)..(4)
<223> OTHER INFORMATION: residue 4 may be substituted by any amino acid

<400> SEQUENCE: 190

Tyr Asp His Ala
1

<210> SEQ ID NO 191
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MOD_RES
<222> LOCATION: (1)..(1)
<223> OTHER INFORMATION: Fmoc(betaAla)2-Tyr
<220> FEATURE:
<221> NAME/KEY: MOD_RES
<222> LOCATION: (4)..(4)
<223> OTHER INFORMATION: AMIDATION
<220> FEATURE:
<221> NAME/KEY: MISC_FEATURE
<222> LOCATION: (4)..(4)
<223> OTHER INFORMATION: residue 4 may be substituted by any amino acid

<400> SEQUENCE: 191

Tyr Asp Asp Ala
1

<210> SEQ ID NO 192
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MOD_RES
<222> LOCATION: (1)..(1)
```

```
<223> OTHER INFORMATION: Fmoc(betaAla)2-Tyr
<220> FEATURE:
<221> NAME/KEY: MOD_RES
<222> LOCATION: (4)..(4)
<223> OTHER INFORMATION: AMIDATION

<400> SEQUENCE: 192

Tyr Asp His Gln
1

<210> SEQ ID NO 193
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MOD_RES
<222> LOCATION: (1)..(1)
<223> OTHER INFORMATION: Fmoc(betaAla)2-Tyr
<220> FEATURE:
<221> NAME/KEY: MOD_RES
<222> LOCATION: (4)..(4)
<223> OTHER INFORMATION: AMIDATION

<400> SEQUENCE: 193

Tyr Asp His Ser
1

<210> SEQ ID NO 194
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MOD_RES
<222> LOCATION: (1)..(1)
<223> OTHER INFORMATION: Fmoc(betaAla)2-Tyr
<220> FEATURE:
<221> NAME/KEY: MOD_RES
<222> LOCATION: (4)..(4)
<223> OTHER INFORMATION: AMIDATION

<400> SEQUENCE: 194

Tyr Asp His Arg
1

<210> SEQ ID NO 195
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MOD_RES
<222> LOCATION: (1)..(1)
<223> OTHER INFORMATION: Fmoc(betaAla)2-Tyr
<220> FEATURE:
<221> NAME/KEY: MOD_RES
<222> LOCATION: (4)..(4)
<223> OTHER INFORMATION: AMIDATION

<400> SEQUENCE: 195

Tyr Asp His Ala
1

<210> SEQ ID NO 196
<211> LENGTH: 4
<212> TYPE: PRT
<213> ORGANISM: Artificial Sequence
```

```
<220> FEATURE:
<223> OTHER INFORMATION: Therapeutic agent
<220> FEATURE:
<221> NAME/KEY: MOD_RES
<222> LOCATION: (1)..(1)
<223> OTHER INFORMATION: Fmoc(betaAla)2-Tyr
<220> FEATURE:
<221> NAME/KEY: MOD_RES
<222> LOCATION: (4)..(4)
<223> OTHER INFORMATION: AMIDATION

<400> SEQUENCE: 196

Tyr Asp His Tyr
1

<210> SEQ ID NO 197
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MOD_RES
<222> LOCATION: (1)..(1)
<223> OTHER INFORMATION: Fmoc(betaAla)2-Tyr
<220> FEATURE:
<221> NAME/KEY: MOD_RES
<222> LOCATION: (4)..(4)
<223> OTHER INFORMATION: AMIDATION

<400> SEQUENCE: 197

Tyr Asp His Pro
1

<210> SEQ ID NO 198
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MOD_RES
<222> LOCATION: (1)..(1)
<223> OTHER INFORMATION: Fmoc(betaAla)2-Tyr
<220> FEATURE:
<221> NAME/KEY: MOD_RES
<222> LOCATION: (4)..(4)
<223> OTHER INFORMATION: AMIDATION

<400> SEQUENCE: 198

Tyr Asp His Met
1

<210> SEQ ID NO 199
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MOD_RES
<222> LOCATION: (1)..(1)
<223> OTHER INFORMATION: Fmoc(betaAla)2-Tyr
<220> FEATURE:
<221> NAME/KEY: MOD_RES
<222> LOCATION: (4)..(4)
<223> OTHER INFORMATION: AMIDATION

<400> SEQUENCE: 199

Tyr Asp His Cys
1
```

```
<210> SEQ ID NO 200
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MOD_RES
<222> LOCATION: (1)..(1)
<223> OTHER INFORMATION: Fmoc(betaAla)2-Tyr
<220> FEATURE:
<221> NAME/KEY: MOD_RES
<222> LOCATION: (4)..(4)
<223> OTHER INFORMATION: AMIDATION

<400> SEQUENCE: 200

Tyr Asp His Phe
 1

<210> SEQ ID NO 201
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MOD_RES
<222> LOCATION: (1)..(1)
<223> OTHER INFORMATION: Fmoc(betaAla)2-Tyr
<220> FEATURE:
<221> NAME/KEY: MOD_RES
<222> LOCATION: (4)..(4)
<223> OTHER INFORMATION: AMIDATION

<400> SEQUENCE: 201

Tyr Asp His Leu
 1

<210> SEQ ID NO 202
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MOD_RES
<222> LOCATION: (1)..(1)
<223> OTHER INFORMATION: Fmoc(betaAla)2-Tyr
<220> FEATURE:
<221> NAME/KEY: MOD_RES
<222> LOCATION: (4)..(4)
<223> OTHER INFORMATION: AMIDATION

<400> SEQUENCE: 202

Tyr Asp His His
 1

<210> SEQ ID NO 203
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MOD_RES
<222> LOCATION: (1)..(1)
<223> OTHER INFORMATION: Fmoc(betaAla)2-Tyr
<220> FEATURE:
<221> NAME/KEY: MOD_RES
<222> LOCATION: (4)..(4)
<223> OTHER INFORMATION: AMIDATION
```

```
<400> SEQUENCE: 203

Tyr Asp His Asp
1

<210> SEQ ID NO 204
<211> LENGTH: 5
<212> TYPE: PRT
<213> ORGANISM: Artificial Sequence
<220> FEATURE:
<223> OTHER INFORMATION: Therapeutic agent
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (5)..(5)
<223> OTHER INFORMATION: AMIDATION
<220> FEATURE:
<221> NAME/KEY: MOD_RES
<222> LOCATION: (5)..(5)
<223> OTHER INFORMATION: benzyloxycarbonyl-Lys

<400> SEQUENCE: 204

Tyr Glu Arg Phe Lys
1               5

<210> SEQ ID NO 205
<211> LENGTH: 5
<212> TYPE: PRT
<213> ORGANISM: Artificial Sequence
<220> FEATURE:
<223> OTHER INFORMATION: Therapeutic agent
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (5)..(5)
<223> OTHER INFORMATION: benzyloxycarbonyl-Lys
<220> FEATURE:
<221> NAME/KEY: MOD_RES
<222> LOCATION: (5)..(5)
<223> OTHER INFORMATION: AMIDATION

<400> SEQUENCE: 205

Tyr Asp His Phe Lys
1               5

<210> SEQ ID NO 206
<211> LENGTH: 5
<212> TYPE: PRT
<213> ORGANISM: Artificial Sequence
<220> FEATURE:
<223> OTHER INFORMATION: Therapeutic agent
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (5)..(5)
<223> OTHER INFORMATION: AMIDATION
<220> FEATURE:
<221> NAME/KEY: MOD_RES
<222> LOCATION: (5)..(5)
<223> OTHER INFORMATION: benzyloxycarbonyl-Lys

<400> SEQUENCE: 206

Tyr Asp His Gln Lys
1               5
```

```
<210> SEQ ID NO 207

<400> SEQUENCE: 207

000

<210> SEQ ID NO 208
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MISC_FEATURE
<222> LOCATION: (1)..(4)
<223> OTHER INFORMATION: residues 1 - 4 are D amino acids

<400> SEQUENCE: 208

Tyr Glu His Phe
1

<210> SEQ ID NO 209
<211> LENGTH: 4
<212> TYPE: PRT
<213> ORGANISM: Artificial Sequence
<220> FEATURE:
<223> OTHER INFORMATION: therapeutic agent
<220> FEATURE:
<221> NAME/KEY: MISC_FEATURE
<222> LOCATION: (1)..(4)
<223> OTHER INFORMATION: residues 1 - 4 are D amino acids

<400> SEQUENCE: 209

Tyr Asp Lys Phe
1

<210> SEQ ID NO 210
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MISC_FEATURE
<222> LOCATION: (1)..(4)
<223> OTHER INFORMATION: residues 1 - 4 are D amino acids

<400> SEQUENCE: 210

Trp Glu His Phe
1

<210> SEQ ID NO 211
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MISC_FEATURE
<222> LOCATION: (1)..(4)
<223> OTHER INFORMATION: residues 1 - 4 are D amino acids

<400> SEQUENCE: 211

Tyr Glu Lys Phe
1

<210> SEQ ID NO 212
<211> LENGTH: 4
```

```
<212> TYPE: PRT
<213> ORGANISM: Artificial Sequence
<220> FEATURE:
<223> OTHER INFORMATION: Therapeutic agent
<220> FEATURE:
<221> NAME/KEY: MISC_FEATURE
<222> LOCATION: (1)..(4)
<223> OTHER INFORMATION: residues 1 - 4 are D amino acids

<400> SEQUENCE: 212

Trp Glu Lys Phe
1

<210> SEQ ID NO 213
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MISC_FEATURE
<222> LOCATION: (1)..(4)
<223> OTHER INFORMATION: residues 1 - 4 are D amino acids

<400> SEQUENCE: 213

Trp Asp Lys Phe
1

<210> SEQ ID NO 214
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MISC_FEATURE
<222> LOCATION: (1)..(4)
<223> OTHER INFORMATION: residues 1 - 4 are D amino acids

<400> SEQUENCE: 214

Tyr Asp His Trp
1

<210> SEQ ID NO 215
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MISC_FEATURE
<222> LOCATION: (1)..(4)
<223> OTHER INFORMATION: residues 1 - 4 are D amino acids

<400> SEQUENCE: 215

Tyr Glu His Trp
1

<210> SEQ ID NO 216
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MISC_FEATURE
<222> LOCATION: (1)..(4)
<223> OTHER INFORMATION: residues 1 - 4 are D amino acids

<400> SEQUENCE: 216
```

Trp Asp His Trp
1

<210> SEQ ID NO 217
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MISC_FEATURE
<222> LOCATION: (1)..(4)
<223> OTHER INFORMATION: residues 1 - 4 are D amino acids

<400> SEQUENCE: 217

Trp Glu His Trp
1

<210> SEQ ID NO 218
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MISC_FEATURE
<222> LOCATION: (1)..(4)
<223> OTHER INFORMATION: residues 1 - 4 are D amino acids

<400> SEQUENCE: 218

Tyr Asp Asp Trp
1

<210> SEQ ID NO 219
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MISC_FEATURE
<222> LOCATION: (1)..(4)
<223> OTHER INFORMATION: residues 1 - 4 are D amino acids

<400> SEQUENCE: 219

Tyr Asp Lys Trp
1

<210> SEQ ID NO 220
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MISC_FEATURE
<222> LOCATION: (1)..(4)
<223> OTHER INFORMATION: residues 1 - 4 are D amino acids

<400> SEQUENCE: 220

Tyr Glu Lys Trp
1

<210> SEQ ID NO 221
<211> LENGTH: 4
<212> TYPE: PRT
<213> ORGANISM: Artificial Sequence
<220> FEATURE:
<223> OTHER INFORMATION: Therapeutic agent
<220> FEATURE:

```
<221> NAME/KEY: MISC_FEATURE
<222> LOCATION: (1)..(4)
<223> OTHER INFORMATION: residues 1 - 4 are D amino acids

<400> SEQUENCE: 221

Tyr Glu Arg Trp
1

<210> SEQ ID NO 222
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MISC_FEATURE
<222> LOCATION: (1)..(4)
<223> OTHER INFORMATION: residues 1 - 4 are D amino acids

<400> SEQUENCE: 222

Trp Glu Lys Trp
1

<210> SEQ ID NO 223
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MISC_FEATURE
<222> LOCATION: (1)..(4)
<223> OTHER INFORMATION: residues 1 - 4 are D amino acids

<400> SEQUENCE: 223

Trp Glu Arg Trp
1

<210> SEQ ID NO 224
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MISC_FEATURE
<222> LOCATION: (1)..(4)
<223> OTHER INFORMATION: residues 1 - 4 are D amino acids

<400> SEQUENCE: 224

Trp Asp Lys Trp
1

<210> SEQ ID NO 225
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MISC_FEATURE
<222> LOCATION: (1)..(4)
<223> OTHER INFORMATION: residues 1 - 4 are D amino acids

<400> SEQUENCE: 225

Trp Gln Arg Trp
1

<210> SEQ ID NO 226
```

```
<211> LENGTH: 4
<212> TYPE: PRT
<213> ORGANISM: Artificial Sequence
<220> FEATURE:
<223> OTHER INFORMATION: Therapeutic agent
<220> FEATURE:
<221> NAME/KEY: MISC_FEATURE
<222> LOCATION: (1)..(4)
<223> OTHER INFORMATION: residues 1 - 4 are D amino acids

<400> SEQUENCE: 226

Trp Asn Lys Trp
1

<210> SEQ ID NO 227
<211> LENGTH: 5
<212> TYPE: PRT
<213> ORGANISM: Artificial Sequence
<220> FEATURE:
<223> OTHER INFORMATION: cleavable linker

<400> SEQUENCE: 227

Asp Asp Asp Asp Tyr
1               5

<210> SEQ ID NO 228
<211> LENGTH: 5
<212> TYPE: PRT
<213> ORGANISM: Artificial Sequence
<220> FEATURE:
<223> OTHER INFORMATION: cleavable linker

<400> SEQUENCE: 228

His Pro Phe His Leu
1               5
```

METHOD OF DIAGNOSIS AND PROGNOSIS

GOVERNMENT LICENSE RIGHTS

The work leading to this invention was supported in part by National Institutes of Health RO1 Grants CA84040 and CA098583. The government may have certain rights in the invention.

PRIORITY STATEMENT

This application is a national stage application under 35 U.S.C. § 371 of PCT International Application No. PCT/GB2012/050947 which has an International filing date of 27 Apr. 2012 and which claims priority under 35 U.S.C. § 119 to British Application No. 1107118.0 filed 27 Apr. 2011. The contents of the applications recited above are incorporated herein by reference in their entirety.

REFERENCE TO A SEQUENCE LISTING

This application contains references to amino acid sequences and/or nucleic acid sequences which have been submitted concurrently herewith as the sequence listing text file entitled "1960133_1.txt", file size 64 KiloBytes (KB), created on 12 Dec. 2013. The aforementioned sequence listing is hereby incorporated by reference in its entirety pursuant to 37 C.F.R. § 1.52(e)(5).

FIELD OF INVENTION

The invention relates to the diagnosis of cancer and other inflammatory disorder and to the provision of prognostic and theranostic information regarding such disorders.

BACKGROUND OF THE INVENTION

Gadd45β and Cancer

There are a number of cellular pathways involved in carcinogenesis and cancer progression including the c-Jun N-terminal kinase JNK pathway. JNKs are responsive to cytokines and stress stimuli such as ultraviolet irradiation, heat shock and osmotic shock. Also activated in the response to cytokines and cellular stress is the NF-κB pathway. The NF-κB pathway can inhibit the JNK pathway by crosstalk mediated by Gadd45β and the JNK kinase, mitogen activated protein-kinase kinase 7 (MKK7/JNKK2). MKK7 activity is inhibited by Gadd45β, a member of the Gadd45 family of inducible factors and a direct transcriptional target of NF-κB. This means that Gadd45β mediates NF-κB suppression of JNK signalling by binding to MKK7 and inhibiting its activity. Papa, et al. 2004, Nature Cell Biology 6(2):1462153.

The use of NF-κB inhibitors has been proposed for use in the treatment of cancer and inflammatory diseases. However, because NF-κB has a number of activities including roles in programmed cell death (PCD), immunity, inflammation and tissue development, it is preferred to inhibit specific functions of NF-κB rather than NF-κB itself. A number of Gadd45β inhibitors have therefore been proposed (see for example PCT patent application PCT/GB2010/001970).

The present invention relates to the measurement of cellular levels of Gadd45β and is based on the discovery that an indication of Gadd45β levels is useful in both diagnosis of, and the provision of prognostic and theranostic information relating to certain cancers. The present invention is especially related to multiple myeloma and to related cancers.

Multiple myeloma (MM), also known as plasma cell myeloma and Kahler's disease, is a cancer of plasma cells. MM is currently incurable, although temporary remissions can be induced by use of steroids, chemotherapy, thalidomide and stem cell transplants. According to the American Cancer Society, there are approximately 45,000 people in the United States living with multiple myeloma with approximately 15,000 new cases being diagnosed each year in the United States. The average survival time from diagnosis is approximately three years. Multiple myeloma is the second most prevalent blood cancer after non-Hodgkin's lymphoma and represents approximately 1% of all cancers and approximately 2% of all cancer deaths. The incidence of multiple myeloma appears to be increasing and there is also some evidence that the age of onset of the disease is falling. There is a clear need for improved provision of diagnostic, prognostic and theranostic information relating to multiple myeloma to assist in its diagnosis, to assist in providing a patient or physician with prognostic information and to assist in the provision of information useful in selecting patients most likely to respond to a specific treatment.

A number of methods have been proposed for use in providing diagnostic and/or prognostic information relating to multiple myeloma. For example, US 2005/0112630 discloses placing multiple myeloma patients into distinct clinical sub-groups depending on differential expression of a group of genes thought to be involved in normal plasma cell differentiation. US 2009/0264306 discloses the use of DNA methylation profiles for providing diagnostic and prognostic information relating to a number of haematological malignancies. US 2010/0144673 discloses the provision of useful information regarding multiple myeloma prognosis based on expression levels of the CKS1B gene. WO 03/068935 discloses novel RNA and protein antigens present on tumour cell surfaces and proposed for use in treatment, diagnosis and prognosis of a number of malignancies including multiple myeloma. WO 2010/040124 proposes the use of the gene GOLPH3 in diagnosing, prognosing and monitoring cancer including multiple myeloma.

WO 2004/016744 discloses the use of Gadd45β expression in diagnosing or predicting susceptibility to liver disease wherein decreased Gadd45β expression correlates with disease or with an increased risk of disease.

Multiple myeloma is typically diagnosed following the detection of M-protein (monoclonal gamma globulin or paraprotein) in serum and/or urine and the detection of clonal plasma cells in the bone marrow by histopathology. See *Brit. J. Haematol.* (2003) 121:749-757 for a review of the classification of multiple myeloma and other monoclonal gammopathies. The cancerous cells are typically CD138 positive cells and such cells may be detected in the plasma, bone marrow or other tissue (for example, lymph nodes, kidneys, spleen and bone) into which they have infiltrated. Whilst existing methods of diagnosis of multiple myeloma are adequate for many purposes, they do not generally provide reliable prognostic information.

It has been reported (Zenmyo et al. Diagnostic Pathol. (2010:5:69)) that Gadd45β expression falls with cancer progression in chondrosarcoma and also in human hepatocellular sarcoma (Qiu et al. Am. J. Pathol. (2003:162, 1961)).

The present invention is based on the discovery that in respect of cancers of the blood and lymphatic system, Gadd45β expression is indicative of cancer and also poorer prognosis and suitability for treatment with Gadd45β inhibitors.

SUMMARY OF INVENTION

According to a first aspect of the invention there is provided a method of measuring Gadd45β expression comprising the step of measuring Gadd45β expression levels in a sample of cells previously obtained from a subject known to have or suspected of having a haematological malignancy.

According to a second aspect of the invention there is provided a dataset comprising the measured Gadd45β expression levels in cells obtained from a cohort of multiple subjects suspected or known to have a specific haematological malignancy.

Fifty-eight multiple myeloma patients were divided in three groups according to the mRNA value of Gadd45β obtained at diagnosis. Cut-off values were identified using 33rd and 66th percentile, thus dividing the whole population in three subgroups with an equal number of patients with low level, intermediate level and high level of Gadd45β mRNA. Using Kaplan-Meier methods the Progression Free Survival (PFS) was estimated and differences among curves were analysed by the long-rank test.

Results demonstrate a difference in PFS between the low expression and combine intermediate and high expression groups, showing that patients with low Gadd45β mRNA level have a better outcome compared with the other group.

Figure 3:
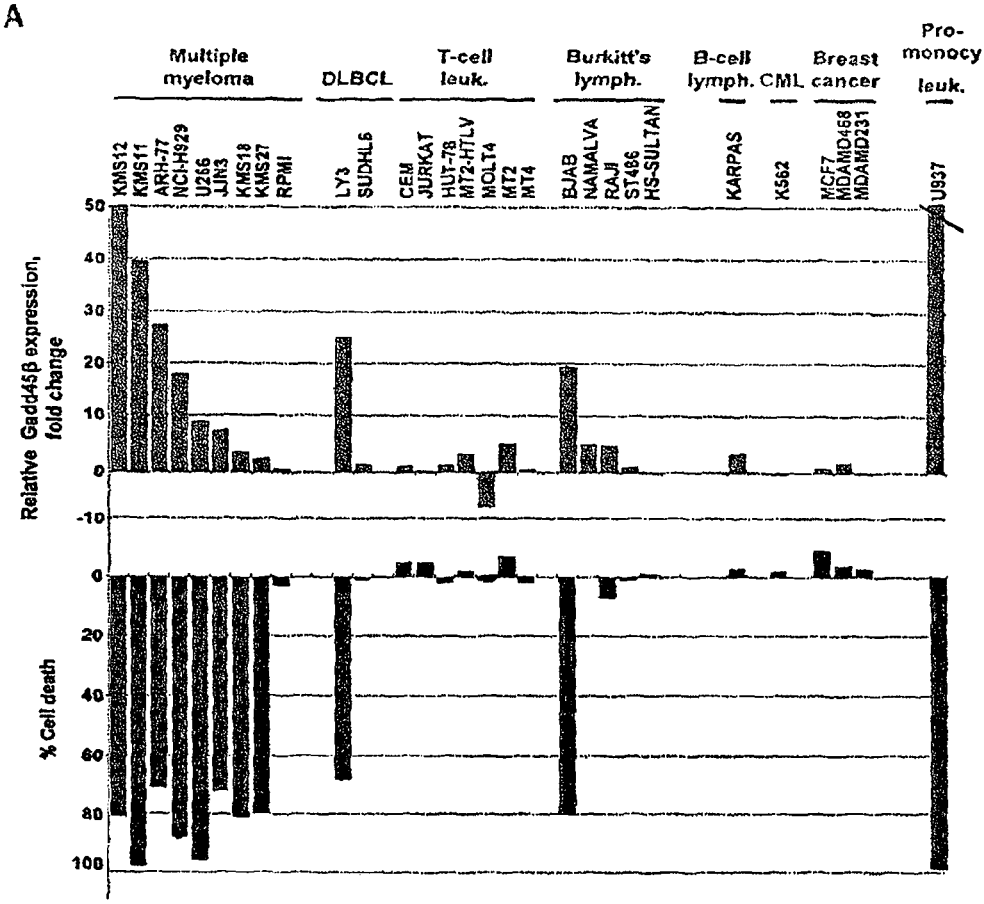
Figure 3:
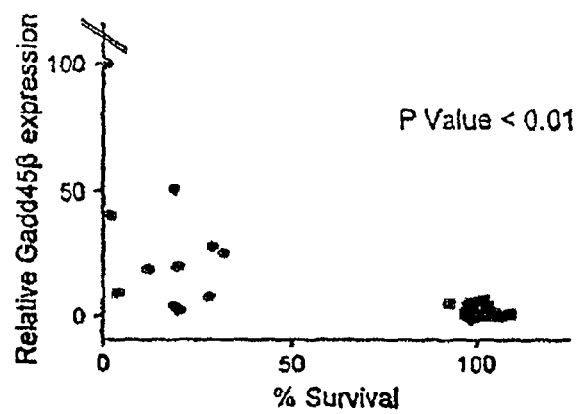

FIG. 3 shows a correlation in tumour cell lines between sensitivity to killing by a Gadd45β inhibitor and levels of Gadd45β expression. (A) Top panel shows the expression of Gadd45β in a panel of 29 cancer cell lines (as measured by qRT-PCR) whereas the bottom panel shows the percentage of cell death in the same cell lines after treatment with 10 μM of the specific Gadd45β inhibitor "Z-DTP2" (a tetrapeptide having the sequence Tyr-Glu-Arg-Phe, with amino acids in the D configuration, and conjugated to an NH$_2$ group at the C terminal and to a benzyloxycarbonyl group at the N terminal) at 10 μM for 144 hours (as measured by [3H] thymidine incorporation). (B) Shows the correlation between Gadd45β expression and cell death. The significance of the correlation co-efficient between the two parameters is p<0.01 (Pearson correlation as calculated by Graph-Pad software).

Figure 4:
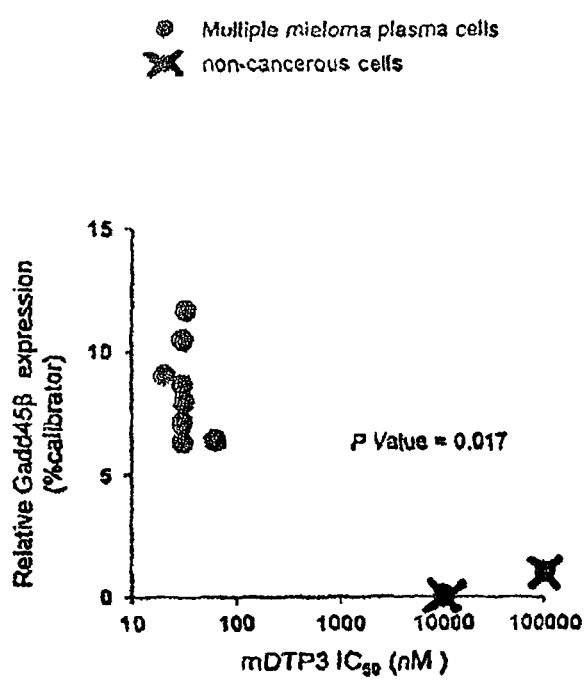

FIG. 4 shows correlation between Gadd45β expression and cytotoxic activity of the Gadd45β/MKK7 inhibitor on mDTP3 in primary haematopoietic cells. (A) The top panel shows the expression of Gadd45β in peripheral blood mononuclear cells (PBMCs) from a healthy volunteer and CD138$^+$ plasma cells from patients suffering from multiple myeloma (MM) (n=9) or Waldenström's macroglobulinemia (WM) (n=2). The bottom panel shows the mean concentrations of compound mDTP3 inducing 50% (IC$_{50}$) cell killing in primary cells. Plasma cells (i.e. CD138$^+$) were purified using anti-CD138$^+$ magnetic microbeads (Miltenyi Biotech GmbH, Germany), and cell purity was verified by flow cytometry. For killing assays, CD138$^+$ plasma cells were treated with increasing concentrations of mDTP3 (i.e. 0.0001, 0.001, 0.003, 0.01, 0.03, 0.1, 0.3, 1, 3 and 10 μM) for 48 hrs. PBMCs were treated with 100 μM of mDTP3 for 144 hrs. IC$_{50}$ values were determined by cell viability assays. Gadd45β expression values were normalized to an endogen control (i.e. 18S ribosomal RNA). Values denote mean±standard deviation. (B) Shown is the correlation plot of Gadd45β expression vs the mDTP3 IC$_{50}$s values. As it can be seen, the absence of mDTP3 cytotoxicity in non-cancerous cells correlates with statistical significance with the low Gadd45β expression in these cells. The significance of the correlation coefficient between the two parameters' domain is high (p=0.017), confirming high target specificity of mDTP3 in primary MM cells.

DETAILED DESCRIPTION OF INVENTION

According to a first aspect of the invention there is provided a method of measuring Gadd45β expression comprising the step of measuring Gadd45β expression levels in a sample of cells obtained from a subject known to have or suspected of having a haematological malignancy.

Haematological Malignancies

Haematological malignancies relating to the invention may be Lymphomas or Leukaemias. According to certain embodiments the invention may relate to haematological malignancies wherein said malignancy is a member of one or more of the following groups:

1. Lymphoma
2. Leukaemia

3. Mature B-cell malignancies
4. Mature T-cell malignancies
5. Mature natural killer cell malignancies
6. Hodgkin's lymphoma
7. Chronic lymphocytic leukaemia
8. Acute lymphocytic leukaemia
9. Chronic myelogenous leukaemia
10. Acute myelogenous leukaemia According to certain preferred embodiments the invention may relate to haematological malignancies falling into one of the following groups:
1. Burkitt's lymphoma, diffuse large B-cell lymphoma (DCBCL) T-cell leukaemia, acute myelogenic leukaemia (AML), acute lymphocytic leukaemia (ACL), multiple myeloma (MM), mantle cell lymphoma, MALT lymphoma, Hodgkin's lymphoma (HL), adult T-cell leukaemia, chronic lymphatic leukaemia (CLL), chronic myeloid leukaemia (CML), cutaneous T-cell lymphoma, myelodysplastic syndrome and pro-monolytic leukaemia.
2. Promonocytic leukaemia, Burkitt's lymphoma, diffuse large B-cell lymphoma (DLBCL), T-cell leukaemia, B-cell leukaemia, multiple myeloma, chronic myeloid leukaemia (CML).
3. Burkitt's lymphoma, diffuse large B-cell lymphoma, multiple myeloma.
4. Diffuse large B-cell lymphoma, multiple myeloma.

According to certain preferred embodiments the invention relates to haematological malignancies associated with increased cellular expression of Gadd45β mRNA.

According to certain preferred embodiments the invention may relate to multiple myeloma.

Sample of Cells

The sample of cells may be obtained from the blood, lymph fluid, lymph node biopsy or bone marrow or from peripheral tissue which has been infiltrated by cancer cells (for example, kidney, spleen or bone, or another tissue known to be infiltrated by cancer cells). According to certain embodiments it is obtained from the bone marrow. The term "sample of cells" includes both live and dead cells, isolated cells and cells present in tissue and also cell-derived material (for example homogenised cells or fluid containing cellular material). The sample preferably contains a material amount of tumour cells or suspected tumour cells but may also contain other cells. That is to say it needs not necessarily be completely purified.

According to certain embodiments the method of the first aspect of the invention includes the step of obtaining the sample of cells. According to other embodiments of the first aspect of the invention, the method does not include the step of obtaining the sample of cells from a subject. That is to say the method is practised on a sample previously obtained from a subject.

The Subject

The subject is preferably a human subject. Accordingly, the specification is preferably to be read in the context of diagnosing, prognosing and treating human subjects.

A subject suspected of having a haematological malignancy may be suspected of having that malignancy because of their manifestation of suggestive or diagnostic symptoms. For example, a subject suspected of having multiple myeloma may have elevated plasma calcium, renal problems or renal failure, anaemia, bone lesions and or bone pain. A subject known to have multiple myeloma may have been diagnosed by the detection of clonal plasma cells or M-protein.

Sample Processing

The sample of cells having been obtained from the subject may be prepared before Gadd45β expression levels are measured. For example, the cells may be disinfected, purified, fixed or preserved. If the sample of cells is a tissue sample, the tissue may be disrupted for example to disaggregate the cells therein. The sample as originally obtained may be enriched for a particular cellular subset. That cellular subset is typically a subset of cancer or suspected cancer cells. Appropriate cell markers may be used to select cellular subsets. In the case of aspects of the invention relating to multiple myeloma, CD138 may be an appropriate cell marker. Any suitable method may be used in select a subset of cells in an enrichment process, for example CD138$^+$ cells may be selected for by a method of cell sorting such as fluorescence-activated cell sorting or magnetic cell sorting. Such methods are also applicable to the selection of cellular subsets using other cell type specific surface markers. Alternatively, cells may be prepared by enriching a cell sample for fast-multiplying cells. Fast multiplying cells may be enriched by culturing the sample in growth medium for a period.

In certain embodiments the cells will need to be disrupted or lysed to allow Gadd45β expression levels to be measured. For example, the cells may be subjected to a nucleic acid or protein extraction and preparation method.

Use of Methods of the Invention in Diagnosis

According to certain embodiments the method of the first aspect of the invention involves the provision of diagnostically useful information. In some cases the method may include a step of making a diagnosis. In other cases the step of making the diagnosis is excluded from the claimed method.

Preferably the measurement of elevated Gadd45β expression (at the nucleic acid, protein or activity level) is indicative of the subject having a haematological malignancy. The haematological malignancy may be as defined above under the heading "haematological malignancies".

In certain embodiments the haematological malignancy is multiple myeloma.

In certain embodiments the method of the invention involves the provision of information useful in the differential diagnosis of multiple myeloma versus another disorder (for example MGUS).

Assessment of Gadd45B Levels

The Gadd45β expression level in a sample of cells may be the mRNA expression level, the protein expression level or the level of Gadd45β protein activity expressed.

Any method may be used to determine the mRNA expression level, for example nucleic acid amplification techniques (for example the various versions of quantitative and semi-quantitative RT-PCR available) or a quantitative or semi-quantitative hybridisation technique.

Any method may be used to determine the protein expression level, for example flow cytometry, western blotting, protein arrays, immunoassays such as RIA and ELISA may be used.

Any method may be used to determine the Gadd45β protein activity expressed, suitable methods include enzyme assays (for example phosphorylation assays) and binding assays.

Gadd45β activity may be measured directly (for example, by measuring its binding activity) or indirectly (for example, by measuring phosphorylation of or activity of mitogen activated protein-kinase kinase 7 (MKK7) which is a cellular signalling protein that is activated by Gadd45β).

Gadd45β expression levels may be measured relatively or absolutely. If absolute expression levels are used, measured values may be compared with threshold values in order to determine if they are elevated. Alternatively, they may be measured relative to levels in a control sample which may be measured at the same time or have been previously measured.

Various control samples may be used including, as non-limiting examples, cell lines (for example levels in a sample taken from a subject suspected or having multiple myeloma may be measured relative to levels in a multiple myeloma cell line (for example U266 and/or relative to a non-multiple myeloma cell line).

Alternatively, the control sample may be obtained from healthy subjects.

Alternatively, the Gadd45β expression levels may be measured relative to other subjects or a cohort of other subjects diagnosed with the haematological malignancy that the subject is suspected as having.

According to certain embodiments the method is for diagnosing a specific haematological malignancy (for example multiple myeloma) if the sample of cells exhibits elevated Gadd45β expression levels when the measured Gadd45β expression level is compared to a dataset comprising corresponding Gadd45β expression levels previously measured in cells obtained from a cohort of one or more further subjects that are healthy. Alternatively, said further subjects may be further subjects that are known to have the specific haematological malignancy (for example multiple myeloma).

Typically, a diagnosis of a haematological malignancy is made when the sample of cells exhibits elevated Gadd45β expression levels relative to a sample obtained from a healthy subject, or when the sample of cells exhibits Gadd45β expression levels comparable to those seen in a sample obtained from a subject known to have the haematological malignancy.

Figure 1:
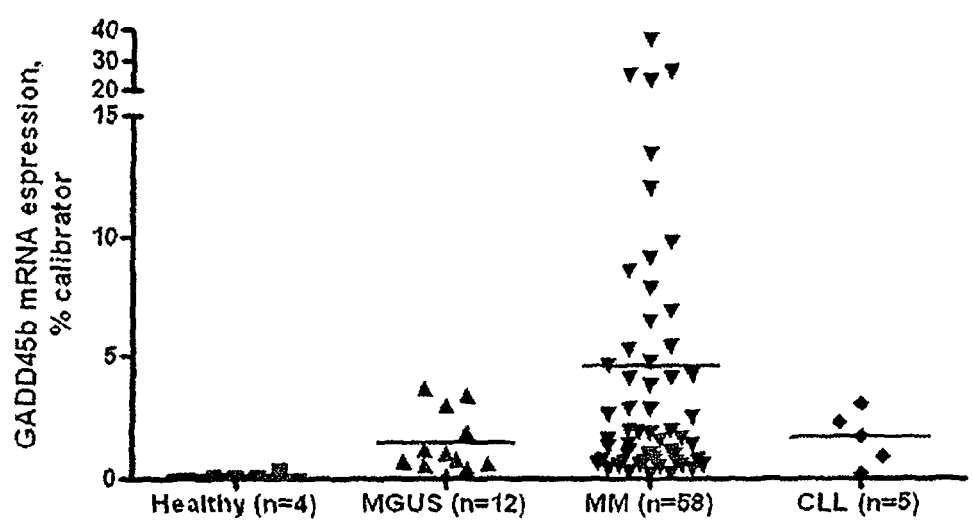
FIG. 1 shows Gadd45β mRNA expression in cells obtained from patients at diagnosis of either MGUS, multiple myeloma (MM) or chronic lymphocytic leukemia (CLL) compared to values obtained from the cells of healthy subjects. Gadd45β mRNA values were calculated from qRT-PCR measurements on 4 samples of purified CD19$^+$ lymphocytes derived from peripheral blood of healthy subjects, 12 samples of purified CD138$^+$ plasma cells obtained from bone marrow aspiration of patients with monoclonal gammopathy of undetermined significance (MGUS), a premalignant situation that can evolve in multiple myeloma with an incidence of 1% each year, 58 samples of purified CD138$^+$ plasma cells obtained from bone marrow aspiration of patients with newly diagnosed multiple myeloma and 5 samples of purified CD19$^+$ lymphocytes obtained from peripheral blood of patients with Chronic Lymphocytic Leukemia (CLL). The comparison of mRNA levels in purified plasma cells of MGUS patients with MM patients was significantly different (p<0.0001). Comparison was performed using the t-student test and a P value below 0.05 was considered significant.

Diagnostic aspects of the invention are illustrated by Example 1 and FIG. 1 which shows that CD138 positive cells taken from patients having multiple myeloma are more likely to show higher Gadd45β expression than are corresponding samples of B-cells or plasma cells (for example CD138$^+$ or CD19 cells) taken from patients having MGUS, CLL and healthy patients.

Use of Methods of the Invention in the Determination of Prognosis

In addition for use in diagnosing a specific haematological malignancy (for example, multiple myeloma), the method of the invention may also be used to give an indication of likely prognosis of a subject already diagnosed with a specific haematological malignancy (wherein said diagnosis was either made by use of a method of the invention or made by another method, for example in the case of multiple myeloma the diagnosis may be made by bone marrow histopathology and/or detection of M-protein in the blood plasma or urine).

Typically, such an approach involves categorising the Gadd45β expression levels, measured in cells obtained from the subject as relatively high or relatively low (for example, by placing the expression into two or more bands) as compared to other subjects previously diagnosed with the same specific haematological malignancy.

For example, the measured Gadd45β expression level may be compared to a dataset comprising corresponding Gadd45β expression levels previously measured in corresponding cells obtained from a cohort of multiple (for example at least 10, 20, 30, 40, 50, 60, 70, 80, 90, 100, 200, 300, 500, 750 or 1000) further subjects wherein said further subjects are known to have the specific haematological malignancy and wherein Gadd45β expression levels are categorised as relatively high or relatively low.

Alternatively, Gadd45β expression levels may be categorised as relatively high or relatively low for a specific malignancy by comparison to reference values of Gadd45β expression for the applicable specific malignancy and appropriate cell type.

The categorisation of Gadd45β expression levels as relatively high or relatively low may be used to predict the prognosis of the subject (for example to provide a prediction of likely survival or progression-free survival or an indication of the likelihood of specific symptoms or severity of symptoms over a forthcoming timescale). Typically a relatively high expression level predicts a relatively poor prognosis and a relatively low expression level predicts a relatively good prognosis.

Figure 2:
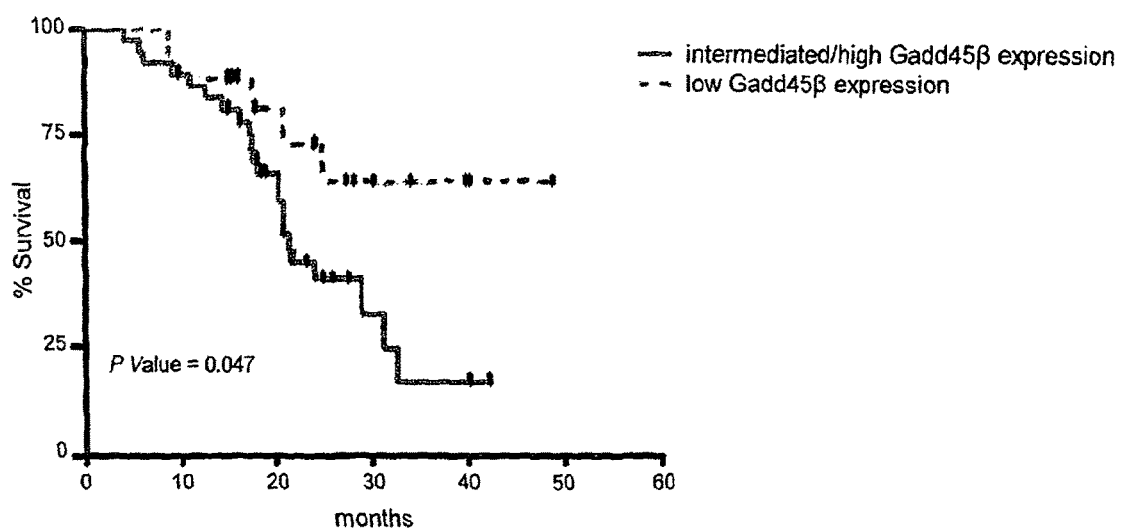
FIG. 2 shows a progression-free survival curve for a cohort of patients suffering from multiple myeloma and being treated with a standard treatment protocol of VMP (velcade-melphalan-prednisone). Patients are segregated as either having low or intermediate/high Gadd45β expression of their CD138$^+$ cells, as measured by qRT-PCR.

Prognostic aspects of the invention are illustrated by reference to Example 2 and FIG. 2, which shows that individual patients found to have relatively high Gadd45β expression on diagnosis with multiple myeloma are more likely to show a worsening of disease during a subsequent follow-up period than patients found to have relatively low Gadd45β expression on diagnosis.

Use of Methods of the Invention in Theranostic Applications

An indication of likely prognosis may be used to select an appropriate treatment for said subjects. In general a more pessimistic prognosis may indicate a more aggressive treatment but there may be circumstances where a poor prognosis combined with relatively ineffective treatments may lead to a decision to offer palliative care only so as to allow the patient to avoid side-effects of a treatment which may do little or nothing by way of reduction of mortality risk.

According to certain embodiments, the method of the invention includes a step of using prognostic information to select an appropriate treatment.

According to certain embodiments, an indication of relatively high Gadd45β expression levels may be used to indicate treatment of the specific haematological malignancy (for example multiple myeloma) with an inhibitor of Gadd45β (for example an inhibitor of Gadd45β expression, activity or signalling) and/or of NF-kB signalling. Optionally, an indication of relatively low Gadd45β expression may indicate an alternative (non-Gadd45β inhibitor) treatment.

It is, of course, understood that whatever treatment is indicated, whether or not it may be an inhibitor of Gadd45β or an alternative treatment, such a treatment may be offered in combination with other treatments (for example surgical, chemotherapeutic, immunotherapeutic or radio-therapeutic treatments) as may be indicated by treatment protocols and/or clinical judgement.

Preferably a relatively high Gadd45β expression level indicates treatment with an inhibitor of Gadd45β which is specific for Gadd45β.

Gadd45B Inhibitors

A number of specific Gadd45β inhibitors are discussed in PCT/GB2010/001970 and are disclosed below merely as examples. The applicant contemplates embodiments of the theranostic aspects of the invention utilising the Gadd45β inhibitors specifically disclosed below. The applicant also contemplates embodiments of the theranostic aspects of the invention using Gadd45β inhibitors not specifically disclosed below. The right to claim, or in the alternative disclaim, the inhibitors specifically disclosed below in relation to the theranostic aspects of the invention is reserved.

Gadd45β inhibitors may be compounds of formula I:

$$X_1\text{-}A\text{-}X_2 \quad \quad \text{I:}$$

wherein,
A is A'''',
or A''-[M-A'-]$_n$ M-A''';
A'''' is A'',
A''',
or $Z_1$—$Y_2$—$Y_3$—$Z_4$, wherein $Y_2$—$Y_3$ is an oligopeptide moiety or an oligopeptoid moiety having the residues $Y_2$—$Y_3$ and $Z_1$ is attached to the N-terminal nitrogen of $Y_2$—$Y_3$ and $Z_4$ is attached to the C-terminal carbon of $Y_2$—$Y_3$;
A'' is A',
or $Y_1$—$Y_2$—$Y_3$—$Z_4$, wherein $Y_1$—$Y_2$—$Y_3$ is an oligopeptoid moiety or an oligopeptoid moiety comprising the residues: $Y_1$—$Y_2$—$Y_3$ and $Z_4$ is attached to the C-terminal carbon of $Y_1$—$Y_2$—$Y_3$;
A''' is A',
or $Z_1$—$Y_2$—$Y_3$—$Y_4$, wherein $Y_2$—$Y_3$—$Y_4$ is an oligopeptoid moiety or an oligopeptoid moiety comprising the residues $Y_2$—$Y_3$—$Y_4$ and $Z_1$ is attached to the N-terminal nitrogen of $Y_2$—$Y_3$—$Y_4$;

each occurrence of A' is independently an oligopeptide moiety or an oligopeptoid moiety comprising the residues $Y_1$—$Y_2$—$Y_3$—$Y_4$;

n is an integer from 0 to 18

$Y_1$ and $Y_4$ are independently amino acid residues or residues of amino acid derivatives having aromatic side chains; according to certain embodiments each side chain comprises an alkylene group of from one to three carbons which is substituted once or twice with a 5 to 10 membered carbocyclic or heterocyclic aromatic group and optionally further substituted by alkyl of from 1 to 4 carbon atoms; said aromatic group is optionally substituted by at least one substituent selected from hydroxyl, halogen or C1 to C4 alkyl or C1 to C4 alkoxy.

$Y_2$ is absent or is an amino acid residue or a residue of an amino acid derivative preferably any of the 20 natural amino acids in the L or D configuration and/or preferably an amino acid residue or a residue of an amino acid derivative having a side chain carrying preferably a negative charge in aqueous solution at pH 7;

$Y_3$ is an amino acid residue or a residue of an amino acid derivative preferably any of the 20 natural amino acids in the L or D configuration and/or preferably an amino acid residue or a residue of an amino acid derivative having a side chain carrying preferably a positive charge in aqueous solution at pH 7, Where $Y_2$ and $Y_3$ are both present in certain embodiments they are preferably such that a salt-bridge is able to form between the respective positive and negative charges of the side chains and/or are such that the distance between the aromatic centres on $Y_1$ and $Y_4$, or on $X_1$ and $X_4$, or on $X_1$ and $Y_4$, or on $Y_1$ and $X_4$ is no higher than 10 or 20 Angstroms and no smaller than 3 Angstroms. Preferably the side chains of $Y_2$ and $Y_3$ consist of no more than 30 atoms. $Y_2$ and $Y_3$ may be naturally occurring amino acids or N-methyl-amino acids in the L- or D-configuration.

$Z_1$ is a group of formula II:

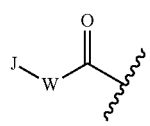

(II)

which is linked to the N-terminal nitrogen of $Y_2$,

W is absent, or an oxygen, or a nitrogen, or an alkylene group of from one to three carbons, which alkylene group of from one to three carbons is optionally substituted by at least one substituent selected from alkyl of from one to four carbons, or 5-10 membered carbocyclic or heterocyclic aromatic group;

J is a 5-10 membered carbocyclic or heterocyclic aromatic group, which aromatic group is optionally substituted by at least one substituent selected from hydroxyl, halogen, alkyl of from one to four carbons, or alkoxy of from one to four carbon atoms;

$Z_4$ represents a group of formula III:

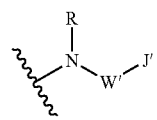

(III)

which is linked to the C-terminal carbon of $Y_3$,

R is hydrogen or alkyl of from one to four carbons;

W' is absent or an alkylene group of from one to three carbons, which alkylene group of from one to three carbons is optionally substituted by at least one substituent selected from alkyl of from one to four carbons, or 5-10 membered carbocyclic or heterocyclic aromatic group;

J' is a 3-10 membered aliphatic carbocyclic group or a 5-10 membered carbocyclic or heterocyclic aromatic group, which aliphatic or aromatic group is optionally substituted by at least one substituent selected from hydroxyl, halogen, alkyl of from one to four carbons, or alkoxy of from one to four carbon atoms;

M is a peptide bond between preceding oligopeptide or oligopeptoid moiety (A', A'' or A''') and following oligopeptide or oligopeptoid moiety (A', A'' or A''') or a linker moiety attached via an amide bond, an ester bond, an ether bond, or a thioether bond to the terminal carboxylic group of preceding oligopeptide or oligopeptoid moiety (A', A'' or A''') and via an amide bond, an ester bond, an ether bond, or a thioether bond to the terminal amino group of following oligopeptoid moiety (A', A'' or A''');

$X_1$ is absent, or is a moiety added to the amino terminal of A in order to block the free amino group;

$X_2$ is absent or is a moiety added to the carboxyl terminal of A in order to block the free carboxylic group;

According to certain embodiments W is absent or an alkylene of from 1 to 3 carbons.

Preferably $X_1$ and $X_2$ are moieties of no more than 30 (or more preferably 20 or 10) atoms, with the proviso that $X_1$ is absent if A comprises $Z_1$ and $X_2$ is absent if A comprises $Z_4$ (i.e., if there are no free amino or carboxyl groups at the termini of the molecule, $X_1$ and $X_2$ are not required);

or derivatives thereof, said derivatives being selected from the group consisting of:

a) oligomers or multimers of molecules of the compound of formula I, said oligomers and multimers comprising two or more molecules of the compound of formula I each linked to a common scaffold moiety via an amide bond formed between an amino or carboxylic acid group present in molecules of the compound of formula I and an opposite amino or carboxylic acid group on a scaffold moiety said scaffold moiety participating in at least 2 amide bonds,
b) derivatives comprising a molecule of the compound of formula I or an oligomer or multimer thereof as defined above in part a) conjugated via an amide bond, an ester bond, an ether bond or a thioether bond to:
PEG,
PEG-based compounds,
cell-penetrating peptides,
fluorescent dyes,
biotin or other tag moiety,
fatty acids,
nanoparticles of discrete size,
or chelating ligands complexed with metallic or radioactive ions.
c) derivatives comprising a molecule of the compound of formula I or an oligomer or multimer thereof as defined in part a) which has been modified by amidation, glycosylation, carbamylation, acylation, sulfation, phosphorylation, cyclization, lipidation, pegylation or linkage to a peptide or peptiod fusion partner to make a fusion peptide or fusion peptiod.
and
d) salts and solvates of a molecule of the compound of formula I or of a derivative thereof as defined in part a) or b) above.

According to certain embodiments:
$Y_1$ is D-tryptophan,
   L-tryptophan,
   D-tyrosine,
   L-tyrosine,
   D-3,3-diphenyl-alanine,
   L-3,3-diphenyl-alanine,
   D-H-3-(4-pyridyl) alanine,
   L-H-3-(4-pyridyl) alanine,
   D-H-3-(3-pyridyl) alanine,
   L-H-3-(3-pyridyl) alanine,
   D-H-3-(2-pyridyl) alanine,
   L-H-3-(2-pyridyl) alanine,
   D-2-amino-4-phenyl-butirric acid,
   L-2-amino-4-phenyl-butirric acid,
   D-H-4-hydroxy-phenyl-glycine,
   L-H-4-hydroxy-phenyl-glycine,
   D-3-(2-furyl)-alanine,
   L-3-(2-furyl)-alanine,
   L-homoPhenylalanine,
   D-homoPhenylalanine,
   D-3-(4-quinolyl)-alanine,
   L-3-(4-quinolyl)-alanine;
   D-naphtyl-alanine
   L-naphtyl-alanine
   p-hydroxy-Benzoic acid
   p-hydroxy-phenyl-acetic-acid
   3-(p-hydroxy-phenyl)-propionic-acid
   or N-methyl-derivatives in L- or D-configuration of any above
Alternatively $Y_1$ may be:
D-phenylalanine,
L-phenylalanine,
D-tryptophan,
L-tryptophan,
D-tyrosine,
L-tyrosine,
D-3,3-diphenyl-alanine,
L-3,3-diphenyl-alanine,
D-H-3-(4-pyridyl) alanine,
L-H-3-(4-pyridyl) alanine,
D-H-3-(3-pyridyl) alanine,
L-H-3-(3-pyridyl) alanine,
D-H-3-(2-pyridyl) alanine,
L-H-3-(2-pyridyl) alanine,
D-2-amino-4-phenyl-butirric acid,
L-2-amino-4-phenyl-butirric acid,
D-phenyl-glycine,
L-phenyl-glycine,
D-H-4-hydroxy-phenyl-glycine,
L-H-4-hydroxy-phenyl-glycine,
D-3-(2-furyl)-alanine,
L-3-(2-furyl)-alanine,
L-Cyclohexylalanine,
D-Cyclohexylalanine,
L-homoPhenylalanine,
D-homoPhenylalanine,
D-3-(4-quinolyl)-alanine,
L-3-(4-quinolyl)-alanine;
D-naphtyl-alanine
or L-naphtyl-alanine According to certain embodiments:
$Y_2$ is Absent
D-glutamic acid,
L-glutamic acid,
D-aspartic acid,
L-aspartic acid,
L-Leucine
D-Leucine
L-Glutamine
D-Glutamine
L-Methionine
D-Methionine
D-2-amino-heptanedioic acid,
L-2-amino-heptanedioic acid,
a methyl or ethyl ester of any thereof,
L-homoserine,
D-homoserine;
or N-methyl-derivatives in L- or D-configuration of any above Alternatively $Y_2$ may be:
D-glutamic acid,
L-glutamic acid,
D-aspartic acid,
L-aspartic acid,
D-2-amino-heptanedioic acid,
L-2-amino-heptanedioic acid,
a methyl or ethyl ester of any thereof,
L-homoserine,
or D-homoserine;

According to certain embodiments:
$Y_3$ is D-arginine,
L-arginine,
L-Proline
D-Proline
D-histidine,
L-histidine,
D-lysine,
D-α,β-diaminopropionic acid (D-Dap),
L-α,β-diaminopropionic acid (L-Dap),
L-α,δ-diaminobutirric acid (L-Dab),
L-α,δ-diaminobutirric acid (L-Dab),
L-ornitine,
D-ornitine,
L-lysine;
or N-methyl-derivatives in L- or D-configuration of any above Alternatively $Y_3$ may be
D-arginine,
L-arginine,
D-histidine,
L-histidine,
D-lysine,
D-α,β-diaminopropionic acid (D-Dap),
L-α,β-diaminopropionic acid (L-Dap),
L-α,δ-diaminobutirric acid (L-Dab),
L-α,δ-diaminobutirric acid (L-Dab),
L-ornitine,
D-ornitine,
or L-lysine;
According to certain embodiments:
$Y_4$ is
D-phenylalanine,
L-phenylalanine,
D-tryptophan,
L-tryptophan,
D-tyrosine,
L-tyrosine,
D-3,3-diphenyl-alanine,
L-3,3-diphenyl-alanine,
D-H-3-(4-pyridyl) alanine,
L-H-3-(4-pyridyl) alanine,
D-H-3-(3-pyridyl) alanine,
L-H-3-(3-pyridyl) alanine,
D-H-3-(2-pyridyl) alanine,
L-H-3-(2-pyridyl) alanine,
D-2-amino-4-phenyl-butirric acid,
L-2-amino-4-phenyl-butirric acid,
D-phenyl-glycine,
L-phenyl-glycine,
D-H-4-hydroxy-phenyl-glycine,
L-H-4-hydroxy-phenyl-glycine,
D-3-(2-furyl)-alanine,
L-3-(2-furyl)-alanine,
L-homoPhenylalanine,
D-homoPhenylalanine,
D-3-(4-quinolyl)-alanine,
L-3-(4-quinolyl)-alanine;
D-naphtyl-alanine
L-naphtyl-alanine
Their N-methyl-derivatives in L- or D-configuration
Aniline
benzylamine
or 2-phenyl-ethyl-amine
Alternatively $Y_4$ may be
D-phenylalanine,
L-phenylalanine,
D-tryptophan,
L-tryptophan,
D-tyrosine,
L-tyrosine,
D-3,3-diphenyl-alanine,
L-3,3-diphenyl-alanine,
D-H-3-(4-pyridyl) alanine,
L-H-3-(4-pyridyl) alanine,
D-H-3-(3-pyridyl) alanine,
L-H-3-(3-pyridyl) alanine,
D-H-3-(2-pyridyl) alanine,
L-H-3-(2-pyridyl) alanine,
D-2-amino-4-phenyl-butirric acid,
L-2-amino-4-phenyl-butirric acid,
D-phenyl-glycine,
L-phenyl-glycine,
D-H-4-hydroxy-phenyl-glycine,
L-H-4-hydroxy-phenyl-glycine,
D-3-(2-furyl)-alanine,
L-3-(2-furyl)-alanine,
L-Cyclohexylalanine,
D-Cyclohexylalanine,
L-homoPhenylalanine,
D-homoPhenylalanine,
D-3-(4-quinolyl)-alanine,
L-3-(4-quinolyl)-alanine;
D-naphtyl-alanine
or L-naphtyl-alanine According to certain preferred embodiments $Y_1$, $Y_2$, $Y_3$ and $Y_4$ are all as described above. According to certain embodiments $Y_1$, $Y_2$, $Y_3$ and $Y_4$ are all described above with the proviso that $Y_2$ is
D-glutamic acid,
L-glutamic acid,
D-aspartic acid,
L-aspartic acid,
D-2-amino-heptanedioic acid,
L-2-amino-heptanedioic acid,
a methyl or ethyl ester of any thereof;
L-homoserine,
L-Leucine
D-Leucine
L-Glutamine
D-Glutamine
L-Methionine
D-Methionine
D-homoserine,
or N-methyl-derivatives in L- or D-configuration of any above
and $Y_3$ is
D-arginine,
L-arginine,
D-histidine,
L-histidine,
D-lysine,
L-lysine;
L-Proline
D-Proline
D-α,β-diaminopropionic acid (D-Dap),
L-α,β-diaminopropionic acid (L-Dap),
D-α,δ-diaminobutirric acid (D-Dab),
L-α,β-diaminobutirric acid (L-Dab),
D-ornitine
L-ornitine
or N-methyl-derivatives in L- or D-configuration of any above According to certain embodiments $Y_1$ and $Y_2$ are both as described above but one or both of $Y_2$ and $Y_3$ are absent. According to certain embodiments M is a peptide bond.

According to certain embodiments $X_1$ is a hydrogen or $X_1$ is one of the following groups added to the amino terminal of the oligopeptide sequence so as to form an amide bond:
acetyl,
benzyloxycarbonyl,
2-chloro-benzyloxycarbonyl,
3-methoxy,4-hydroxy-benzoyl,
3-hydroxy,4-methoxy-benzoyl,
benzoyl,
or fluorenylmethoxycarbonyl;

$X_2$ is an hydroxyl group or is one of the following groups added to the carbonyl acid terminal of the oligopeptide sequence so as to form an amide bond:
amine,
D-phenylalanine, L-phenylalanine,
D-tryptophan,
L-tryptophan,
D-tyrosine,
L-tyrosine
D-3,3-diphenyl-alanine,
L-3,3-diphenyl-alanine,
D-H-3-(4-pyridyl)-alanine,
L-H-3-(4-pyridyl)-alanine,
D-H-3-(3-pyridyl)-alanine,
L-H-3-(3-pyridyl)-alanine,
D-H-3-(2-pyridyl)-alanine,
L-H-3-(2-pyridyl)-alanine,
D-2-amino-4-phenyl-butirric acid,
L-2-amino-4-phenyl-butirric acid,
D-phenyl-glycine,
L-phenyl-glycine,
D-H-4-hydroxy-phenyl-glycine,
L-H-4-hydroxy-phenyl-glycine,
D-3-(2-furyl)-alanine,
L-3-(2-furyl)-alanine,
L-Cyclohexylalanine,
D-Cyclohexylalanine,
L-homoPhenylalanine,
D-homoPhenylalanine,
D-3-(4-quinolyl)-alanine,
L-3-(4-quinolyl)-alanine;
D-naphtyl-alanine
L-naphtyl-alanine
or N-methyl-derivatives in L- or D-configuration of any above According to certain embodiments:

$Z_1$ Is 4-hydroxy-benzoyl,
(4-hydroxy-phenyl)-acetyl
3-(4-hydroxy-phenyl)-propionyl
benzoyl,
benzyloxycarbonyl,
2-phenyl-acetyl
3-phenyl-propionyl
3,3-diphenyl-propionyl
3-(1H-Indol-3yl)-propionyl
(1H-Indol-3-yl)-acetyl
Furan-2-yl-acetyl
Furan-3-yl-acetyl
3-pyridin-4-yl-propionyl
3-pyridin-3-yl-propionyl
3-pyridin-2-yl-propionyl
3-pyrimidin-4-yl-propionyl
3-pyridazin-4-yl-propionyl
3-[1,3,5]Triazin-2-yl-propionyl
2-pyridin-4-yl-acetyl
2-pyridin-3-yl-acetyl
2-pyridin-2-yl-acetyl
2-pyrimidin-4-yl-acetyl
2-pyridazin-4-yl-acetyl
2-[1,3,5]Triazin-2-yl-acetyl
Naphthalen-1-yl-acetyl
Naphthalen-2-yl-acetyl
2-Naphthalen-1-yl-propionyl
or 2-Naphthalen-2-yl-propionyl $Y_2$ is D-glutamic acid,
L-glutamic acid,
D-aspartic acid,
L-aspartic acid,
D-Leucine,
L-Leucine,
L-Glutamine,
D-Glutamine,
L-Methionine,
D-Methionine,
D-2-amino-heptanedioic acid,
L-2-amino-heptanedioic acid,
a methyl or ethyl ester of any thereof;
L-homoserine,
D-homoserine;
or N-methyl-derivatives in L- or D-configuration of any above $Y_3$ is D-arginine,
L-arginine,
D-histidine,
L-histidine,
L-proline,
D-proline,
D-lysine,
L-lysine;
D-α,β-diaminopropionic acid (D-Dap),
L-α,β-diaminopropionic acid (L-Dap),
D-α,δ-diaminobutirric acid (D-Dab),
L-α,δ-diaminobutirric acid (L-Dab),
D-ornitine
L-ornitine
or N-methyl-derivatives in L- or D-configuration of any above $Z_4$ is phenylamine,
benzylamine,
Phenetylamine
Cyclohexyl-amine
2-cyclohexyl-ethylamine
3-cyclohexyl-propylamine
4-(2-amino-ethyl)-phenol
4-amino-phenol
4-aminomethyl-phenol
1H-Indol-3-yl-amine
2-(1H-Indol-3-yl)-ethylamine
C-(1H-Indol-3-yl)-methylamine
2,2-diphenyl-ethylamine
2,2-dipyridin-4-yl-ethylamine
2-pyridin-4-yl-ethylamine
2-pyridin-3-yl-ethylamine
2-pyridin-2-yl-ethylamine
2-pyrimidin-4-yl-ethylamine
2-[1,3,5]Triazin-2-yl-ethylamine
C-furan-2-yl-methylamine
C-furan-3-yl-methylamine
or C-Naphthalen-2-yl-methylamine.

According to the convention all peptides and peptoids and regions thereof are described from the N terminus to the C terminus.

n may be 0, 1, 2, 3, 4, 5, 6, 7, 8, 9, 10, 11, 12, 13, 14, 15, 16, 17 or 18. According to certain preferred embodiments n=0.

According to certain preferred embodiments A is A'. In such embodiments the compound is therefore essentially a tetrapeptide, a tripeptide, or a dipeptide (or a corresponding peptoid) with optional blocking groups $X_1$ and $X_2$ at one or more of the termini.

Oligopeptides

Oligopeptides are short polymers formed by the condensation of α-amino acids (referred to herein as simply "amino acids"). The link between one amino acid residue and the next is known as a peptide bond or an amide bond.

Amino-Acids

As used herein the term "amino acid" includes the 20 standard amino acids (Isoleucine, Alanine, Leucine, Asparagine, Lysine, Aspartic Acid, Methionine, Cysteine, Phenylalanine, Glutamic Acid, Threonine, Glutamine, Tryptophan, Glycine, Valine, Proline, Serine, Tyrosine, Arginine and Histidine) in both their D and L optical configurations. It also includes synthetic α-amino acids in both D and L forms. According to certain embodiments the D configuration is preferred.

Amino Acid Derivatives

As used herein this term includes N-substituted glycines which differ from α-amino acids in that their side chains are appended to nitrogen atoms along the molecule's backbone, rather than to the α-carbons (as they are in amino acids). Also included in the term are methyl and ethyl esters of α-amino acids, β-amino acids and N-methylated α-amino acids.

Oligopeptoids

Strictly speaking, the term "oligopeptide" relates to oligomers of α-amino acids only. An analogous oligomer incorporating (at all or some residue positions) an amino acid derivate (for example an N-substituted glycine) is known as an oligopeptoid.

Derivatives

Preferably, derivatives of the Gadd45β inhibitors exemplified here are functional derivatives. The term "functional derivative" is used herein to denote a chemical derivative of a compound of formula (I) having the same physiological function (as the corresponding unmodified compounds of formula (I) or alternatively having the same in vitro function in a functional assay (for example, in one of the assays described in one of the examples disclosed herein).

Derivatives of the compounds may comprise the structure of formula (I) modified by well-known processes including amidation, glycosylation, carbamylation, acylation, for example acetylation, sulfation, phosphorylation, cyclization, lipidization and pegylation. The structure of formula (I) may be modified at random positions within the molecule, or at predetermined positions within the molecule and may include one, two, three or more attached chemical moieties. Derivatives include compounds in which the N-terminal $NH_2$ group is replaced with another group, for example a methoxy group.

A Gadd45β inhibitor may be a fusion protein, whereby the structure of formula (I) is fused to another protein or polypeptide (the fusion partner) using methods known in the art. Any suitable peptide or protein can be used as the fusion partner (e.g., serum albumin, carbonic anhydrase, glutathione-S-transferase or thioredoxin, etc.). Preferred fusion partners will not have an adverse biological activity in vivo. Such fusion proteins may be made by linking the carboxy-terminus of the fusion partner to the amino-terminus of the structure of formula (I) or vice versa. Optionally, a cleavable linker may be used to link the structure of formula (I) to the fusion partner. A resulting cleavable fusion protein may be cleaved in vivo such that an active form of the inhibitor is released. Examples of such cleavable linkers include, but are not limited to, the linkers D-D-D-D-Y [SEQ ID NO.: 227], G-P-R, A-G-G and H-P-F-H-L [SEQ ID NO.: 228], which can be cleaved by enterokinase, thrombin, ubiquitin cleaving enzyme and renin, respectively. See, e.g., U.S. Pat. No. 6,410,707.

A Gadd45β compound may be a physiologically functional derivative of the structure of formula (I). The term "physiologically functional derivative" is used herein to denote a chemical derivative of a compound of formula (I) having the same physiological function as the corresponding unmodified compound of formula (I). For example, a physiologically functionally derivative may be convertible in the body to a compound of formula (I). Examples of physiologically functional derivatives include esters, amides, and carbamates; preferably esters and amides.

Pharmaceutically acceptable esters and amides of the compounds may comprise a $C_{1-20}$ alkyl-, $C_{2-20}$ alkenyl-, $C_{5-10}$ aryl-, $C_{5-10}$ or —$C_{1-20}$ alkyl-, or amino acid-ester or -amide attached at an appropriate site, for example at an acid group. Examples of suitable moieties are hydrophobic substituents with 4 to 26 carbon atoms, preferably 5 to 19 carbon atoms. Suitable lipid groups include, but are not limited to, the following: lauroyl ($Ci_2H_{23}$), palmityl ($C_{15}H_{31}$), oleyl ($C_{15}H_{29}$), stearyl ($C_{17}H_{35}$), cholate; and deoxycholate.

Methods for lipidization of sulfhydryl-containing compounds with fatty acid derivatives are disclosed in U.S. Pat. Nos. 5,936,092; 6,093,692; and 6,225,445. Fatty acid derivatives of in inhibitor comprising an inhibitor linked to fatty acid via a disulfide linkage may be used for delivery of an inhibitor to neuronal cells and tissues. Lipidisation markedly increases the absorption of the compounds relative to the rate of absorption of the corresponding unlipidised compounds, as well as prolonging blood and tissue retention of the compounds. Moreover, the disulfide linkage in lipidised derivative is relatively labile in the cells and thus facilitates intracellular release of the molecule from the fatty acid moieties. Suitable lipid-containing moieties are hydrophobic substituents with 4 to 26 carbon atoms, preferably 5 to 19 carbon atoms. Suitable lipid groups include, but are not limited to, the following: palmityl ($C_{15}H_{31}$), oleyl ($C_{15}H_{29}$), stearyl ($C_{17}H_{35}$), cholate; and deoxycholate.

Cyclization methods include cyclization through the formation of a disulfide bridge and head-to-tail cyclization using a cyclization resin. Cyclized peptides may have enhanced stability, including increased resistance to enzymatic degradation, as a result of their conformational constraints. Cyclization may in particular be expedient where the uncyclized peptide includes an N-terminal cysteine group. Suitable cyclized peptides include monomeric and dimeric head-to-tail cyclized structures. Cyclized peptides may include one or more additional residues, especially an additional cysteine incorporated for the purpose of formation of a disulfide bond or a side chain incorporated for the purpose of resin-based cyclization.

A compound may be a pegylated structure of formula (I). Pegylated inhibitor compounds may provide additional advantages such as increased solubility, stability and circulating time of the polypeptide, or decreased immunogenicity (see U.S. Pat. No. 4,179,337).

Chemical moieties for derivitization of a compound may also be selected from water soluble polymers such as polyethylene glycol, ethylene glycol/propylene glycol copolymers, carboxymethylcellulose, dextran, polyvinyl alcohol and the like. A polymer moiety for derivatisation of an inhibitor may be of any molecular weight, and may be branched or unbranched. Polymers of other molecular weights may be used, depending on the desired therapeutic profile, for example the duration of sustained release desired, the effects, if any on biological activity, the ease in handling, the degree or lack of antigenicity and other known effects of the polyethylene glycol to a therapeutic protein or analog. For example, the polyethylene glycol may have an average molecular weight of about 200, 500, 1000, 1500, 2000, 2500, 3000, 3500, 4000, 4500, 5000, 5500, 6000, 6500, 7000, 7500, 8000, 8500, 9000, 9500, 10,000, 10,500, 11,000, 11,500, 12,000, 12,500, 13,000, 13,500, 14,000, 14,500, 15,000, 15,500, 16,000, 16,500, 17,000, 17,500, 18,000, 18,500, 19,000, 19,500, 20,000, 25,000, 30,000, 35,000, 40,000, 50,000, 55,000, 60,000, 65,000, 70,000, 75,000, 80,000, 85,000, 90,000, 95,000, or 100,000 kDa.

Salts and solvates of compounds that are suitable for use in a medicament are those wherein a counterion or associated solvent is pharmaceutically acceptable. However, salts and solvates having non-pharmaceutically acceptable counterions or associated solvents may also be used, for example, for use as intermediates in the preparation of the compounds of formula (I) and their pharmaceutically acceptable salts or solvates.

Suitable salts include those formed with organic or inorganic acids or bases. Pharmaceutically acceptable acid addition salts include those formed with hydrochloric, hydrobromic, sulphuric, nitric, citric, tartaric, acetic, phosphoric, lactic, pyruvic, acetic, trifluoroacetic, succinic, perchloric, fumaric, maleic, glycollic, lactic, salicylic, oxaloacetic, methanesulfonic, ethanesulfonic, p-toluenesulfonic, formic, benzoic, malonic, naphthalene-2-sulfonic, benzenesulfonic, and isetliionic acids. Other acids such as oxalic, while not in themselves pharmaceutically acceptable, may be useful as intermediates in obtaining the inhibitor compounds and their pharmaceutical acceptable salts. Pharmaceutically acceptable salts with bases include ammonium salts, alkali metal salts, for example potassium and sodium salts, alkaline earth metal salts, for example calcium and magnesium salts, and salts with organic bases, for example dicyclohexylamine and N-methyl-D-glucomine.

Those skilled in the art of organic chemistry will appreciate that many organic compounds can form complexes with solvents in which they are reacted or from which they are precipitated or crystallized. Such complexes are known as "solvates". For example, a complex with water is known as a "hydrate".

According to certain preferred embodiments, the compound as a half-life in the human circulation of at least 0.1, 0.2, 0.5, 1, 2, 3, 4, 5, 6, 7, 8, 9, 10, 11 or most preferably at least 12 hours.

Preferably, the compound retains at least 20, 30, 40, 50, 60, 70, 80, 90 or most preferably 99% of its capacity to bind to Gadd45β and/or MKK7 (and/or an association of both) as assessed in an in vitro binding assay, or at least 20, 30, 40, 50, 60, 70, 80, 90 or most preferably 99% of its capacity to block the Gadd45β interaction with MKK7 as assessed in an in vitro competitive binding assay following incubation in normal human serum for at 24 hours at 37 degrees Celsius.

Alternatively or additionally, the compound has at least one of the following activities:

a) The ability to inhibit at least 20, 30, 40, 50, 60, 70, 80, 90 or most preferably 99% of the MKK7 interactions with Gadd45β under the assay conditions described in the examples.

b) The ability in vitro to kill at least 20, 30, 40, 50, 60, 70, 80, 90 or most preferably 99% of cells in a culture of a human myeloma cell line selected from the group consisting of U266, KMS-11, NCI-H929, ARH-77, JJN-3, KMS-12, KMS-18, and KMS-27, or of a culture of the DLBCL cell line LY-3, or of a culture of the pro-monocytic cell line U937, or of a culture of the Burkitt's lymphoma cell line BJAB or a culture of primary tumour cells (for example primary multiple myeloma tumour cells) under conditions in which at least 90% of the T-cell line JURKAT is not killed.

According to certain preferred embodiments the oligopeptide core moiety of the compound, identified as A in Formula I has an amino acid sequence selected from the group consisting of:

[SEQ ID NO.: 2]
(L-Tyr)-(L-Asp)-(L-His)-(L-Phe),

[SEQ ID NO.: 3]
(L-Tyr)-(L-Glu)-(L-Arg)-(L-Phe),

[SEQ ID NO.: 4]
(L-Tyr)-(L-Glu)-(L-His)-(L-Phe),

[SEQ ID NO.: 5]
(L-Trp)-(L-Asp)-(L-His)-(L-Phe),

[SEQ ID NO.: 6]
(L-Trp)-(L-Glu)-(L-His)-(L-Phe),

[SEQ ID NO.: 7]
(L-Tyr)-(L-Asp)-(L-Arg)-(L-Phe),

[SEQ ID NO.: 8]
(L-Tyr)-(L-Asp)-(L-Lys)-(L-Phe),

[SEQ ID NO.: 9]
(L-Tyr)-(L-Glu)-(L-Lys)-(L-Phe),

[SEQ ID NO.: 10]
(L-Trp)-(L-Glu)-(L-Lys)-(L-Phe),

[SEQ ID NO.: 11]
(L-Trp)-(L-Glu)-(L-Arg)-(L-Phe),

[SEQ ID NO.: 12]
(L-Trp)-(L-Asp)-(L-Lys)-(L-Phe),

[SEQ ID NO.: 13]
(L-Trp)-(L-Asp)-(L-Arg)-(L-Phe),

[SEQ ID NO.: 14]
(L-Tyr)-(L-Asp)-(L-His)-(L-Trp),

[SEQ ID NO.: 15]
(L-Tyr)-(L-Glu)-(L-His)-(L-Trp),

[SEQ ID NO.: 16]
(L-Trp)-(L-Asp)-(L-His)-(L-Trp),

[SEQ ID NO.: 17]
(L-Trp)-(L-Glu)-(L-His)-(L-Trp),

[SEQ ID NO.: 18]
(L-Tyr)-(L-Asp)-(L-Arg)-(L-Trp),

[SEQ ID NO.: 19]
(L-Tyr)-(L-Asp)-(L-Lys)-(L-Trp),

[SEQ ID NO.: 20]
(L-Tyr)-(L-Glu)-(L-Lys)-(L-Trp),

[SEQ ID NO.: 21]
(L-Tyr)-(L-Glu)-(L-Arg)-(L-Trp),

[SEQ ID NO.: 22]
(L-Trp)-(L-Glu)-(L-Lys)-(L-Trp),

[SEQ ID NO.: 23]
(L-Trp)-(L-Glu)-(L-Arg)-(L-Trp),

[SEQ ID NO.: 24]
(L-Trp)-(L-Asp)-(L-Lys)-(L-Trp),

[SEQ ID NO.: 25]
(L-Trp)-(L-Asp)-(L-Arg)-(L-Trp),

[SEQ ID NO.: 26]
(L-Tyr)-(L-Asp)-(L-His)-(L-Tyr),

[SEQ ID NO.: 27]
(D-Tyr)-(D-Glu)-(D-Arg)-(D-Phe),

[SEQ ID NO.: 28]
(D-Tyr)-(D-Asp)-(D-His)-(D-Phe), (D-Trp)-(D-Glu)-(D-Arg)-(D-Phe), [SEQ ID NO.: 29]

(D-=Tyr)-(D-Asp)-(D-His)-(D-Phe), [SEQ ID NO.: 30]

(D-Tyr)-(D-Asp)-(D-Arg)-(D-Phe), [SEQ ID NO.: 31]

(D-Tyr)-(D-Asp)-(D-His)-(D-Tyr), [SEQ ID NO.: 32]

(D-Tyr)-(D-Glu)-(D-Arg)-(D-Tyr), [SEQ ID NO.: 33]

(D-Trp)-(D-Asp)-(D-His)-(D-Typ), [SEQ ID NO.: 34]

(D-Trp)-(D-Glu)-(D-Arg)-(D-Typ), [SEQ ID NO.: 35]

(D-Tyr)-(D-Asp)-(D-Lys)-(D-Phe), [SEQ ID NO.: 36]

(D-Tyr)-(D-Glu)-(D-His)-(D-Phe), [SEQ ID NO.: 208]

(D-Tyr)-(D-Asp)-(D-Lys)-(D-Phe), [SEQ ID NO.: 209]

(D-Trp)-(D-Glu)-(D-His)-(D-Phe), [SEQ ID NO.: 210]

(D-Tyr)-(D-Glu)-(D-Lys)-(D-Phe), [SEQ ID NO.: 211]

(D-Trp)-(D-Glu)-(D-Lys)-(D-Phe), [SEQ ID NO.: 212]

(D-Trp)-(D-Asp)-(D-Lys)-(D-Phe), [SEQ ID NO.: 213]

(D-Tyr)-(D-Asp)-(D-His)-(D-Trp), [SEQ ID NO.: 214]

(D-Tyr)-(D-Glu)-(D-His)-(D-Trp), [SEQ ID NO.: 215]

(D-Trp)-(D-Asp)-(D-His)-(D-Trp), [SEQ ID NO.: 216]

(D-Trp)-(D-Glu)-(D-His)-(D-Trp), [SEQ ID NO.: 217]

(D-Tyr)-(D-Asp)-(D-Arg)-(D-Trp), [SEQ ID NO.: 218]

(D-Tyr)-(D-Asp)-(D-Lys)-(D-Trp), [SEQ ID NO.: 219]

(D-Tyr)-(D-Glu)-(D-Lys)-(D-Trp), [SEQ ID NO.: 220]

(D-Tyr)-(D-Glu)-(D-Arg)-(D-Trp), [SEQ ID NO.: 221]

(D-Trp)-(D-Glu)-(D-Lys)-(D-Trp), [SEQ ID NO.: 222]

(D-Trp)-(D-Glu)-(D-Arg)-(D-Trp), [SEQ ID NO.: 223]

(D-Trp)-(D-Asp)-(D-Lys)-(D-Trp), [SEQ ID NO.: 224]

(D-Trp)-(D-Gln)-(D-Arg)-(D-Trp), [SEQ ID NO.: 225]

(D-Trp)-(D-Asn)-(D-Lys)-(D-Trp), [SEQ ID NO.: 226]

(L-Tyr)-(L-Asp)-(L-Phe), (D-Tyr)-(D-Asp)-(D-Phe), (L-Tyr)-(L-Glu)-(L-Phe), (L-Tyr)-(L-Arg)-(L-Phe), (D-Tyr)-(D-Arg)-(D-Phe), (D-Tyr)-(D-Glu)-(D-Phe), (D-Tyr)-(D-Pro)-(D-Phe)

(D-Tyr)-(D-Leu)-(D-Phe), (D-Tyr)-(D-Asp)-(D-Tyr), (D-Tyr)-(D-Glu)-(D-Tyr), (D-Tyr)-(D-Arg)-(D-Tyr), (D-Tyr)-(D-Pro)-(D-Tyr), (D-Tyr)-(D-Leu)-(D-Tyr), (D-Phe)-(D-Pro)-(D-Phe)

(D-Phe)-(D-Leu)-(D-Phe), (D-Phe)-(D-Arg)-(D-Tyr)

(D-Phe)-(D-Glu)-(D-Tyr), (D-Phe)-(D-Asp)-(D-Tyr), (D-Phe)-(D-Pro)-(D-Tyr)

(D-Phe)-(D-Leu)-(D-Tyr)

(D-Tyr)-(D-Pro)-(D-Trp)

(D-Tyr)-(D-Leu)-(D-Trp), (D-Tyr)-(D-Asp)-(D-Trp), (D-Tyr)-(D-Glu)-(D-Trp), (D-Tyr)-(D-Arg)-(D-Trp), (D-Tyr)-(D-Pro)-(D-Trp), (D-Tyr)-(D-Leu)-(D-Trp), (D-Phe)-(D-Pro)-(D-Trp)

(D-Phe)-(D-Leu)-(D-Trp), (D-Phe)-(D-Arg)-(D-Trp)

(D-Phe)-(D-Glu)-(D-Trp), (D-Phe)-(D-Asp)-(D-Trp), (D-Phe)-(D-Pro)-(D-Trp)
and (D-Phe)-(D-Leu)-(D-Trp)

In other embodiments the A moiety is selected from the group consisting of:
p-hydroxybenzoic acid-(L-Glu)-(L-Arg)-aniline
p-hydroxybenzoic acid-(D-Glu)-(L-Arg)-aniline
p-hydroxybenzoic acid-(L-Glu)-(D-Arg)-aniline
p-hydroxybenzoic acid-(D-Glu)-(D-Arg)-aniline
p-hydroxybenzoic acid-(L-Glu)-(L-Arg)-benzylamine
p-hydroxybenzoic acid-(D-Glu)-(L-Arg)-benzylamine
p-hydroxybenzoic acid-(L-Glu)-(D-Arg)-benzylamine
p-hydroxybenzoic acid-(D-Glu)-(D-Arg)-benzylamine p-hydroxybenzoic acid-(L-Glu)-(L-Arg)-2-phenyl-ethyl-amine
p-hydroxybenzoic acid-(D-Glu)-(L-Arg)-2-phenyl-ethyl-amine
p-hydroxybenzoic acid-(L-Glu)-(D-Arg)-2-phenyl-ethyl-amine
p-hydroxybenzoic acid-(D-Glu)-(D-Arg)-2-phenyl-ethyl-amine
2-(4-hydroxy-phenyl) acetic acid-(L-Glu)-(L-Arg)-aniline
2-(4-hydroxy-phenyl) acetic acid-(D-Glu)-(L-Arg)-aniline
2-(4-hydroxy-phenyl) acetic acid-(L-Glu)-(D-Arg)-aniline
2-(4-hydroxy-phenyl) acetic acid-(D-Glu)-(D-Arg)-aniline
2-(4-hydroxy-phenyl) acetic acid-(L-Glu)-(L-Arg)-benzylamine
2-(4-hydroxy-phenyl) acetic acid-(D-Glu)-(L-Arg)-benzylamine
2-(4-hydroxy-phenyl) acetic acid-(L-Glu)-(D-Arg)-benzylamine
2-(4-hydroxy-phenyl acetic acid-(D-Glu)-(D-Arg)-benzylamine
2-(4-hydroxy-phenyl) acetic acid-(L-Glu)-(L-Arg)-2-phenyl-ethyl-amine
2-(4-hydroxy-phenyl) acetic acid-(D-Glu)-(L-Arg)-2-phenyl-ethyl-amine
2-(4-hydroxy-phenyl) acetic acid-(L-Glu)-(D-Arg)-2-phenyl-ethyl-amine
2-(4-hydroxy-phenyl) acetic acid-(D-Glu)-(D-Arg)-2-phenyl-ethyl-amine
3-(4-hydroxy-phenyl) propionic acid-(L-Glu)-(L-Arg)-aniline
3-(4-hydroxy-phenyl) propionic acid-(D-Glu)-(L-Arg)-aniline
3-(4-hydroxy-phenyl) propionic acid-(L-Glu)-(D-Arg)-aniline
3-(4-hydroxy-phenyl) propionic acid-(D-Glu)-(D-Arg)-aniline
3-(4-hydroxy-phenyl) propionic acid-(L-Glu)-(L-Arg)-benzylamine
3-(4-hydroxy-phenyl) propionic acid-(D-Glu)-(L-Arg)-benzylamine
3-(4-hydroxy-phenyl) propionic acid-(L-Glu)-(D-Arg)-benzylamine
3-(4-hydroxy-phenyl) propionic acid-(D-Glu)-(D-Arg)-benzylamine
3-(4-hydroxy-phenyl) propionic acid-(L-Glu)-(L-Arg)-2-phenyl-ethyl-amine
3-(4-hydroxy-phenyl) propionic acid-(D-Glu)-(L-Arg)-2-phenyl-ethyl-amine
3-(4-hydroxy-phenyl) propionic acid-(L-Glu)-(D-Arg)-2-phenyl-ethyl-amine
3-(4-hydroxy-phenyl) propionic acid-(D-Glu)-(D-Arg)-2-phenyl-ethyl-amine
p-hydroxybenzoic acid-(L-Arg)-aniline
p-hydroxybenzoic acid-(D-Arg)-aniline
p-hydroxybenzoic acid-(L-Glu)-aniline
p-hydroxybenzoic acid-(D-Glu)-aniline
p-hydroxybenzoic acid-(L-Arg)-benzylamine
p-hydroxybenzoic acid-(D-Arg)-benzylamine
p-hydroxybenzoic acid-(L-Glu)-benzylamine
p-hydroxybenzoic acid-(D-Glu)-benzylamine
p-hydroxybenzoic acid-(L-Arg)-2-phenyl-ethyl-amine
p-hydroxybenzoic acid-(D-Arg)-2-phenyl-ethyl-amine
p-hydroxybenzoic acid-(D-Glu)-2-phenyl-ethyl-amine
p-hydroxybenzoic acid-(L-Glu)-2-phenyl-ethyl-amine
2-(4-hydroxy-phenyl) acetic acid-(L-Arg)-aniline
2-(4-hydroxy-phenyl) acetic acid-(D-Arg)-aniline
2-(4-hydroxy-phenyl) acetic acid-(L-Glu)-aniline
2-(4-hydroxy-phenyl) acetic acid-(D-Glu)-aniline
2-(4-hydroxy-phenyl) acetic acid-(D-Arg)-benzylamine
2-(4-hydroxy-phenyl) acetic acid-(L-Arg)-benzylamine
2-(4-hydroxy-phenyl) acetic acid-(D-Glu)-benzylamine
2-(4-hydroxy-phenyl) acetic acid-(L-Glu)-benzylamine
2-(4-hydroxy-phenyl) acetic acid-(L-Arg)-2-phenyl-ethyl-amine
2-(4-hydroxy-phenyl) acetic acid-(D-Arg)-2-phenyl-ethyl-amine
2-(4-hydroxy-phenyl) acetic acid-(L-Glu)-2-phenyl-ethyl-amine
2-(4-hydroxy-phenyl) acetic acid-(D-Glu)-2-phenyl-ethyl-amine
3-(4-hydroxy-phenyl) propionic acid-(L-Arg)-aniline
3-(4-hydroxy-phenyl) propionic acid-(D-Arg)-aniline
3-(4-hydroxy-phenyl) propionic acid-(L-Glu)-aniline
3-(4-hydroxy-phenyl) propionic acid-(D-Glu)-aniline
3-(4-hydroxy-phenyl) propionic acid-(L-Arg)-benzylamine
3-(4-hydroxy-phenyl) propionic acid-(D-Arg)-benzylamine
3-(4-hydroxy-phenyl) propionic acid-(L-Glu)-benzylamine
3-(4-hydroxy-phenyl) propionic acid-(D-Glu)-benzylamine
3-(4-hydroxy-phenyl) propionic acid-(L-Arg)-2-phenyl-ethyl-amine
3-(4-hydroxy-phenyl) propionic acid-(D-Arg)-2-phenyl-ethyl-amine
3-(4-hydroxy-phenyl) propionic acid-(L-Glu)-2-phenyl-ethyl-amine
3-(4-hydroxy-phenyl) propionic acid-(D-Glu)-2-phenyl-ethyl-amine In other embodiments the A moiety is selected from one of the sequences disclosed in the sequence listing filed herewith.

Alternatively, the moiety labelled as A' in Formula I may be an oligopeptide having an amino acid sequence selected from the group listed directly above.

According to certain embodiments the A' moiety is a peptide or peptoid moiety having the residues $Xaa_1$-$Xaa_2$-$Xaa_3$-$Xaa_4$ wherein:

$Xaa_1$ is L-Tyr, D-Tyr, N-methyl-L-Tyr, N-methyl-D-Tyr, p-hydroxybenzoic acid, 2-(4-hydroxy-phenyl) acetic acid, 3-(4-hydroxy-phenyl) propionic acid or acetyl $Xaa_2$ is L-Glu, D-Glu, L-Asp or D-Asp, N-methyl-L-Glu, N-methyl-D-Glu, N-methyl-L-Asp, N-methyl-D-Asp, L-Pro, D-Pro, N-methyl-L-Pro, N-methyl-D-Pro, L-Leu, D-Leu, N-methyl-L-Leu, N-methyl-D-Leu, or absent $Xaa_3$ is L-Arg, D-Arg, L-His or D-His, L-Lys, D-Lys, N-methyl-L-Arg, N-methyl-D-Arg, N-methyl-L-His, N-methyl-D-His, N-methyl-L-Lys, N-methyl-D-Lys, or absent; and $Xaa_4$ is aniline, benzylamine, 2-phenyl-ethyl-amine, L-Phe or D-Phe, N-methyl-L-Phe, N-methyl-D-Phe, L-Trp, D-Trp, N-methyl-L-Trp, N-methyl-D-Trp.

According to certain embodiments either $Xaa_2$ or $Xaa_3$ are absent but not both $Xaa_2$ and $Xaa_3$. According to other embodiments $Xaa_2$ and $Xaa_3$ are both absent.

M may be simply an amide bond between adjacent peptide or peptoid moieties. Alternatively, it may be a molecular moiety introduced as a spacer and attached to adjacent peptide or peptoid moieties by amide bonds.

M may be an additional amino acid. Preferably it is an additional amino acid with a non-bulky side chain, for example glycine, alanine or serine or derivatives of any thereof. Alternatively M may be a non-amino acid moiety, for example, ε-aminocaproic acid, 3-amino-propionic acid, 4-amino-butirric acid. Other moieties can be methyl-amine, ethyl-amine, propyl-amine, butyl-amine, methylene, di-methylene, tri-methylene or tetra-methylene. In all cases M should be such that its presence does not materially interfere with binding between the A' moiety and Gadd45β and/or MKK7. The extent of potential interference may be assessed by use of an in vitro binding assay.

Oligomers and Multimers

Gadd45β inhibitors may encompass oligomers or multimers of molecules of the compound of formula I, said oligomers and multimers comprising two or more molecules of the compound of formula I each linked to a common scaffold moiety via an amide bond formed between an amine or carboxylic acid group present in molecules of the compound of formula I and an opposite amino or carboxylic acid group on a scaffold moiety said scaffold moiety participating in at least 2 amide bonds.

According to certain embodiments the common scaffold may be the amino acid lysine. Lysine is a tri-functional amino acid, having in addition to the functional groups which define it as an amino acid, an amino group on its side claim. This tri-functional nature allows it to form three amide bonds with peptides, peptoids or similar molecules. Other tri-functional amino acids which may be used as a common scaffold include D-α,β-diaminopropionic acid (D-Dap), L-α,β-diaminopropionic acid (L-Dap), L-α,δ-diaminobutirric acid (L-Dab), L-α,δ-diaminobutirric acid (L-Dab), and L-ornitine, D-ornitine. Other tri-functional non-standard amino acids may also be used. The common scaffold may also comprise branched peptides, peptoids or similar molecules which incorporate tri-functional amino acids within their sequence and have at least three functionally active terminal groups able to form amide bonds.

Cell-Penetrating Peptides.

According to certain embodiments the compounds of formula I are conjugated to a cell penetrating peptide (CPP).

Such peptides may be attached to a compound of formula I either via one or more covalent bonds or by non-covalent associations.

CPPs may either directly penetrate the plasmalemma, for example the CPP may be Tat or a derivative, a peptide derived from the Antennapedia sequence, or a poly-arginine tag, a PTD-4 peptide, or a functionally equivalent cell-permeable peptide (Ho A, Schwarze S R, Mermelstein S J, Waksman G, Dowdy S F 2001 Synthetic protein transduction domains: enhanced transduction potential in vitro and in vivo. Cancer Res 61:474-477).

Alternatively, the CPP may enter the cell by mediating endocytosis or through mediating the formation of transitory membrane-spanning structures. For a discussion of cell penetrating peptides, the reader is directed to Wagstaff et al. (2006). Curr. Med. Chem. 13:171-1387 and references therein.

According to certain embodiments compounds may be conjugated to nano-particles (for example nano-Gold) in order to promote cellular uptake Fluorescent Dyes, Tag Moieties and Lipidated Derivatives.

Compounds of formula I may be conjugated to fluorescent dyes in order that their penetration into target tissues or cells may be monitored. Fluorescent dyes may be obtained with amino groups (i.e., succinimides, isothiocyanates, hydrazines), carboxyl groups (i.e., carbodiimides), thiol groups (i.e., maleimides and acetyl bromides) and azide groups which may be used to selectively react with the peptide moieties of compounds of formula I. Examples of fluorescent dyes include fluoresceine and its derivates, rhodamine and its derivatives.

Compounds of formula I may be conjugated to nanoparticles of discrete size such those described in Chithrani D B, Mol Membr Biol. 2010 Oct. 7, (Epub ahead of print) with a discrete size of up to 100 nm, whereby the peptides or their derivatives can be attached by a disulphide bridge to allow specific release within the reducing environment of the cytosol. Also peptide-nanoparticles conjugated via amide, ether, ester, thioether bonds can be used for the same purpose given the low toxicity of these compounds. Nanoparticles will favour cell uptake as well as will provide a mean to visualize and quantify cell uptake by fluorescence techniques (Schrand A M, Lin J B, Hens S C, Hussain S M., Nanoscale. 2010 Sep. 27, Epub ahead of print).

Tag moieties may be attached by similar means and similarly allow for monitoring of the success of targeting to tissues and cells.

Fatty acid derivatives of a compound comprising a compound of formula I linked to a fatty acid via a disulfide linkage may be used for delivery of an inhibitor compound to cells and tissues. Lipidisation markedly increases the absorption of the compounds relative to the rate of absorption of the corresponding unlipidised compounds, as well as prolonging blood and tissue retention of the compounds. Moreover, the disulfide linkage in lipidised derivative is relatively labile in the cells and thus facilitates intracellular release of the molecule from the fatty acid moieties. Suitable lipid-containing moieties are hydrophobic substituents with 4 to 26 carbon atoms, preferably 5 to 19 carbon atoms. Suitable lipid groups include, but are not limited to, the following: palmityl ($C_{15}H_{31}$), oleyl ($C_{15}H_{29}$), stearyl ($C_{17}H_{35}$), cholate; linolate, and deoxycholate.

Ion Conjugates

Compounds of formula I may be functionally attached to metallic or radioactive ions. This attachment is typically achieved by the conjugation of an ion chelating agent (for example EDTA) which is chelated with the ion. By such means radioactive ions (for example $^{99m}Tc$, $^{111}In$, $^{64}Cu$, $^{67}Cu$, $^{89}Sr$, $^{90}Y$, $^{117m}Sn$, $^{153}Sm$, $^{186}Re$, $^{188}Re$, or $^{177}Lu$) may be delivered to target cells as radiotherapy. Non-radioactive metallic ions (for example ions of gadolinium) may be used as a NMR-detectable marker.

Salts and Solvates

Salts and solvates of compounds that are suitable for use in a medicament are those wherein a counterion or associated solvent is pharmaceutically acceptable. However, salts and solvates having non-pharmaceutically acceptable counterions or associated solvents may also be used, for example, for use as intermediates in the preparation of the compounds of formula (I) and their pharmaceutically acceptable salts or solvates.

Suitable salts include those formed with organic or inorganic acids or bases. Pharmaceutically acceptable acid addition salts include those formed with hydrochloric, hydrobromic, sulphuric, nitric, citric, tartaric, acetic, phosphoric, lactic, pyruvic, acetic, trifluoroacetic, succinic, perchloric, fumaric, maleic, glycollic, lactic, salicylic, oxaloacetic, methanesulfonic, ethanesulfonic, p-toluenesulfonic, formic, benzoic, malonic, naphthalene-2-sulfonic, benzenesulfonic, and isethionic acids. Other acids such as oxalic, while not in themselves pharmaceutically acceptable, may be useful as intermediates in obtaining the inhibitor compounds and their pharmaceutical acceptable salts. Pharmaceutically acceptable salts with bases include ammonium salts, alkali metal salts, for example potassium and sodium salts, alkaline earth metal salts, for example calcium and magnesium salts, and salts with organic bases, for example dicyclohexylamine and N-methyl-D-glucosamine.

Those skilled in the art of organic chemistry will appreciate that many organic compounds can form complexes with solvents in which they are reacted or from which they are precipitated or crystallized. Such complexes are known as "solvates". For example, a complex with water is known as a "hydrate".

Examples of preferred molecules of formula I are given below. Where the L/D configuration of an amino acid residue is not specified, both configurations are encompassed Acetyl-Tyr-Glu-Arg-Phe-NH$_2$ [SEQ ID NO.: 37]
para-hydroxybenzoic acid-Glu-Arg-aniline
para-hydroxybenzoic acid-Glu-Arg-benzylamine
para-hydroxybenzoic acid-Glu-Arg-2-phenyl-ethyl-amine
2-(4-hydroxyphenyl) acetic acid-Glu-Arg-aniline
2-(4-hydroxyphenyl) acetic acid-Glu-Arg-benzylamine
2-(4-hydroxyphenyl) acetic acid-Glu-Arg-2-phenyl-ethyl-amine
3-(4-hydroxyphenyl) acetic acid-Glu-Arg-3-aniline
3-(4-hydroxyphenyl) acetic acid-Glu-Arg-benzylamine
3-(4-hydroxyphenyl) acetic acid-Glu-Arg-2-phenyl-ethyl-amine
Acetyl-Tyr-Asp-His-Phe-NH$_2$ [SEQ ID NO.: 38]
para-hydroxybenzoic-acid-Asp-His-aniline
para-hydroxybenzoic-acid-Asp-His-benzylamine
para-hydroxybenzoic-acid-Asp-His-3-phenyl-propyl-amine
2-(4-hydroxyphenyl) acetic acid-Asp-His-aniline
2-(4-hydroxyphenyl) acetic acid-Asp-His-benzylamine
2-(4-hydroxyphenyl) acetic acid-Asp-His-2-phenyl-ethyl-amine
3-(4-hydroxyphenyl) propionic acid-Asp-His-aniline
3-(4-hydroxyphenyl) propionic acid-Asp-His-benzylamine
3-(4-hydroxyphenyl) propionic acid-Asp-His-2-phenyl-ethyl-amine
Acetyl-Tyr-Asp-Lys-Phe-NH$_2$ [SEQ ID NO.: 39]
Acetyl-Tyr-Glu-Lys-Phe-NH$_2$ [SEQ ID NO.: 40]
Acetyl-Tyr-Glu-His-Phe-NH$_2$ [SEQ ID NO.: 41]
Acetyl-Tyr-Asp-Arg-Phe-NH$_2$, [SEQ ID NO.: 42]
Acetyl-Trp-Glu-His-Phe-NH$_2$, [SEQ ID NO.: 43]
Acetyl-Trp-Glu-Lys-Phe-NH$_2$, [SEQ ID NO.: 44]
Acetyl-Trp-Asp-His-Phe-NH$_2$, [SEQ ID NO.: 45]
Acetyl-Trp-Asp-Lys-Phe-NH$_2$, [SEQ ID NO.: 46]
Acetyl-Tyr-Glu-Arg-Tyr-NH$_2$ [SEQ ID NO.: 47]
Acetyl-Tyr-Asp-Lys-Tyr-NH$_2$ [SEQ ID NO.: 48]
Acetyl-Tyr-Glu-Lys-Tyr-NH$_2$ [SEQ ID NO.: 49]
Acetyl-Tyr-Glu-His-Tyr-NH$_2$ [SEQ ID NO.: 50]
Acetyl-Tyr-Asp-Arg-Tyr-NH$_2$, [SEQ ID NO.: 51]
Acetyl-Trp-Glu-His-Tyr-NH$_2$, [SEQ ID NO.: 52]
Acetyl-Trp-Glu-Lys-Tyr-NH$_2$, [SEQ ID NO.: 53]
Acetyl-Trp-Asp-His-Tyr-NH$_2$, [SEQ ID NO.: 54]
Acetyl-Trp-Asp-Lys-Tyr-NH$_2$, [SEQ ID NO.: 55]
internal lactam of acetyl-Tyr-Glu-Lys-Phe-NH$_2$ [SEQ ID NO.: 56]
Acetyl-Tyr-Gln-Arg-Phe-NH$_2$ [SEQ ID NO.: 57]
Acetyl-Tyr-Met-Arg-Phe-NH$_2$ [SEQ ID NO.: 58]
Acetyl-Tyr-Leu-Arg-Phe-NH$_2$ [SEQ ID NO.: 59]
Acetyl-Tyr-Arg-Phe-NH$_2$,
Acetyl-Tyr-Arg-Tyr-NH$_2$,
Acetyl-Tyr-Glu-Phe-NH$_2$,
Acetyl-Tyr-Glu-Tyr-NH$_2$,
Acetyl-Tyr-Asp-Phe-NH$_2$,
Acetyl-Tyr-Asp-Tyr-NH$_2$,
Acetyl-Tyr-Pro-Phe-NH$_2$,
Acetyl-Tyr-Lys-Phe-NH$_2$,
Acetyl-Tyr-His-Phe-NH$_2$,
H-Tyr-Arg-Phe-NH$_2$,
H-Tyr-Arg-Tyr-NH$_2$,
H-Tyr-Glu-Phe-NH$_2$,
H-Tyr-Glu-Tyr-NH$_2$,
H-Tyr-Asp-Phe-NH$_2$,
H-Tyr-Asp-Tyr-NH$_2$,
H-Tyr-Pro-Phe-NH$_2$,
H-Tyr-Lys-Phe-NH$_2$,
H-Tyr-His-Phe-NH$_2$,
Benzyloxycarbonyl-Tyr-Arg-Phe-NH$_2$,
Benzyloxycarbonyl-Tyr-Arg-Tyr-NH$_2$,
Benzyloxycarbonyl-Tyr-Glu-Phe-NH$_2$,
Benzyloxycarbonyl-Tyr-Glu-Tyr-NH$_2$,
Benzyloxycarbonyl-Tyr-Asp-Phe-NH$_2$,
Benzyloxycarbonyl-Tyr-Asp-Tyr-NH$_2$,
Benzyloxycarbonyl-Tyr-Pro-Phe-NH$_2$,
Benzyloxycarbonyl-Tyr-Lys-Phe-NH$_2$,
Benzyloxycarbonyl-Tyr-His-Phe-NH$_2$,
Benzyloxycarbonyl-Tyr-Glu-Arg-Phe-NH$_2$, [SEQ ID NO.: 60]
Benzyloxycarbonyl-Tyr-Asp-His-Phe-NH$_2$, [SEQ ID NO.: 61]
Benzyloxycarbonyl-Tyr-Asp(OMe)-His-Phe-NH$_2$, [SEQ ID NO.: 62]
Benzyloxycarbonyl-Tyr-Arg-Phe-NH$_2$,
Benzyloxycarbonyl-Tyr-Glu-Phe-NH$_2$,
Benzyloxycarbonyl-(N-methyl)Tyr-(N-methyl)Arg-(N-methyl)Phe-NH$_2$,
Benzyloxycarbonyl-(N-methyl)Tyr-Glu-(N-methyl)Phe-NH$_2$,
Benzyloxycarbonyl-Tyr-(N-methyl)Arg-(N-methyl)Phe-NH$_2$,
Benzyloxycarbonyl-(N-methyl)Tyr-(N-methyl)Arg-Phe-NH$_2$,
Benzyloxycarbonyl-Tyr-Glu-(N-methyl)Phe-NH$_2$,
Benzyloxycarbonyl-Tyr-(N-methyl)Glu-Phe-NH$_2$,
Benzyloxycarbonyl-(N-methyl)Tyr-Glu-Phe-NH$_2$,
Acetyl-(N-methyl)Tyr-(N-methyl)Arg-(N-methyl)Phe-NH$_2$,
Acetyl-(N-methyl)Tyr-Glu-(N-methyl)Phe-NH$_2$,
Acetyl-Tyr-(N-methyl)Arg-(N-methyl)Phe-NH$_2$,
Acetyl-(N-methyl)Tyr-(N-methyl)Arg-Phe-NH$_2$,
Acetyl-Tyr-Glu-(N-methyl)Phe-NH$_2$,
Acetyl-Tyr-(N-methyl)Glu-Phe-NH$_2$,
Acetyl-(N-methyl)Tyr-Glu-Phe-NH$_2$,
H—(N-methyl)Tyr-(N-methyl)Arg-(N-methyl)Phe-NH$_2$,
H—(N-methyl)Tyr-Glu-(N-methyl)Phe-NH$_2$,
H-Tyr-(N-methyl)Arg-(N-methyl)Phe-NH$_2$,
H—(N-methyl)Tyr-(N-methyl)Arg-Phe-NH$_2$,
H-Tyr-Glu-(N-methyl)Phe-NH$_2$,
H-Tyr-(N-methyl)Glu-Phe-NH$_2$,
H—(N-methyl)Tyr-Glu-Phe-NH$_2$,
Acetyl-Tyr-Glu-(β-homo)Phe-NH$_2$,
Acetyl-Tyr-(β-homo)Glu-Phe-NH$_2$,
Acetyl-(β-homo)Tyr-Glu-Phe-NH$_2$,
Acetyl-Tyr-Phe-NH$_2$,
Acetyl-Phe-Tyr-NH$_2$,
Benzyloxycarbonyl-Tyr-Phe-NH$_2$,
Benzyloxycarbonyl-Phe-Tyr-NH$_2$,
H-Tyr-Phe-NH$_2$,
H-Phe-Tyr-NH$_2$,
(3-Methoxy,4-hydroxy-benzoyl)-Tyr-Glu-Arg-Phe-NH$_2$, [SEQ ID NO.: 63]
(3-Methoxy,4-hydroxy-benzoyl)-Tyr-Asp-His-Phe-NH$_2$, [SEQ ID NO.: 64]
(3-Methoxy,4-hydroxy-benzoyl)-Tyr-Asp(OMe)-His-Phe-NH$_2$, [SEQ ID NO.: 65]
(3-Methoxy,4-hydroxy-benzoyl)-Tyr-Arg-Phe-NH$_2$,
(3-Methoxy,4-hydroxy-benzoyl)-Tyr-Glu-Phe-NH$_2$, Fluorenylmethyloxycarbonyl-Tyr-Glu-Arg-Phe-NH₂, [SEQ ID NO.: 66]
Fluorenylmethyloxycarbonyl-Tyr-Asp-His-Phe-NH₂, [SEQ ID NO.: 67]
Fluorenylmethyloxycarbonyl-Tyr-Asp(OMe)-His-Phe-NH₂, [SEQ ID NO.: 68]
Fluorenylmethyloxycarbonyl-Tyr-Asp(OMe)-His-Phe-NH₂ [SEQ ID NO.: 69]
Fluorenylmethyloxycarbonyl-Tyr-Arg-Phe-NH₂,
Fluorenylmethyloxycarbonyl-Tyr-Glu-Phe-NH₂,
Myristyl-Tyr-Glu-Arg-Phe-NH₂, [SEQ ID NO.: 70]
Myristyl-Tyr-Asp-His-Phe-NH₂, [SEQ ID NO.: 71]
Myristyl-Tyr-Arg-Phe-NH₂,
Myristyl-Tyr-Glu-Phe-NH₂,
Myristyl-Tyr-Asp(OMe)-His-Phe-NH₂, [SEQ ID NO.: 72]
Acetyl-Tyr-Glu-Arg-Phe-Gly-Tyr-Glu-Arg-Phe-NH₂, [SEQ ID NO.: 73]
Acetyl-Tyr-Asp-His-Phe-Gly-Tyr-Asp-His-Phe-NH₂, [SEQ ID NO.: 74]
Acetyl-Tyr-Arg-Phe-Gly-Tyr-Arg-Phe-NH₂, [SEQ ID NO.: 75]
Acetyl-Tyr-Asp(OMe)-His-Phe-Gly-Tyr-Asp(OMe)-His-Phe-NH₂, [SEQ ID NO.: 76]
benzyloxycarbonyl-Tyr-Glu-Arg-Phe-Gly-Tyr-Glu-Arg-Phe-NH₂, [SEQ ID NO.: 77]
benzyloxycarbonyl-Tyr-Asp-His-Phe-Gly-Tyr-Asp-His-Phe-NH₂, [SEQ ID NO.: 78]
benzyloxycarbonyl-Tyr-Arg-Phe-Gly-Tyr-Arg-Phe-NH₂, [SEQ ID NO.: 79]
benzyloxycarbonyl-Tyr-Asp(OMe)-His-Phe-Gly-Tyr-Asp(OMe)-His-Phe-NH₂, [SEQ ID NO.: 80]

Further examples of Gadd45β inhibitors include:

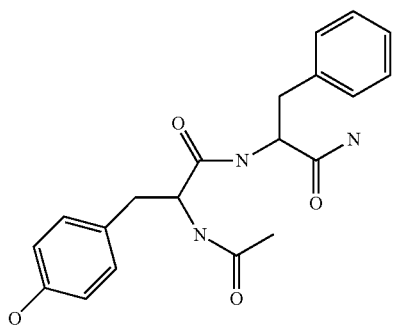

Compound A1
Ac-Tyr-Phe-NH2

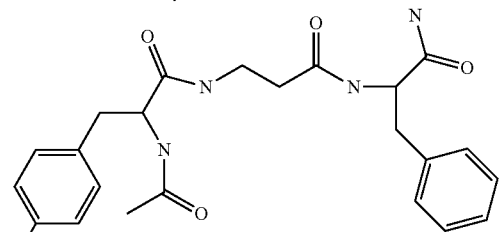

Compound A3
Ac-Tyr-bAla-Phe-NH2

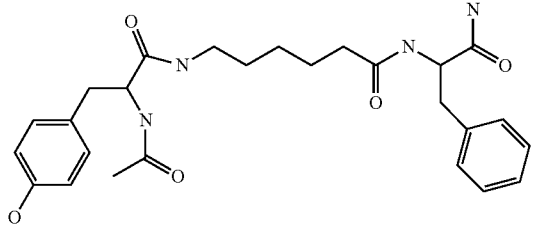

Compound A6
Ac-Tyr-(6-amino-caproic-acid)-Phe-NH2

Compound A7
Ac-Tyr-Tyr-NH₂

Compound A8
Ac-Phe-Tyr-NH₂

Compound A9
Ac-Phe-Arg-Phe-NH₂

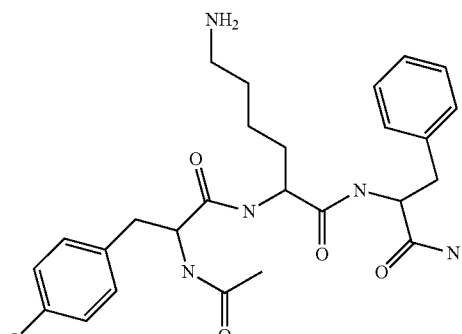

Compound B2
Ac-Tyr-Lys-Phe-NH₂

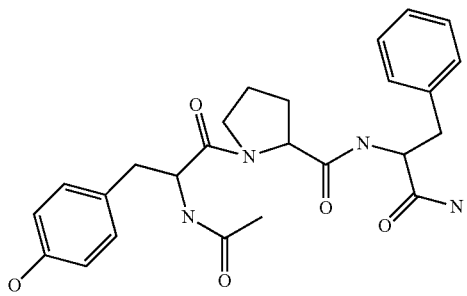

Compound B13
Ac-Tyr-Pro-Phe-NH2

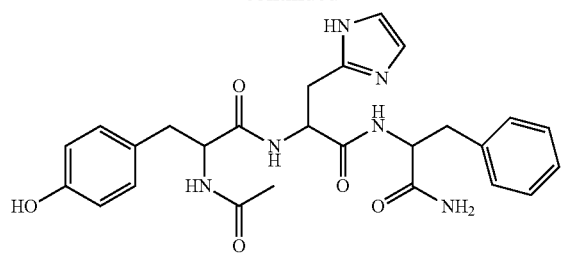

Compound B16
Ac-Tyr-His-Phe-NH2

Compound H1
L-3,3-diphenyl-alanine

Compound H2
L—H-3(4-pyridyl) alanine

Compound H3
L—H-4-hydroxy-phenyl-glycine

Compound H4
L-2-amino-4-phenyl-butirric acid

Compound H5
L-phenyl-glycine

Compound H6
L—H-4-hydroxy-phenyl-glycine

Compound H7
L-homoPhenylalanine

Compound H8
L-3-(2-furyl)-alanine

Compound H9
L-3-(4-quinolyl)-alanine

Compound H9
L-naphtyl-alanine

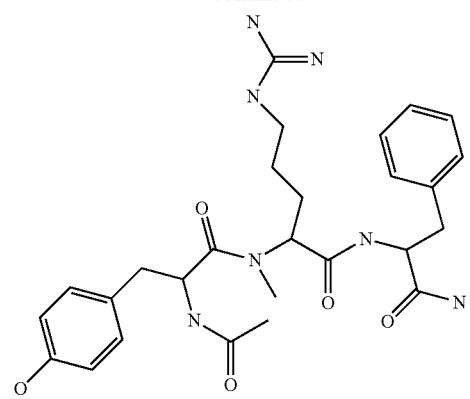

Compound I2
Ac-Tyr-(N—Me)Arg-Phe-NH2

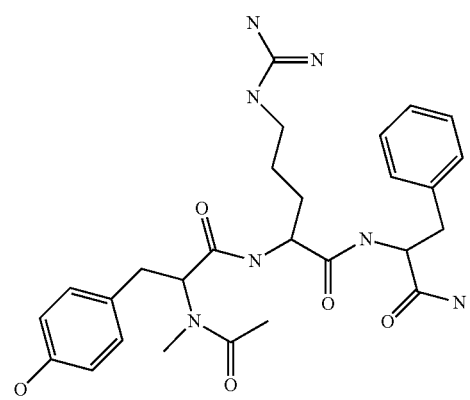

Compound I3
Ac—(N—Me)Tyr-Arg-Phe-NH2

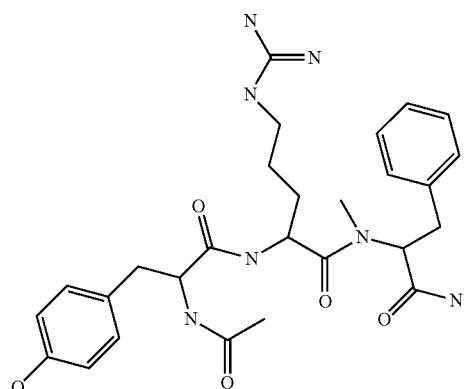

Compound I1
Ac-Tyr-(N—Me)Arg-Phe-NH2

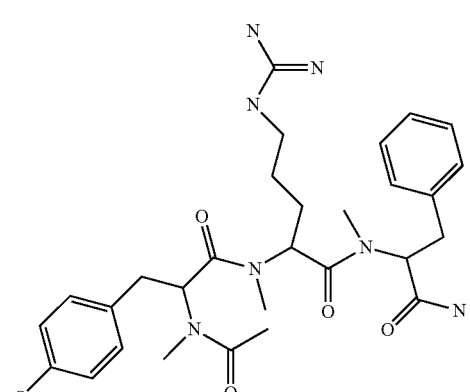

Compound I4
Ac—(N—Me)Tyr-(N—Me)Arg-(N—Me)Phe-NH2

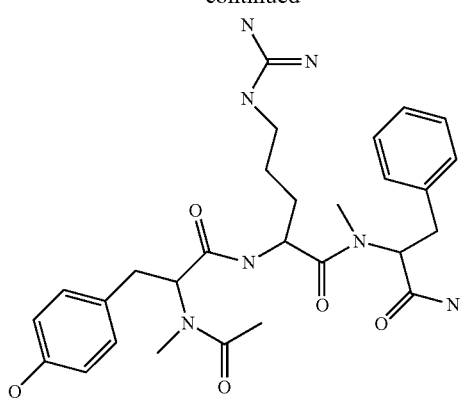

Compound I5
Ac—(N—Me)Tyr-Agr-(N—Me)Phe-NH₂

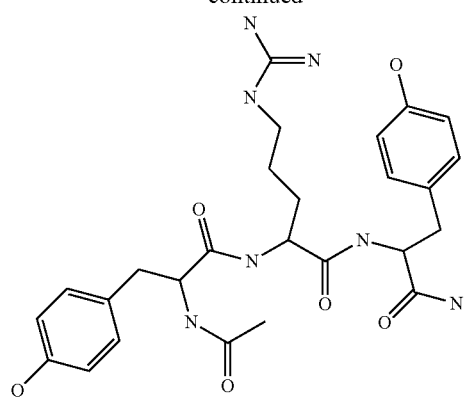

Compound O3
Ac-Tyr-Arg-Tyr-NH₂

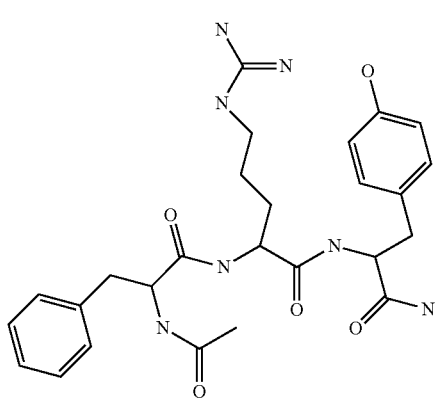

Compound O1
Ac-Phe-Arg-Tyr-NH₂

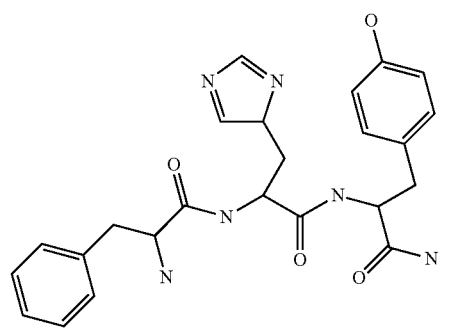

Compound O5
H-Phe-His-Tyr-NH₂

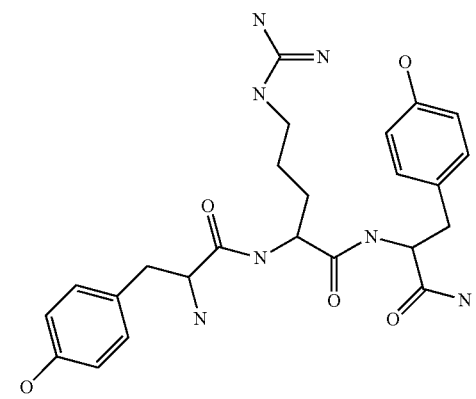

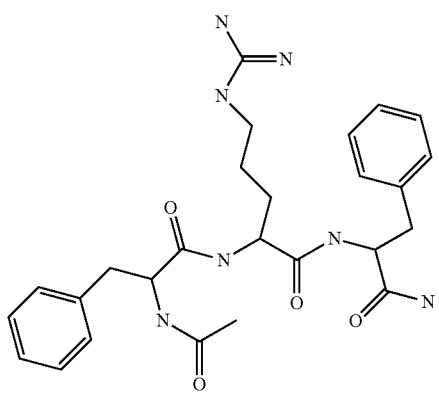

Compound O2
Ac-Phe-Arg-Phe-NH₂

Compound O7
H-Phe-His-Phe-NH₂

Compound O8
H-Phe-Arg-Tyr-NH₂

Compound O9
H-Phe-Arg-Phe-NH₂

Compound O10
H-Tyr-Arg-Tyr-NH₂

Compound P1
4-(hydroxyl)-phenyl-acetic acid-Arg-3-phenyl-ethylamine

Compound P2
4-(hydroxyl)-phenyl-acetic acid-His-3-phenyl-ethyl-amine

Compound P3
4-(hydroxyl)-phenyl-acetic acid-Glu-3-phenyl-ethylamine

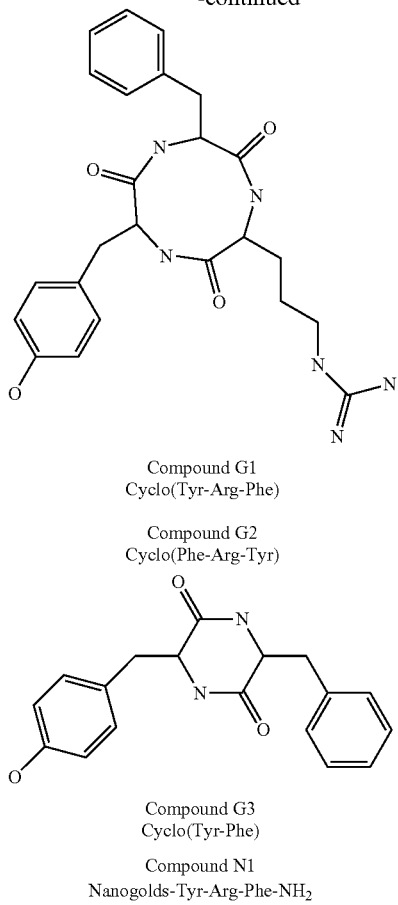

Compound G1
Cyclo(Tyr-Arg-Phe)

Compound G2
Cyclo(Phe-Arg-Tyr)

Compound G3
Cyclo(Tyr-Phe)

Compound N1
Nanogolds-Tyr-Arg-Phe-NH$_2$

Further examples of Gadd45β inhibitors are the peptides disclosed in the sequence listing filed herewith.

According to certain embodiments compounds disclosed specifically herein, including in the examples, are preferred compounds or are preferred embodiments of the A' moiety of formula I. Multimer versions or the specific compounds explicitly disclosed herein may be used. For example the 3 or 4 residue peptide or peptoid moieties of the specific compounds disclosed herein may correspond to the A, A', A", A''' or A'''' moiety of compounds of formula I.

This theranostic aspect of the invention is primarily illustrated by the results presented in FIGS. 3A, 3B and 4. The results shown here demonstrate that, in a panel of 29 cancer cell lines of different tissues of origin, cancer cell sensitivity to Z-DTP-induced killing correlates with a very high degree of statistical significance with levels of endogenus Gadd45β expression, as assessed by qRT-PCR assays. Indeed, the correlation plot of Gadd45β expression versus the percentage of cell survival/proliferation after treatment with Z-DTP2 shows that the significance of the correlation coefficient between the 2 parameters' domain is very high (p<0.01) (Pearson correlation). These data indicate it is possible to predict patient responder populations with respect to Gadd45β inhibitors via simple and cost-effective qRT-PCR analysis. For example, primary cell from multiple myeloma patients can be analysed for levels of Gadd45β expression, and patients with high levels of this expression can be deemed as those who will receive the most benefit from treatment with Gadd45β inhibitors. Hence, an important aspect of the invention is a theranostic aspect—that is the application of a clinically useful assay to predict Gadd45β-inhibitor therapy response in patients.

Datasets

According to a second aspect of the invention there is provided a dataset comprising the measured Gadd45β expression levels in cells obtained from a cohort of multiple subjects suspected or known to have a specific haematological malignancy.

The dataset may be stored on paper or in electronic or any other form. Preferably, it is a computer database which allows Gadd45β expression levels of cells obtained from a subject having a specific haematological malignancy to be compared with Gadd45β expression levels in comparable cells obtained from multiple further subjects having the same specific haematological malignancy.

EXAMPLES

Materials and Methods

Real Time Quantitative-PCR Reaction

RNA was extracted from frozen pellet using the DNA/RNA Purification Kit (Norgen, Thorold, Canada) following manufacturer instructions. RNA quantity and purity was determined with BioPhotometer PLUS (Eppendorf, Hamburg, Germany) and only samples with 260/280 ratio within 1.7 and 2.0 were used. Complementary DNA was produced using High capacity cDNA RT Kit (Applied Biosytem, Foster Ciy, Calif., USA). Quantitative reverse-transcriptase polymerase chain reaction (qRT-PCR) was performed using an ABI Prism 7900 HT (Applied Biosystems) with a relative quantification based on the ΔΔCt approach. JUM2 cell line was used as mathematical calibrator and GUS as housekeeping gene. All mRNA determinations were performed in duplicate. To evaluate the reproducibility of the analysis, the expression of both genes in 10 random samples between plates was investigated. An intra plate median variability of 0.9989% was obtained and an inter plate variability of 0.9586% indicating a comparable efficacy in all reactions.

Patients and Healthy Subjects

Samples used in the examples were derived from groups of subjects comprising: healthy persons, patients with Monoclonal Gammopathy of Undetermined Significance (MGUS), patients with previously untreated multiple myeloma (MM), patients with Waldström's macroglobulinemia (WM), patients with Chronic Lymphocytic Leukemia (CLL) and oncology patients having cancer (for example breast cancer) unrelated to MM (non-MM). Patients with MM were enrolled in the VMP-VMPT phase III clinical trials which compared 9 cycles of Velcade-Melphalan-Prednisone versus 9 cycles of Velcade-Melphalan-Prednisone-Thalidomide in elderly myeloma patients with or without maintenance (Palumbo A, Bringhen S, Rossi D, Cavalli M, Larocca A, Ria R, Offidani M, Patriarca F, Nozzoli C, Guglielmelli T, Benevolo G, Callea V, Baldini L, Morabito F, Grasso M, Leonardi G, Rizzo M, Falcone A P, Gottardi D, Montefusco V, Musto P, Petrucci M T, Ciccone G, Boccadoro M. Bortezomib-melphalan-prednisone-thalidomide followed by maintenance with bortezomib-thalidomide compared with bortezomib-melphalan-prednisone for initial treatment of multiple myeloma: a randomized controlled trial. J Clin Oncol. 2010 Dec. 1; 28(34):5101-9).

In this study only samples derived from a representative group of patients treated with nine 6-week cycles of Velcade-Melphalan-Prednisone at the standard dosage without maintenance were analysed.

The diagnosis of MM was done according to international standard criteria (Durie B G, Kyle R A, Belch A, Bensinger W, Blade J, Boccadoro M, Child J A, Comenzo R, Djulbegovic B, Fantl D, Gahrton G, Harousseau J L, Hungria V, Joshua D, Ludwig H, Mehta J, Morales A R, Morgan G, Nouel A, Oken M, Powles R, Roodman D, San Miguel J, Shimizu K, Singhal S, Sirohi B, Sonneveld P, Tricot G, Van Ness B; Scientific Advisors of the International Myeloma Foundation. Myeloma management guidelines: a consensus report from the Scientific Advisors of the International Myeloma Foundation. Hematol J. 2003; 4(6):379-98).

Blood cell count, organs function assessment using serological biomarker, beta-2-microglobulin and albumin levels, monoclonal component in serum and urine, bone lesion using X-ray, were investigated in every patients. Moreover, a bone marrow aspiration was performed for evaluation of tumor bone marrow infiltration at diagnosis. Anti-CD138-coated magnetic MicroBeads and AutoMACS Pro Separator (Miltenyi Biotech GmbH, Germany) were employed for separation of plasma cells. $CD19^+$ and B-cells were separated similarly using anti-CD19 magnetic beads.

Example 1

Gadd45β mRNA Expression in $CD138^+$ Cells at Diagnosis: MGUS Versus MM

The expression of Gadd45β mRNA was measured by real time quantitative RT-PCR in purified plasma cells (i.e. $CD138^+$ cells) obtained at diagnosis from patients with MGUS (12 patients) or MM (58 patients). The data were compared with the expression of Gadd45β observed in $CD19^+$ cells (CD19 is a marker for normal B-cells) purified from healthy donors (4 subjects) or patients with chronic lymphocytic leukaemia (5 patients). The results are shown in FIG. 1 and show that expression of Gadd45β was found to be significantly higher in patients with MM compared to patients with MGUS.

Example 1A

Figure 1A:
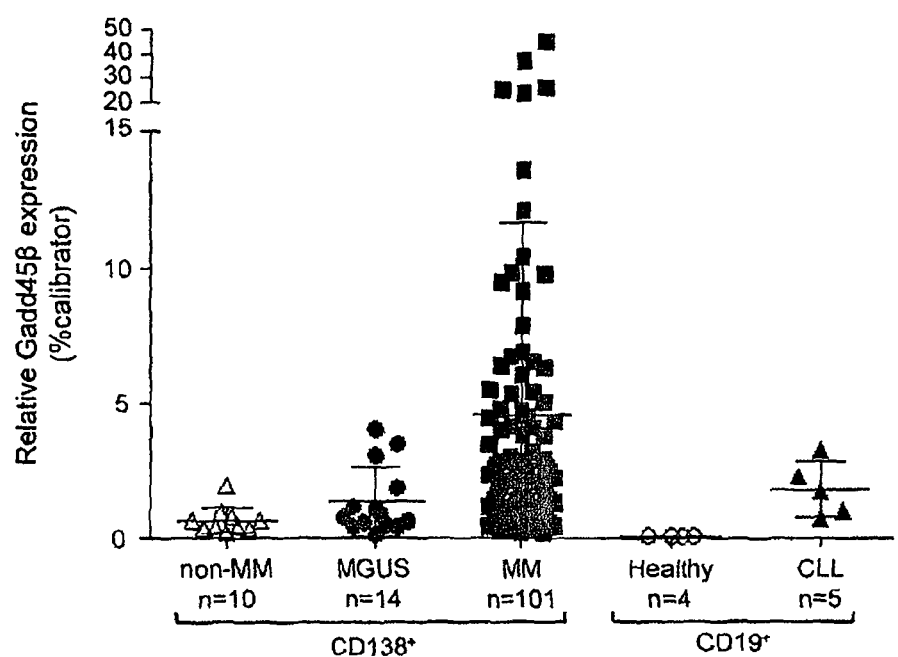
FIG. 1a shows Gadd45β mRNA expression in patients at diagnosis of either MGUS, MM or CLL. Expression measured in purified CD138$^+$ or CD19$^+$ cells as indicated in the figure Monoclonal (i.e. cancerous) CD138$^+$ plasma cells were from patients suffering from multiple myeloma (MM) (n=101) or monoclonal gammopathy of undetermined significance (MGUS) (n=14). Polyclonal (i.e. non-cancerous) CD138$^+$ plasma cells were from oncology patients suffering from cancers other than MM (non-MM) (n+10). CD19$^+$ B lymphocytes were from patients with chronic lymphocytic leukaemia (CLL) (n=5) or healthy subjects (n=4). Gadd45β mRNA levels were determined at diagnosis by qRT-PCR, and values were normalized to β-actin. The statistical significance of Gadd45β expression in CD138$^+$ cells from MM patients vs MUGS patients is very high (p=0.00018), as determined by t-student test.

Gadd45β mRNA Expression in $CD138^+$ Cells at Diagnosis MGUS, MM, CLL and Non-MM Malignancy The expression of Gadd45β mRNA was measured by real time quantitative RT-PCR in purified plasma cells (ie $CD138^+$ cells) obtained at diagnosis from people with MM (101 subjects) or MGUS (14 subjects). Expression was also measured in polyclonal (ie, non-cancerous) $CD138^+$ plasma cells from oncology patients with cancers other than MM (non-MM, 10 subjects). Expression was also measured in $CD19^+$ B-cells from patients with CLL (5 subjects) and from 4 healthy subjects. Gadd45β mRNA levels were determined by qRT-PCR and values were normalised to the housekeeping gene β-actin. The results are presented in FIG. 1A and show that cells from MM patients show significantly higher Gadd45β expression compared with cells from MGUS, CLL, non-MM oncology patients and healthy subjects. As determined by the t-student test the difference in Gadd45β mRNA expression between cells from MM patients and cells from MGUS patients is highly statistically significance at p=0.00018

Example 2

Gadd45β mRNA Expression in $CD138^+$ Cells Isolated from Patients Treated with VMP Schedule: PFS (Progression-Free Survival)

The value of expression of Gadd45β mRNA was measured using real time quantitative PCR in purified plasma cells obtained at diagnosis from patients with MM. The patients were sub-divided into two groups based on the values of Gadd45β mRNA expression. Patients with expression below the $33^{rd}$ percentile value were categorized as having LOW Gadd45β expression. Patients with expression between the $33^{rd}$ and $66^{th}$ percentile values were categorized as having INTERMEDIATE Gadd45β expression. Patients with expression above the $66^{th}$ percentile value were categorised as having HIGH Gadd45β expression. The clinical outcome in the three groups of patients was followed. As it can be seen from FIG. 2, there is a statistically significant difference in progression-free survival between the patients categorised as belonging to the LOW expression group and patients categorised as belonging to the INTERMEDIATE or HIGH expression groups.

Example 3

In order to determine the basis for the different sensitivity of tumour cell lines to Z-DTP-induced killing, we measured levels of Gadd45β expression in a panel of 29 tumour cell lines or different tissues of origin by using quantitative real-time polymerase chain reaction (qRT-PCT) and correlated these levels with the degree of susceptibility of these cell lines to the cytotoxic activity of Z-DTPs. For these analyses, which are shown in FIG. 3, the breast cancer and HEK-293T cell lines were cultured in 75 $cm^2$ flasks ($5\times10^6$ cells/flask) in complete DMEM medium, whereas all the other cell lines were cultured in wells of 6-well plates at $5\times10^5$ cells/well in complete RPMI-1640 medium as described above. Total RNA was extracted with Trizol and purified using the PureLike RNA mini-kit (Invitrogen). 1 µg of RNA was added as template to reverse-transcriptase (RT) reactions performed using the GeneAmp RNA PCR Kit (Applied Biosystems). qRT-PCRs were carried out with the resulting cDNAs in triplicate using SYBR Green PCR Master Mix (Applied Biosystems), Gadd45β-specific primers and an ABI 7900 real-time PCR machine. Experimental Ct values were normalized to β-actin, and relative mRNA expression calculated versus a reference sample (i.e. mRNA from HEK-293T cells). The sensitivity of cancer cell lines to Z-DTP-induced killing was analysed as described above by performing [$^3$H]thymidine incorporation assays after treatment of the cells with 10 µM of Z-DTP2 for 144 hrs. Also shown in FIG. 3 is the correlation plot of mRNA Gadd45β expression versus the percentage of cell survival after treatment with Z-DTP2. The significance of the correlation coefficient between the 2 parameters' domain was calculated by Pearson correlation, which quantifies the association between two variables, using the GraphPad software.

Example 4

Synthesis of Z-DTP2 as an Example of a Gadd45β Inhibitor

By way of example, the synthesis of Z-DTP2 is reported. Z-DTP2 comprises a tetrapeptide core made up of D-tyrosine, D-glutamine, D-arginine, D-phenylalanine with benzyloxycarbonyl (that is a Z group) bonded to the N-terminus by means of an amide bond and an amino group bonded to the C-terminus by means of an amide bond.
Materials and Methods Z-DTP2 was manually prepared following the Fmoc/tBu solid phase method (Fields G. B. and Noble R. L. 1990 *Int J Pept Protein Res;* 35: 161-214; Bodansky, M. and Bodansky A. 1995). The practice of peptide synthesis, 2nd edn., Springer Verlag, Berlin) and starting from 500 μmoles (1000 mg) of Rink amide polystyrene resin (Fmoc-RINK-AM-resin, GL Biochem, Shangai, China, Cat. 49001), having a substitution of 0.50 mmoles/g. The resin was placed in a 30 mL polypropylene vessel endowed with a 20 μm teflon septum, a polypropylene upper cap and a lower luer-lock polypropylene cap. The resin was swollen with 10.0 mL of a 50:50 dichloromethane (DCM):dimethyl formamide (DMF) mixture (both from LabScan, Stillorgan, Ireland; DCM cat. No H6508L; DMF cat. No H33H11X) for 20 minutes. Then after solvent removal under vacuum, the Fmoc group was cleaved by treatment with 5.0 mL of a DMF-Piperidine 8:2 mixture (Piperidine, Pip, cat. No Cat. No 80641; Sigma-Aldrich, Milan, Italy) for 20 minutes at room temperature (RT). The reactant was removed under vacuum and the resin washed 3 times with 5.0 mL of DMF. Then, 2.5 mmoles, 0.97 g, of Fmoc-D-Phe-OH (GL Biochem, Shangai. Cat. N. 35702) were dissolved in 5.0 mL of DMF (final conc. 0.5 M) and activated with 5.0 mL of a 0.5 M solution of Benzotriazole-1-yl-oxy-tris-pyrrolidino-phosphonium hexafluorophosphate (PyBOP, Novabiochem, cat. No 01-62-0016) in DCM, and 0.90 mL of di-iso-propyl-ethylamine (5.0 mmoles; DIEA, Sigma-Aldrich, cat. No D-3887). The solution of activated aminoacid was poured onto the resin and left under vigorous stirring for 30 minutes. The solution was drained under vacuum and the resin washed 3 times with 5.0 mL of DMF. The Fmoc group on the α-$NH_2$ was removed as described earlier using a 8:2 DMF-Pip solution (5.0 mL) for 20 minutes and extensive washing with 5.0 mL of DMF (3 times). A solution of Fmoc-D-Arg(Pbf)-OH (2.5 mmoles, 1.6 g in 5.0 mL DMF; GL Biochem, Shangai, Cat. N. 36404) was activated as described using 2.5 mmoles of PyBOP and 5.0 mmoles of pure DIEA. The solution was transferred onto the resin and left under stirring for 30 minutes. After cleavage of the Fmoc groups with 5.0 mL of a 8:2 DMF-Pip solution and washing with DMF (3 times, 5.0 mL), a solution of Fmoc-(D)-Glu (tBu)-OH 0.50 M in DMF (2.5 mmoles, 1.1 g in 5.0 mL DMF; GL Biochem, Shangai, Cat. N. 36605) preactivated with PyBOP and DIEA as described above, was added to the resin and the reaction was left to proceed for 30 minutes at room temperature. Following draining of the aminoacid, the Fmoc-group was removed as described above (20 minute treatment with 8:2 DMF:Pip, 5.0 mL) and the resin washed 3 times with 5.0 mL of DMF. 2.5 mmoles of Fmoc-(D)-Tyr (tBu)-OH (1.2 g, GL Biochem, Shangai, Cat. N. 36906) dissolved in 5.0 mL of DMF was preactivated with PyBOP and DIEA as reported above, was transferred onto the resin and left under stirring for 45 minutes. The amino acid solution was removed by vacuum draining, then the resin was washed 5 times with 5.0 mL of DMF. 5 mmoles of Z—OSu (benzyloxycarbonyl-N-hydroxy-succinimide, GL Biochem, Shangai, Cat. N. 10502) were dissolved in 10 mL of DMF and added to the resin. 2.4 mL of DIEA were added and the reaction was left under stirring over night. After draining of the solution, the resin was extensively washed with DMF, DCM, methyl alcohol (MeOH, LabScan, Cat. No C2517), and ethyl ether ($Et_2O$, LabScan, Cat. No A3509E), and dried under vacuum and weighted. The weight was 1.1 g. To cleave the peptide, the resin was treated with 10.0 mL of a mixture composed of TFA-$H_2O$-TIS 90:5:5 (v/v/v) mixture (TFA, trifluoroacetic acid, Sigma-Aldrich, Italy Cat. No 91700; TIS, tri-iso-propylsilane, Sigma-Aldrich, cat. N. 23, 378-1) for 3 hours at RT. The resin was removed by filtration, then 20 mL of cold $Et_2O$ was added to the trifluoroacetic solution, leading to the formation of a white precipitate. After removal of the solvents by centrifugation, the precipitate was washed with 10.0 mL of cold $Et_2O$, dissolved in 10.0 mL of $H_2O/CH_3CN$ 50:50 (v/v) and lyophilized. The peptide was characterized by LC-MS using a narrow bore 50×2 mm ID ONYX C18 column (Phenomenex, Torrance, Calif., USA), equilibrated at 600 μL/min with 5% $CH_3CN$, 0.05% TFA. The analysis was carried out applying a gradient of $CH_3CN$, 0.05% TFA from 5% to 70% over 3 minutes. The peptide was purified by semi-preparative RP-HPLC using a 10×1 cm C18 ONYX column (Phenomenex, Torrance, Calif., USA), equilibrated at 20 mL/min, injecting 20 mg in each run. A gradient from 5% to 65% over 8 minutes was applied to elute the peptide. Pure fractions were pooled and characterized by LC-MS. The determined MW of Peptide A was 746.8 amu (theor. 746.83 amu) and the product was more than 95% pure (HPLC). A yield of around 60% was achieved after purification of all the crude product.

Example 5

Correlation Between Gadd45β_Expression and Cytotoxic Activity in Primary Cells in Response to Gadd45β/MKK7 Inhibitors Expression of Gadd45β_mRNA was measured as described in other examples above in PBMCs from a healthy subject, and CD138+ cells from nine individual subjects suffering from multiple myeloma (MM) and from two individual subjects suffering from Waldenström's

The invention claimed is:

1. A method of treating a hematological malignancy in a subject in need thereof, the method comprising administering a Gadd45β inhibitor to the subject, wherein the Gadd45β expression level in a sample of CD138 positive cells from the subject is higher than in HEK-293T cells cultured in complete RPMI-1640 medium, and wherein the Gadd45β inhibitor is mDTP3.

2. The method of claim 1, wherein the haematological malignancy is multiple myeloma.

3. The method of claim 1, wherein the haematological malignancy is diffuse large B-cell lymphoma.

4. The method of claim 1, wherein the sample of CD138 positive cells is a blood sample, or biopsy of bone marrow, lymph node, kidney, spleen or bone.

5. The method of claim 2, wherein said Gadd45β expression levels is a mRNA levels as measured by RT-PCR or other nucleic acid amplification techniques or by a quantitative or semi-quantitative hybridisation technique.

6. The method of claim 2, wherein said Gadd45β expression level is a protein levels as measured by flow cytometry, Western blotting, RIA, ELISA or other immunoassay.

* * * * *